(12) United States Patent
Baltrusch et al.

(10) Patent No.: US 6,498,239 B1
(45) Date of Patent: Dec. 24, 2002

(54) STEROL GLYCOSYL TRANSFERASES

(75) Inventors: Martina Baltrusch, deceased, late of Göttingen (DE), by Andreas Baltrusch, heir; Ernst Heinz, Hamburg (DE); Dirk Warnecke, Hamburg (DE); Frank P. Wolter, Hamburg (DE)

(73) Assignee: Gesellschaft fur Erwerb und Verwertung von Schutzrechten—GVS mbH, Bonn (DE)

( * ) Notice: Subject to any disclaimer, the term of this patent is extended or adjusted under 35 U.S.C. 154(b) by 0 days.

(21) Appl. No.: 09/284,768

(22) PCT Filed: Oct. 10, 1997

(86) PCT No.: PCT/DE97/02335

§ 371 (c)(1),
(2), (4) Date: Aug. 18, 1999

(87) PCT Pub. No.: WO98/17789

PCT Pub. Date: Apr. 30, 1998

(30) Foreign Application Priority Data

Oct. 21, 1996 (DE) .......................................... 196 43 309

(51) Int. Cl.[7] ........................ C07H 21/02; C07H 21/04; A01N 63/00; C12P 21/06; A01H 5/00
(52) U.S. Cl. .................. 536/23.1; 536/23.72; 424/93.2; 424/93.6; 435/69.1; 435/235.1; 435/320.1; 435/172.1; 800/20.5; 800/250
(58) Field of Search ............................... 424/93.2, 93.6; 435/69.1, 235.1, 320.1, 172.1; 536/23.1, 23.72

(56) References Cited

U.S. PATENT DOCUMENTS 5,589,619 A * 12/1996 Chappell et al. ............ 800/205
5,662,897 A * 9/1997 Miller et al. ................ 424/93.2

OTHER PUBLICATIONS

Nomura, T. et al., "Pharmacological studies on steryl-β-D-glucosides (II)," *Japanese Journal of Pharmacology*, vol. 28, Supp. 110P (1978).

King et al., "Sterols and Triterpenoids of *Gymnosporia Trilocularis*Hay," *J. Nat. Prod.*, vol. 42, p. 701 (1979).

Miles et al., "Investigation of Constituents and Antitumor Activity of *Spartina Cynosuroides*," *J. Nat. Prod.*, vol. 42, p. 700 (1979).

Zaret et al., "DNA Sequence Required for Efficient Transcription Termination in Yeast," *Cell*, vol. 28, p. 563 (1982).

Okuyama et al., "The Principles of *Tetragonia Tetragonoides* Having an Antiulcerogenic Activity," *Journal of the Pharmaceutical Society of Japan*, vol. 103, p. 43 (1983).

Seki et al., "Plasma Lipoproteins as Drug Carriers: Pharmacological Activity and Disposition of the Complex of β-Sitosteryl-β-D-glucopyranoside with Plasma Lipoproteins," *Journal of Pharmaceutical Sciences*, vol. 74, No. 12, p. 1259 (1985).

Bauw et al., "Protein-Electroblotting on Polybase-Coated Glass-Fiber and Polyvinylidene Difluoride Membranes: An Evaluation," *Journal of Protein Chemistry*, vol. 7, No. 4, p. 194 (1988).

Sikorski et al., "A System of Shuttle Vectors and Yeast Host Strains Designed for Efficient Manipulation of DNA in *Saccharomyces Cerevisiae*," *Genetics*, vol. 122, p. 19 (1989).

Warnecke et al., "Purification of Membrane-Bound UDP-Glucose:Sterol β-D-Glucosyltransferase Based on Its Solubility in Diethyl Ether," *Plant Physiol.*, vol. 105, p. 1067 (1994).

Warnecke, et al. 1999.Cloning and Functional Expression of UGT Genes Encoding Sterol Glucosyltransferases from *Saccharomyces cerevisiae*, *Candida albicans*, *Pichia pastoris*, and *Dictyostelium discoideum*. *The Journal of Biological Chemistry*, 274(19):13048–13059.

* cited by examiner

*Primary Examiner*—W. Gary Jones
*Assistant Examiner*—Arun K. Chakrabarti
(74) *Attorney, Agent, or Firm*—Knobbe Martens Olson & Bear, LLP

(57) ABSTRACT

The invention relates to DNA sequences coding for sterol glucosyl transferases as well as the use thereof to modify the content and/or the structure of sterol glycosides and/or their synthetic secondary products in transgenic organism.

26 Claims, 28 Drawing Sheets

FIG. 1

Figure 6A:
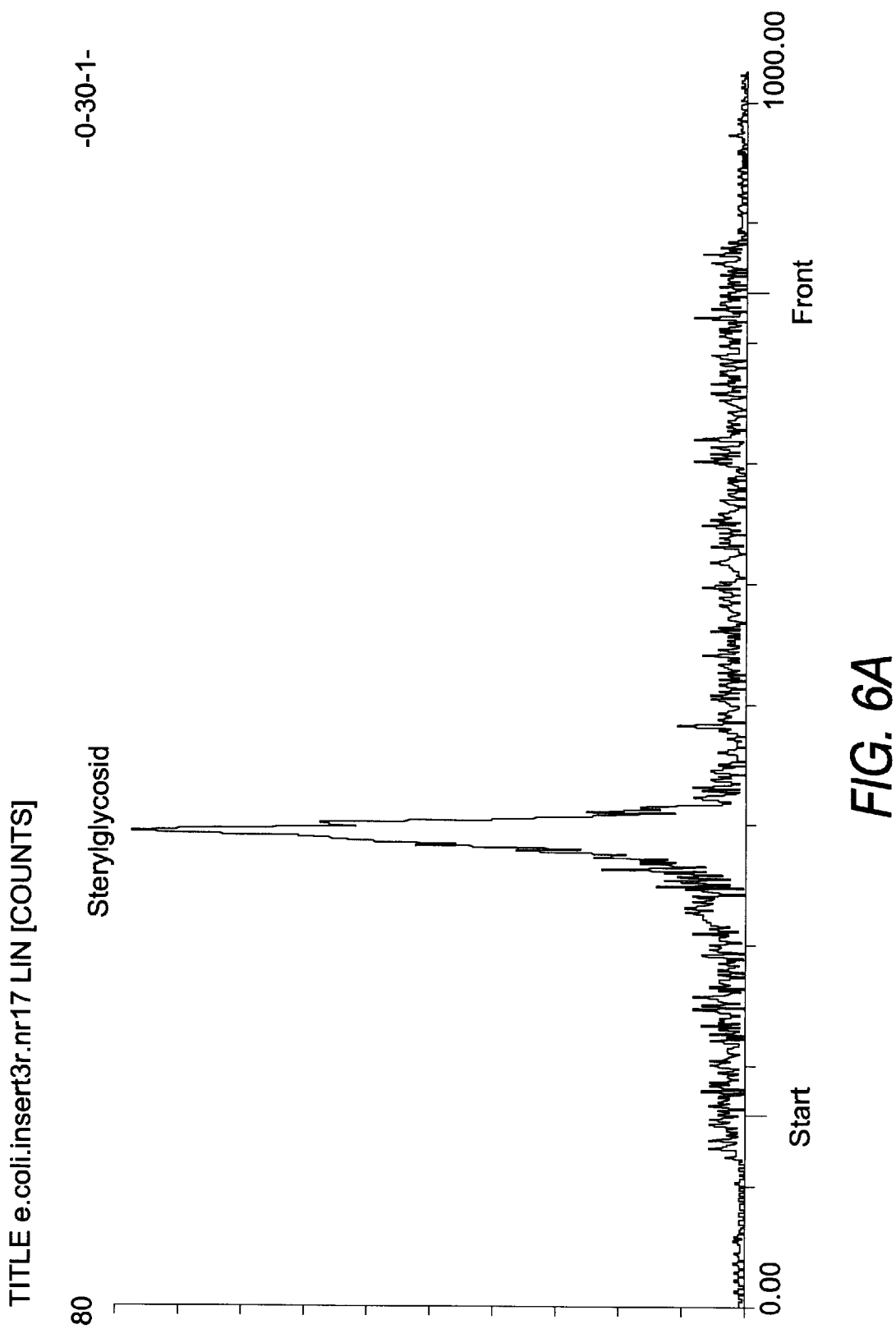

A.

```
  1: GGGTATGGGG ACGTGACGGT TGAAGAATCA TTGGATGGAG CGGATATACC ATATAGACCT
 61: CCTATGCAGA TTGTTATACT TATTGTGGGT ACAAGGGGAG ATGTTCAGCC ATTTGTTGCT
121: ATAGGAAAAC GCTTACAGGA TCATGGACAC CGTGTGAGAT TAGCCACTCA TGCCAACTTT
181: AAGGAGTTCG TACTGACAGC TGGGCTGGAG TTTTTTCCAC TTGGTGGAGA TCCAAAAATA
241: CTTGCTGAAT ACATGGTGAA GAATAAAGGG TTCCTGCCAT CAGGCCCATC AGAAATTCCT
301: ATTCAAAGAA AGCAGATGAG AGAAATTATA TTTTCCTTG
```

B.

```
  1: CCTCATGGAT ACATCTGGAG TCCTCATCTT GTTCCAAAAC CAAAAGACTG GGGCCCCAGG
 61: ATTGATGTTG TTGGATTCTG CTTCCTCGAT CTTGCTTCTG ATTACGAACC ACCTGAAGAA
121: CTTGTGAAAT GGCTTGAAGC TGGTGACAAG CCCATTTATG TTGGTTTCGG TAGCCTTCCA
181: GTTCAGGATC CAACAAAGAT GACCGAAACC ATCATCCAAG C
```

FIG. 2A

| FIG. 2A1 |
|---|
| FIG. 2A2 |

FIG. 2A1

```
  1:  CGAATCCTCC GGCTTCTCAT CCCGCATCTC GTCGGCCGCT CCTTTCCCCC TCCCCGCCGC
 61:  AACAGCAGGA GGTCCAGGCG GAGGAGTAAC CGCCGCGCCA AGTCTGGAAT CTCCGGGCCC
121:  ACCGGGCCAG CAGCGGGGGC GGTACAAATG GCCGATGCCG AGCCGACCGG CGGGGGAGGC
181:  AAGGGGCGCGG AAGATATAGG AGGAGCGGCG GAGGCGCACA GTCGCGACAG CCCTGCCTCG
241:  GCGGCACTAC CCACGGCGCC GTCGACGTCT TCCTCTTCCG CAGACAACGG GAACCTCCAT
301:  AGATCAAGCA CTATGCCAGG AGTGATCAAG GATGCTGAAA TAATTACTGA AACTACAGGA
361:  CCGTCGAATT TTGAAAGGTC GAAAACCGAG AGACGCCGGC AGAATAAATGA TCCTGCTAAA
421:  CAGTTATTGG ATGATAAGAT TTCCGTAAGG AAAAAGCTCA AAATGCTAAA CCGCATTGCT
481:  ACAGTGAGAG ATGATGGAAC TGTGGTTGTT GATGTACCAA GCTCTCTCTGA TTTGGCTCCA
541:  CTTGATGTTG GAGGAGAGGA TGGCTATGGT GATGTCACTG TTGAAGAATC ATTGGATGGA
601:  GCAGATATAC CATCCATACC TCCTATGCAG ATTGTTATAC TTATTGTGGG TACAAGGGGA
661:  GATGTTCAGC CATTTGTTGC TATAGCAAAA CGCTTACAGG ATTATGGACA CCGTGTGAGA
721:  TTAGCCACTC ATGCCAACTA TAAGGAGTTC GTACTGACAG CTGGGCTGGA GTTTTTCCCA
781:  CTTGGTGGAG ATCCAAAACT ACTTGCTGAA TACATGGTGA AGAATAAAGG GTTCCTGCCT
841:  TCAGGCCCAT CAGAAATTCC TATTCAAAGA AAGCAGATGA AAGAAATTAT ATTTCCTTG
901:  CTGCCTGCAT GCAAAGATCC TGATCCTGAC ACTGGCATTC CTTTCAAAGT GGATGCAATT
961:  ATTGCTAATC CACCGGCATA TGGACATACA CACGTGGCAG AGGCGCTAAA AGTACCCATT
```

```
1021: CATATATTCT TTACCATGCC ATGGACGCCA ACTAGTGAAT TTCCTCATCC TCTTTCTCGC
1081: GTGAAAACAT CAGCTGGATA TCGACTTTCT TACCAAATTG TTGACTCCAT GATTTGGCTT
1141: GGGATACGGG ATATGATAAA TGAATTCAGG AAAAAGAAGT TGAAGCTACG CCCAGTAACA
1201: TACCTAAGTG GTTCACAGGG TTCTGGAAGT GACATTCCTC ATGGATACAT CTGGAGTCCT
1261: CATCTTGTCC CAAAACCAAA AGACTGGGGC CCCAAGATTG ATGTTGTTGG ATTCTGCTTC
1321: CTCGATCTTG CTTCTGATTA CGAACCACCT GAAGAACTCG TGAAATGGCT TGAAGCTGGT
1381: GACAAGCCCA TTTATGTTGG TTTCGGTAGC CTTCCAGTTC AAGATCCAAC AAAGATGACT
1441: GAAACCATTA TCCAAGCACT TGAAATGACC GGACAGAGAG GTATTATTAA CAAAGGTTGG
1501: GGTGGCCTCG GAACCTTGGC AGAACCGAAA GATTCCATAT ATGTACTTGA CAACTGCCCT
1561: CATGACTGGC TTTTCCTGCA GTGTAAGGCA GTGGTGCATC ATGGTGGAGC TGGAACGACA
1621: GCTGCCGGCC TGAAAGCAGC GTGCCCTACA ACTATTGTAC CTTTCTTTGG CGACCAACAA
1681: TTCTGGGGAG ACCGGGGTGCA TGCTCGAGGG GTAGGGCCTG TGCCTATACC AGTTGAACAA
```

FIG. 2A2

FIG. 2B

Fortsetzung von Abbildung 2

```
1741: TTCAATTGC AGAAACTGGT TGATGCTATG AAGTTCATGT TGGAGCCAGA GGTAAAAGAA
1801: AAGGCTGTGG AGCTTGCCAA GGCCATGGAA TCTGAGGATG GTGTAACCGG TGCAGTTAGG
1861: GCATTCCTCA AACATCTGCC TTCTTCAAAA GAAGATGAAA ATTCACCCCC ACCTACGCCG
1921: CATGGTTTCC TAGAGTTCCT AGGCCCGGTA AGTAAATGTT TGGGGTGCTC TTAGGTGCTG
1981: ATTAGATGAA GGTATCACCA TTCCTCCCTG CAAAAGGAAG TGATTAAGGA AAAAAGGCTG
2041: TTGGGTGACT GAGCTATGCT GTTTTGTGCG ACAAGAATGT GGAAGCCCAT GTAAGAAGTT
2101: GAAGAACATC CAGCCAGGAG TGCGCGCTTT ATCGTTTCGC ATCGTTCGTT TGTTGGTTTT
2161: TGTTGTTGTG TAAAGAATAC TTGTCTCTGT AATTTGATAC ATCATTTTGG TGTGGTTGCA
2221: ACCTTGGTGT GCAGCAACCG ATGATCTCAC ATGTATGACC AGGCATCTGT GTATATGGAA
2281: AACTTTAAGA GGCAGATTAA AAAAAAAAAA AAAAAAA
```

FIG. 3A

A.

```
wa18e    : ------------GGGTATGGGGACGTGACGGTTGAAGAATCATTGGATGGA
HaSGT    : CTTGATGTTGGAGGAGAGGATGGCTATGGCTGATGTCACTGTTGAAGAATCATTGGATGGA
                     * ***    ********************** wa18e    : GCGGATATACCATATAGAGACCTCCTATGCAGATTGTTATACTTATTGTGGGTACAAGGGGA
HaSGT    : GCAGATATACCATCCATACCTCCTATGCAGATTGTTATACTTATTGTGGGTACAAGGGA
            ****** * ****************************************** wa18e    : GATGTTCAGCCATTTGTTGCTATAGAAAAACGCTTACAGGATCATGGACACCGTGTGAGA
HaSGT    : GATGTTCAGCCATTTGTTGCTATAGCAAAACGCTTACAGGATTATGGACACCGTGTGAGA
           ***********************  ***********  ************* wa18e    : TTAGCCACTCATGCCAACTTTAAGGAGTTCGTACTGACAGCTGGGCTGGAGTTTTTCCA
HaSGT    : TTAGCCACTCATGCCAACTATAAGGAGTTCGTACTGACAGCTGGGCTGGAGTTTTTCCCA
           ***************** ******************************** wa18e    : CTTGGTGGAGATCCAAAAATACTTGCTGAATACATGGTGAAGAATAAAGGGTTCCTGCCA
HaSGT    : CTTGGTGGAGATCCAAAAACTACTTGCTGAATACATGGTGAAGAATAAAGGGTTCCTGCCT
           *****************  *********************************** wa18e    : TCAGGCCCATCAGAAATTCCTATTCAAAGAAAGCAGATGAGAGAAATTATATTTCCTTG
HaSGT    : TCAGGCCCATCAGAAATTCCTATTCAAAGAAAGCAGATGAGAGAAATTATATTTCCTTG
           ************************************************************
```

FIG. 3B

```
wa19er   : ------------------------------------------CCTCATGGATACATCTGGAGTCCT
HaSGT    : TACCTAAGTGGTTCACAGGTTCTGGAAGTGACATTCCTCATGGATACATCTGGAGTCCT
           *                                          *********************** wa19er   : CATCTTGTTCCAAAAACCAAAAGACTGGGGCCCCAGGATTGATGTTGTTGGATTCTGCTTC
HaSGT    : CATCTTGTCCAAAAACCAAAAGACTGGGGCCCCAGGATTGATGTTGTTGGATTCTGCTTC
           ****** ************************************************ wa19er   : CTCGATCTTGCTTCTCTGATTACGAACCACCTGAAGAACTTGTGAAGCTTGAAGCTGGT
HaSGT    : CTCGATCTTGCTTCTCTGATTACGAACCACCTGAAGAACTCGTGAAATGGCTTGAAGCTGGT
           **************************************  *  *************** wa19er   : GACAAGCCCATTTATGTTGGTTCGGTAGCCTTCCAGTTCAGGATCCAACAAAGATGACC
HaSGT    : GACAAGCCCATTTATGTTGGTTCGGTAGCCTTCCAGTTCAAGATCCAACAACAAAGATGACT
           **************************************  **************  * wa19er   : GAAACCATCATCCAAGC---------------------------------------
HaSGT    : GAAACCATTATCCAAGCACTCTTGAAATGACCGGACAGAGAGGTATTATTAACAAAGGTTGG
           ******** *******
```

FIG. 4

```
  1: RILRLLIPHL VGRSFPPPRR NSRRSRRRSN RRAKSGISGP TGQTAGAVQM ADAEPTGVGG
 61: KGAEDIGGAA EAHSRDSPAS AALPTAPSTS SSSADNGNLH RSSTMPGVIK DAEIITETTG
121: PSNFERSKTE RRRQNNDPAK QLLDDKISVR KKLKMLNRIA TVRDDGTVVV DVPSSLDLAP
181: LDVGGEDAYG DVTVEESLDG ADIPSIPPMQ IVILIVGTRG DVQPFVAIAK RLQDYGHRVR
241: LATHANYKEF VLTAGLEFFP LGGDPKLLAK YMVKNKGFLP SGPSEIPIQR KQMKEIIFSL
301: LPACKDPDPD TGIPFKVDAI IANPPAYGHT HVAEAALKVPI HIFFTMPWTP TSEFPHPLSR
361: VKTSAGYRLS YQIVDSMIWL GIRDMINEFR KKKLKLRPVT YLSGSQGSGS DIPHGYIWSP
421: HLVPKPKDWG PKIDVVGFCF LDLASDYEPP EELVKWLEAG DKPIYVGFGS LPVQDPTKMT
481: ETIIQALEMT GQRGIINKGW GGLGTLAEPK DSIYVLDNCP HDWLFLQCKA VVHHGGAGTT
541: AAGLKAACPT TIVPFFGDQQ FWGDRVHARG VGPVPIPVEQ FNLQKLVDAM KFMLEPEVKE
601: KPVELAKPME SEDGVTGAVR AFLKHLPSSK EDENSPPPTP HGFLEFLGPV SKCLGCS
```

FIG. 5

```
N-TERMINUS :  -DVGGEDGYGDVTVEE-------
HaSGTP     : LDVGGEDAYGDVTVEESLDG
             ****** ********
```

FIG. 9

```
   1:  MPITQIISAS  DSEAGPKPSI  SLVPDKPSEP  ETSPRHHRLS  RSLSKFKRWR  GRSNSSLSMG
  61:  SSEQQELQDS  PNEARSDDDE  NGYNNDNADD  LAKSKYMMKS  IAGLLTTASV  YAGMNNAQEM
 121:  NVLSQVDSEE  SDSSDSFQEN  IGRNEVKSKK  ENLKTKSHPE  VPRLDKRKPT  LFDFSITREK
 181:  LSKDNVAKLR  QRFCLDEQEP  FLNDFPAWLL  KDVLVQGHIF  ITTKHFLFFA  YLPKNPRSVK
 241:  MSGNLNIRTK  LIRSTRYWCV  LKNHLFSMYT  SSTELYFPVL  TIDLREVQKI  ETQKHTLNGS
 301:  ATKTFKLYTD  ESTFKFNADS  EFSAKSWVNA  LKKEQFAAQN  SENNSISLKI  PLPNIIEIDD
 361:  QPIVNKALTL  RLRALESSQT  YAIDDFMFVF  MDGSGSQVKE  SLGEQLAILQ  KSGVNTLYYD
 421:  IPAKKSKSSF  GKETPATVEQ  KNNGEDSKYL  NVPTSAVPSS  ENGKKSRFRF  RERSNSWFRR
 481:  AKPLEDSQVE  DVEEIYKDAA  NDIDSSVHST  IHIHEQEDSQ  EQTVAWKPSH  LKNFAEMWAA
 541:  KPIHYRNKFI  PFQKDDTYLI  KETEEVSANE  RFRYHFKFNK  EKSLISTYYT  YLNRNVPVYG
 601:  KIYVSNDTVC  FRSLLPGSNT  YMVLPLVDVE  TCYKEKGFRF  GYFVLIVIH   GHEELFFEFS
 661:  TEVARDDIER  ILLKLLDNIY  ASSAEGSNIS  SASLGDVQHN  PDSAKLKLFE  DKINAEGFEV
 721:  PLMIDENPHY  KTSIKPNKSY  KFGLLTIGSR  GDVQPYIALG  KGLIKEGHQV  VIITHSEFRD
 781:  FVESHGIQFE  ELAGNPVELM  SLMVENESMN  VKMLREASSK  FRGWIDALLQ  TSWEVCNRRK
 841:  FDILIESPSA  MVGIHITEAL  QIPYFRAFTM  PWTRTRAYPH  AFIVPDQKRG  GNYNYLTHVL
 901:  FENVFWKGIS  GQVNKWRVET  LGLGKTNLFL  LQQNNVPFLY  NVSPTIFPPS  IDFSEWVRVT
 961:  GYWFLDDKST  FKPPAELQEF  ISEARSKGKK  LVYIGFGSIV  VSNAKEMTEA  LVEAVMEADV
1021:  YCILNKGWSE  RLGDKAAKKT  EVDLPRNILN  IGNVPHDWLF  PQVDAAVHHG  GSGTTGASLR
1081:  AGLPTVIKPF  FGDQFFYAGR  VEDIGVGIAL  KKLNAQTLAD  ALKVATTNKI  MKDRAGLIKK
1141:  KISKEDGIKT  AISAIYNELE  YARSVTLSRV  KTPRKKEENV  DATKLTPAET  TDEGWTMI
```

FIG. 11

```
Apcr
  1: GGGGGGATGT TCAGCCTTTT GTTGCAATAG CCAAACGGCT TCAGGACTAT GGCCATCGAG
 61: TTAGACTTGC AACTCATGCA AATTTTAAAG AGTTTGTTTT GACTGCTGGA TTAGAGTTTT
121: ATCCTCTAGG TGGAGATCCA AAAGTGCTCG CCGGTTATAT GGTTAAGAAC AAGGGCTTTT
181: TGCCATCAGG CCCTTCAGAG ATTCCAATTC AACGAAACCA AATGAAGGAC ATCATATATT
241: CTCTACTTCC AGCATGTAAA GAACCTGATC CAGATTCTGG GATTTCCTTT AAAGCTGATG
301: CAATTATTGC CAACCCTCCA GCGTATGGAC ATACCCATGT GGCAGAAGCA CTGAAGATAC
361: CGATTCACGT ATTTTTCACC ATGCCCTGGA CCCCCAC
```

FIG. 12

```
Kpcr
  1: CGCGGGGGGA TGTCCAGCCC TTTACTGCAA TTGGCAAGCG TCTGCAGGAT TTTGCCATC
 61: GAGTGAGGTT GGCGACCCAT TGGGGGTGAT GCAAATTTCA AAGAGTTTGT CTTGAGTGCT GGATTGGAAT
121: TCTATCCCCT TGGGGGTGAT CCAAAAAATTT TGGCTGGATA CATGGTAAAA AACAAAGGAT
181: TCTTACCTTC CGGACCTTCA GAAATCCCTG TTCAGAGAAA TCAGATGAAG GAGATTATAT
241: ACTCTCTACT TCCAGCCTGC AAAGAGCCTG ATATGGATAC AGGAGTTCCC TTCAAAGCAG
301: ATGCAATTAT TGCTAATCCC CCAGCATATG GCATGTACA TGTTGCAGAA GCATTGCAAA
361: TCCCAATTCA TATATTTTTC ACCATGCCCT GGACCCCCAC A
```

FIG. 13

```
Cpcr
  1:  GGTATTTCCG GACAAGTAAA TAAATGGAGA GTTGAGGAAT TAGATTTGCC AAAGACCAAT
 61:  TTATACAGGT TGCAACAGAC AAGGGTCCCC TTCTTGTATA ATGTTTCACC CGCTATATTA
121:  CCGCCATCTG TTGATTTTCC TGATTGGATT AAAGTAACTG GATACTGGTT TTTAGATGAA
181:  GGTTCTGGAG ATTACAAGCC ACCTGAAGAA CTTGTACAAT TTATGAAAAA AGCATCCCGT
241:  GACAAAAAGA AGATTGTTTA CATTGGATTT GGTTCTATTG TAGTGAAAGA TGCAAAATCC
301:  TTAACGAAAG CTGTGGTGTC TGCTGTGAGA AGAGCCGACG TTCGTTGTAT TTTAAACAAG
361:  GGTTGGTCTG ATCGATTGGA TAATAAAGAT AAAAATGAAA TTGAAATTGA GTTGCCACCG
421:  GAAATTACA ATTCTGGAAC TATACCTCAT GATTGGTTGT TTCCGCGTAT TGATGCTGCC
481:  GTGCACCATG CCGGCACCGG CACCAC
```

FIG. 14

A.

```
ApcrP
  1:  GDVQPFVAIA KRLQDYGHRV RLATHANFKE FVLTAGLEFY PLGGDPKVLA GYMVKNKGFL
 61:  PSGPSEIPIQ RNQMKDIIYS LLPACKEPDP DSGISFKADA IIANPPAYGH THVAEALKIP
121:  IHVFFTMPWT P
```

B.

```
ApcrP   : ---------- ---------- ---------- ---------- -GDVQPFVAIAKRLQDYGHRVR
RaSGTP  : LDVGGEDAYGDVTVEESLDGADIPSIPPMQIVILIVGTRGDVQPFVAIAKRLQDYGHRVR
                                                   ************************

ApcrP   : LATHANFKEFVLTAGLEFYPLGGDPKVLAGYMVKNKGFLPSGPSEIPIQRNQMKDIIYSL
RaSGTP  : LATHANYKEFVLTAGLEFFPLGGDPKLLAKYMVKNKGFLPSGPSEIPIQRKQMKEIIFSL
          ******.********** ******** * ******************.***.** **

ApcrP   : LPACKEPDPDSGISFKADAIIANPPAYGHTHVAEALKIPIHVFFTMPWTP----------
RaSGTP  : LPACKDPDPDTGIPFKVDAIIANPPAYGHTHVAEALKVPIHIFFTMPWTPTSEFPHPLSR
          *****.****. ** ** *************************.***.*********
```

FIG. 15

A.

```
  1:  RGDVQPFTAI GKRLQDFGHR VRLATHANFK EFVLSAGLEF YPLGGDPKIL AGYMVKNKGF
 61:  LPSGPSEIPV QRNQMKEIIY SLLPACKEPD MDTGVPFKAD AIIANPPAYG HVHVAEALQI
121:  PIHIFFTMPW TPT
```

B.

```
KpcrP  : ---------------------------------------RGDVQPFTAIGKRLQDFGHRVR
HaSGTP : LDVGGEDAYGDVTVEESLDGADIPSIPPMQIVILIVGTRGDVQPFVAIAKRLQDYGHRVR
         ******* ** ********.******

KpcrP  : LATHANFKEFVLSAGLEFYPLGGDPKILAGYMVKNKGFLPSGPSEIPVQRNQMKEIIYSL
HaSGTP : LATHANYKEFVLTAGLEFFPLGGDPKLLAKYMVKNKGFLPSGPSEIPIQRKQMKEIIFSL
         ******.***** *****.******* ** ****************:**:******.**

KpcrP  : LPACKEPDMDTGVPFKADAIIANPPAYGHVHVAEALQIPIHIFFTMPWTPT---------
HaSGTP : LPACKDPDPDTGIPFKVDAIIANPPAYGHTHVAEALKVPIHIFFTMPWTPTSEFPHPLSR
         *****:**:***:***.***********.******: *************
```

FIG. 16

A.

```
CpcrP   1:  GISGQVNKWR VEELDLPKTN LYRLQQTRVP FLYNVSPAIL PPSVDFPDWI KVTGYWFLDE
       61:  GSGDYKPPEE LVQFMKKASR DKKKIVYIGF GSIVVKDAKS LTKAVVSAVR RADVRCILNK
      121:  GWSDRLDNKD KNEIEIELPP EIYNSGTIPH DWLFPRIDAA VHHAGTGT
```

B.

```
CpcrP    :  ------GISGQVNKWRVEELDLPKTNLYRLQQTRVPFLYNVSPAILPPSVDFPDWIKVT
ScSGTP   :  FENVFWKGISGQVNKWRVETLGLGKTNLFLLQQNNVPFLYNVSPTIFPPSIDFSEWVRVT
            ****************  **  ****** * ****  ****************** *..**

CpcrP    :  GYWFLDEGSGDYKPPEELVQFMKKASRDKKKIVYIGFGSIVVKDAKSLTKAVVSAVRRAD
ScSGTP   :  GYWFLDDKST-FKPPAELQEFISEARSKGKKLVYIGFGSIVVSNAKEMTEALVEAVMEAD
            ******  *  .****.*.*.* * *.**.*********..*** * *.*.**. **

CpcrP    :  VRCILNKGWSDRLDNKDKNEIEIELPPEIYNSGTIPHDWLFPRIDAAVHHAGTGT------
ScSGTP   :  VYCILNKGWSERLGDKAAKTEVDLPRNILNIGNVPHDWLFPQVDAAVHHGGSGTTGASL
            * ********.** .*  . *  **..*...*.******..****** *.** 
```

FIG. 17.1

| FIG. 17.1A |
|---|
| FIG. 17.1B |

FIG. 17.1A

```
  1: ATTAATTCTC TCCTTCACTT TCTGGGATTC GAAACACGCA TACGCAAATT CGAGATACAC
 61: GAAGAAAGGA TCCAGATCGT TTTCTGCTGG TGGAGATAGA GAGAGAATCA CGATGCCGGA
121: AATATCGCCG GCTGAGCTCG CCAAGGTTTC TTCCTCGTCT TCTTCTTCTT CTTCCTCAAG
181: TTCCGGCAGA GCGTCGGTGA AAATCGAAGA GATTGAAGGC GGTGCTGCTG CTAGTGGCGT
241: CGTCATTGTT TCTGAAGAAC TTGAGACCAA TCCCAAAACT GTTGTTGCCT CCATTGCTGA
301: TGAAACTGTC GCTGAATCTT CAGGTACTGG CAATAAAAGC TTTTCTCGAG TATGGACAAT
361: GCCATTGGAG GGTTCATCGA GCAGTGATAG GGCTGAATCA TCATCAACAA ACCAACCTAG
421: GTTAGATAAA TCAAAGACTG AGAGGCAGCA AAAAGTTACT CACATTCTTG CTGAGGATGC
481: TGCTAAGATT TTCGATGACA AAATCTCTGC AGGGAAGAAG CTTAAATTGC TGAACCGTAT
541: AGCTACTGTG AAACATGATG GGACTGTTGA GTTTGAAGTT CCAGCAGATG CTATCCCTCA
601: ACCTATTGTT GTTGATCGTG GAGAATCGAA TCCCTCCTAT TGCGCTGATG AGTCTATTGA
661: CGGGGTTGAC CTTCAGTATA TCCCTCCTAT GCAAATTGTG ATGTTAATTG TTGGAACACG
721: TGGAGATGTT CAACCTTTTG TTGCAATAGC CAAACGGCTT CAGGACTATG GCCATCGAGT
781: TAGACTTGCA ACTCATGCAA ATTTTAAAGA GTTTGTTTTG ACTGCTGGAT TAGAGTTTTA
841: TCCTCTAGGT GGAGATCCAA AAGTGCTCGC CGGTTATATG GTTAAGAACA AGGGATTTTT
901: GCCATCAGGC CCTTCAGAGA TTCCAATTCA ACGAAACCAA ATGAAGGACA TCATATATTC
961: TCTACTTCCA GCATGTAAAG AACCTGATCC AGATTCTGGG ATTTCCTTTA AAGCTGATGC
```

```
1021: AATTATTGCC AACCCTCCAG CGTATGGACA TACCCATGTG GCAGAAGCAC TGAAGATACC
1081: GATTCACGTA TTTTTCACCA TGCCATGGAC ACCAACAAGT GAATTTCCAC ACCCATTGTC
1141: ACGTGTCAAA CAACCAGCAG GATACAGACT TTCATATCAA ATCGTCGATT CATTGATCTG
1201: GCTTGGAATA AGAGATATGG TAAATGACCT TAGGAAAAAG AAATTGAAAC TACGGCCTGT
1261: TACATATCTA AGTGGAACAC AAGGATCTGG ATCTAATATC CCACATGGAT ATATGTGGAG
1321: TCCTCACCTT GTACCAAAGC CAAAGACTG GGGCCCTCAA ATTGATGTAG TGGGATTTTG
1381: CTATCTTGAT CTTGCATCCA ACTATGAACC TCCTGCAGAG CTTGTGGAAT GGCTAGAAGC
1441: TGGTGACAAG CCCATATATA TCGGCTTTGG TAGTCTCCCT GTGCAAGAAC CAGAGAAAAT
1501: GACAGAAATC ATTGTGGAAG CACTTCAAAG AACTAAACAG AGAGGAATCA TCAACAAAGG
1561: TTGGGGTGGC CTTGGAAACT TGAAAGAACC GAAGGACTTT GTTACTTGT TGGATAATGT
1621: CCCACATGAC TGGCTATTCC CGAGATGCAA AGCTGTGGTT CATCATGGTG GTGCTGGAAC
1681: AACGGCTGCG GGTCTTAAAG CCTCGTGCCC AACTACAATC GTGCCTTTCT TTGGAGACCA
```

FIG. 17.1B

FIG. 17.2

```
1741:  ACCTTTTTGG GGAGAACGAG TGCATGCTAG AGGTGTTGGT CCTTCACCAA TCCCAGTGGA
1801:  TGAATTCTCA CTTCATAAGC TTGAAGATGC CATAAATTTC ATGCTCGACG ATAAGGTAAA
1861:  GAGCAGTGCA GAGACACTAG CAAAGGCGAT GAAGGACGAG GATGGTGTGG CTGGAGCCGT
1921:  GAAGGCCTTC TTTAAACATC TTCCAAGTGC AAAACAGAAT ATCTCGGATC CGATCCCAGA
1981:  ACCTTCTGGA TTTCTCTCTT TCAGGAAATG CTTTGGCTGT TCGTAACTTT CTTCTCTCCC
2041:  TCCAGAATCT CCTCTTTCT  CTTTTGTATT GTTGTCTCTT GTAATGTTTT TCTTCTTCGG
2101:  TTTGGCTAT  ACAACAACTT GCTTAGGAAA AGTTTTAACA TTTGTGAAGT GCTTGGGAAA
2161:  TTTGCTGTTC TAGGGGATGC ATATATTATA AAATTGTTAT AAGCAGCAAA AAAAAAAAAA
2221:  AAAAAAAATT CTGAAGATGT GCAGATTAGT GAACATTGTT GTATCGAGTT TTAATATTAT
2281:  GACATATTTT GTTTCAGTTT CTTGAGCTGC AACTTCAAAA AAAAAAAAAA AAAAAAAAAA
2341:  AAAAAAAAAA AAA
```

FIG. 18

```
  1: LILSFTFWDS KHAYANSRYT KKGSRSFSAG GDRERITMPE ISPAELAKVS SSSSSSSSSS
 61: SGRASVKIEE IEGGAAASGV VIVSEELETN PKTVVASIAD ETVAESSGTG NKSFSRVWTM
121: PLEGSSSSDR AESSSTNQPR LDKSKTERQQ KVTHILAEDA AKIFDDKISA GKKLKLLNRI
181: ATVKHDGTVE FEVPADAIPQ PIVVDRGESK NGVCADESID GVDLQYIPPM QIVMLIVGTR
241: GDVQPFVAIA KRLQDYGHRV RLATHANFKE FVLTAGLEFY PLGGDPKVLA GYMVKNKGFL
301: PSGPSEIPIQ RNQMKDIIYS LLPACKEPDP DSGISFKADA IIANPPAYGH THVAEALKIP
361: IHVFFTMPWT PTSEFPHPLS RVKQPAGYRL SYQIVDSLIW LGIRDMVNDL RKKKLKLRPV
421: TYLSGTQGSG SNIPHGYMWS PHLVPKPKDW GPQIDVVGFC YLDLASNYEP PAELVEWLEA
481: GDKPIYIGFG SLPVQEPEKM TEIIVEALQR TKQRGIINKG WGGLGNLKEP KDFVYLLDNV
541: PHDWLFPRCK AVVHHGGAGT TAAGLKASCP TTIVPFFGDQ PFWGERVHAR GVGPSPIPVD
601: EFSLHKLEDA INFMLDDKVK SSAETLAKAM KDEDGVAGAV KAFFKHLPSA KQNISDPIPE
661: PSGFLSFRKC FGCS
```

FIG. 19

| FIG. 19A |
|----------|
| FIG. 19B |

FIG. 19A

```
AtSGTP  : LILSFTFWDSKHAYANSRYTKKGSRSFSAGGDRERITMPEISPAELAKVSSSSSSSSSS
HaSGTP  : ----------------------------RILRLLIPHLVGRSFPPPRRNSRRSRRRS
                                       *  .*    .              *

AtSGTP  : SGRASVKIEEIEGGAAASGVVIVSEEL---------ETNPKTVVASIADETVAE-
HaSGTP  : NRRAKSGISGPTGQTAGAVQMADAEPTGVGGKGAEDIGAAEAHSRDSPASAALPTAPST
           ** .*     .              *              **      *

AtSGTP  : -SSGTGNKSFSRVWTMPLEGSSSSDRAESSSTNQPRLDKSKTERQQKVTHILAEDAAKIF
HaSGTP  : SSSSADNGNLHRSSTMP--GVIKDAEIITETTGPSNFERSKTERR---RQNNDPAKQLL
          **       *        * *         ...*****           .    .

AtSGTP  : DDKISAGKKLKLLNRIATVKHDGTVEFEVPADAIPQPIVVDRGESKNGVCADESIDGVDL
HaSGTP  : DDKISVRKKLKMLNRIATVRDDGTVVVDVPSSLDLAPLDVGGEDAYGDVTVEESLDGADI
          ***** *** *******  ****  *   *    *        *        *****  *

AtSGTP  : QYIPPMQIVMLIVGTRGDVQPFVAIAKRLQDYGHRVRLATHANFKEFVLTAGLEFYPLGG
HaSGTP  : PSIPPMQIVILIVGTRGDVQPFVAIAKRLQDYGHRVRLATHANYKEFVLTAGLEFFPLGG
           ***** ********************************** ********** ****

AtSGTP  : DPKVLAGYMVKNKGFLPSGPSEIPIQRNQMKDIIYSLLPACKEPDPDSGISFKADAIIAN
HaSGTP  : DPKLLAKYMVKNKGFLPSGPSEIPIQRKQMKEIIFSLLPACKDPDPDTGIPFKVDAIIAN
          *** ** ******************** ***  * ****** ****  ** ** *****
```

```
AtSGTP  : PPAYGHTHVAEALKIPIHVFFTMPWTPTSEFPHPLSRVKQPAGYRLSYQIVDSLIWLGIR
HaSGTP  : PPAYGHTHVAEALKVPIHIFFTMPWTPTSEFPHPLSRVKTSAGYRLSYQIVDSMIWLGIR
          **************:**::************** ::*********** ***:*****

AtSGTP  : DMVNDLRKKKLKLRPVTYLSGTQGSGSNIPHGYMWSPHLVPKPKDWGPQIDVVGFCYLDL
HaSGTP  : DMINEFRKKKLKLRPVTYLSGSQGSGSDIPHGYIWSPHLVPKPKDWGPKIDVVGFCFLDL
          **:*: ***************:*****:*****:************:********:***

AtSGTP  : ASNYEPPAELVEWLEAGDKPIYIGFGSLPVQEPEKMTEIIVEALQRTKQRGIINKGWGGL
HaSGTP  : ASDYEPPEELVKWLEAGDKPIYVGFGSLPVQDPTKMTETIIQALEMTGQRGIINKGWGGL
          **.****:***:**********:********:*.****.**:** .*************

AtSGTP  : GNLKEPKDFVYLLDNVPHDWLFPRCKAVVHHGGAGTTAAGLKASCPTTIVPFFGDQPFWG
HaSGTP  : GTLAEPKDSIYVLDNCPHDWLFLQCKAVVHHGGAGTTAAGLKAACPTTIVPFFGDQQFWG
          *.*.****.:*:***.****** :******************:************:***

AtSGTP  : ERVHARGVGPSPIPVDEFSLHKLEDAINFMLDDKVKSSAETLAKAMKDEDGVAGAVKAFF
HaSGTP  : DRVHARGVGPVPIPVEQFNLQKLVDAMKFMLEPEVKEKPVELAKPMESEDGVTGAVRAFL
          :********.****::*.*:**.**::***:.:**.. .****.**.*****:***:**.

AtSGTP  : KHLPSAKQNISDPIPEPSGFLSFR---KCFGCS
HaSGTP  : KHLPSSKEDENSPPPTPHGFLEFLGPVSKCLGCS
          *****:*::::.* :*.***.*     ***:***
```

*FIG. 19B*

FIG. 21

```
  1:  IPPMQIVILI VGTRGDVQPF VAIAKRLQDY GHRVRLATHA NYKEFVLTAG LEFFPLGGDP
 61:  KLLAKYMVKN KGFLPSGPSE IPIQRKQMKE IIFSLLPACK DPDPDTGIPF KVDAIIANPP
121:  AYGHTHVAEA LKVPIHIFFT MPWTPTSEFP HPLSRVKTSA GYRLSYQIVD SMIWLGIRDM
181:  INEFRKKKLK LRPVTYLSGS QGSGSDIPHG YIWSPHLVPK PKDWGPKIDV VGFCFLDLAS
241:  DYEPPEELVK WLEAGDKPIY VGFGSLPVQD PTKMTETIIQ ALEMTGQRGI INKGWGGLGT
301:  LAEPKDSIYV LDNCPHDWLF LQCKAVVHHG GAGTTAAGLK AACPTTIVPF FGDQQFWGDR
361:  VHARGVGPVP IPVEQFNLQK LVDAMKFMLE PEVKEKPVEL AKPMESEDGV TGAVRAFLKH
421:  LPSSKEDENS PPPTPHGFLE FLGPVSKCLG CS
```

FIG. 22

```
  1:  IPPMQIVMLI VGTRGDVQPF VAIAKRLQDY GHRVRLATHA NFKEFVLTAG LEFYPLGGDP
 61:  KVLAGYMVKN KGFLPSGPSE IPIQRNQMKD IIYSLLPACK EPDPDSGISF KADAIIANPP
121:  AYGHTHVAEA LKIPIHVFFT MPWTPTSEFP HPLSRVKQPA GYRLSYQIVD SLIWLGIRDM
181:  VNDLRKKKLK LRPVTYLSGT QGSGSNIPHG YMWSPHLVPK PKDWGPQIDV VGFCYLDLAS
241:  NYEPPAELVE WLEAGDKPIY IGFGSLPVQE PEKMTEIIVE ALQRTKQRGI INKGWGGLGN
301:  LKEPKDFVYL LDNVPHDWLF PRCKAVVHHG GAGTTAAGLK ASCPTTIVPF FGDQPFWGER
361:  VHARGVGPSP IPVDEFSLHK LEDAINFMLD DKVKSSAETL AKAMKDEDGV AGAVKAFFKH
421:  LPSAKQNISD PIPEPSGFLS FRKCFGCS
```

FIG. 23

```
  1:  ENPHYKTSIK PNKSYKFGLL TIGSRGDVQP YIALGKGLIK EGHQVVIITH SEFRDFVESH
 61:  GIQFEEIAGN PVELMSLMVE NESMNVKMLR EASSKFRGWI DALLQTSWEV CNRRKFDILI
121:  ESPSAMVGIH ITEALQIPYF RAFTMPWTRT RAYPHAFIVP DQKRGGNYNY LTHVLFENVF
181:  WKGISGQVNK WRVETLGLGK TNLFLLQQNN VPFLYNVSPT IFPPSIDFSE WVRVTGYWFL
241:  DDKSTFKPPA ELQEFISEAR SKGKKLVYIG FGSIVVSNAK EMTEALVEAV MEADVYCILN
301:  KGWSERLGDK AAKKTEVDLP RNILNIGNVP HDWLFPQVDA AVHHGGSGTT GASLRAGLPT
361:  VIKPFFGDQF FYAGRVEDIG VGIALKKLNA QTLADALKVA TTNKIMKDRA GLIKKKISKE
421:  DGIKTAISAI YNELEYARSV TLSRVKTPRK KEENVDATKL TPAETTDEGW TMI
```

STEROL GLYCOSYL TRANSFERASES

The invention relates to DNA sequences coding for sterol glycosyl transferases as well as the use thereof to modify the content and/or the structure of sterol glycosides and/or their synthetic secondary products in transgenic organisms. Sterol glycosides and the biosynthetic secondary products steryl oligoglycosides and acylated sterol glycosides are natural substances found in plants as well as in some fungi and bacteria. For these substances and their secondary products a variety of physiological effects have been described such as for example inhibition of the vascular permeability, anti tumor activity antiphlogistic and haemostatic effect (Okuyama, E and Yamazaki, M (1983) Yakugaku Zasshi 103: 43 ff; Normura, T.; Watanabe, M.; Inoue, K. and Ohata, K. (1978) Japan J. Pharmacol. 28, Suppl. 110 P; Miles, D. H.; Stagg, D. D. and Parish, E. J. (1979) J. Nat. Prod: 42: 700 ff; King, M. L.; Ling, H. C.; Wang, C. T. and Su, M. (1979) J. Nat. Prod. 42: 701 ff.; Seki, J.; Okita, A.; Watanabe, M.; Nakagawa, T.; Honda, K.; Tatewaki, N. and Sugiyama, M. (1985) J. Pharm. Sci. 74: 1259-1264), which suggest an application as therapeutically effective substances for human beings. So far only β-sitosterol-β-D-glycoside, which is isolated from plants, can be bought as a medication for the treatment of prostrade hyperplasis (for example as bloom oil capsules, Hoyer Ltd., Neuss). A disadvantage of the substances lies in the fact that they exist in the organisms in only relatively small amounts and that they have to be extracted and purified by highly expensive methods. Furthermore, some of the organisms, which contain these substances are human-pathogenic and can only be cultivated with a high expenditure which makes their potential use as medication, detergents, emulgators, as basic material for synthetic materials and for the production of liposomes when needed in large amounts and of higher purity, fairly inapplicable at this point in time.

The enzymatic synthesis of sterol glycosides in the organisms of sugar nucleotides and sterols with a free OH-group is catalyzed by the sterol glycosyl transferases (in short: sterol glycosyl transferases) which are dependent on sugar nucleotides. These enzymes can be partly isolated and purified from the organisms, but are not available for economic use in sufficient quantities and qualities.

The activity of these enzymes can be proven with special in vitro enzyme detection systems. Furthermore, in one particular case a sterol glycosyl transferases from oat could be purified to the point of homogeneity. (Warnecke and Heinz, 1994) so far, however, no gene or any other nucleic acids has been known which codes a sterol glycosyl transferases.

Furthermore some nucleic acid sequences are known, which are similar to the sequence described in this patent application. In no case however, a sterol glycosyl transferase activity of the matching transcription product has been shown for the same or has even been discussed. Such nucleic acid sequences can only be used to manipulate the content and/or the composition of sterol glycosides and secondary products in certain organisms and thereby positively modify relevant characteristics of such organisms. That way cultivated plants can be produced with a better tolerance or resistance against hazardous environmental influences such as saline soil, drought, cold and freeze. Also micro organisms as for example, baker and brewing yeast can be improved with regard to ethanol and temperature tolerance.

In addition to the reaction product sterol glycoside, the enzyme itself can be of economical use when it can be produced purely and in large quantity by the application of genetic engineering. An example for this is the use of cholesterol quantification.

Furthermore the sterol glycosyl transferases—and the respectively coding DNA sequences—based on their similarity of sollanidine with sterols—can also be used as enzymes or the supply of such enzymes, which are responsible for the synthesis of solanine in solacene. This enables the production of plants, which are modified by genetic engineering, with low solanine or which are solanie free. By choosing the suitable methods such a reduction can be limited to certain parts of the plant or certain stages of development.

It is the task of the present invention to provide nucleic acid fragments with which transgenic organisms can be produced, which have improved economically relevant characteristics or with which in vivo or in vitro sterol glycosides and their secondary products can be produced a) in larger quantities than in the original organisms; or b) produced from organisms which are easier and simpler to cultivate than those in which these substances occur naturally; or c) which are of a new structure and which have more favorable characteristics.

A method has been invented to control the synthesis of sterol glycosides and their secondary products. For this, nucleic acid fragments are provided which code sterol glycosyl transferases to produce chimerical genes. These chimerical genes can be used to transform cell cultures, plants, animals or micro organisms and thereby modify their sterol glycoside synthesis.

The invention relates to (1) an isolated DNA fragment or recombinant DNA construct containing at least one part of a sequence coding sterol glycosyl transferases or sterol glycosyl transferases in the strictest sense;

(2) a protein which derives from one nucleic acid sequence illustrated in FIGS. 1–3 or 11–22;

(3) plasmides, viruses or other vectors, which contain nucleic acid sequences as defined in (1);

(4) genomic clones containing genes or parts of genes which code a sequence as defined in (1);

(5) a chimerical gene which is able to modify the content of sterol glycosyl transferase or sterol glycosyl transferases in the strictest sense, especially sterol glycosyl transferase or sterol glycosyl transferases in the strictest sense;

(6) transformed cells, transformed micro organisms, plants or parts of plants containing a chimerical gene as defined in (5);

(7) a method for producing sterol glycoside entailing the cultivation of the transformed organisms defined in (6);

(8) the sterol glycosides or their secondary products obtained from the method defined in (7);

(9) a DNA fragment obtained according to one of the following methods or parts thereof:

a) use of one of nucleic acid sequences illustrated in FIGS. 1–3 or 11–13 or 17 as hybridization sample;

b) use of the amino acid sequences illustrated in FIGS. 4, 5, 14–16, 18, 19, 21 or 22 for the synthesis of peptides or proteins which serve the obtaining of antisera; or c)
 i) comparing of the nucleotide sequences illustrated in FIGS. 1–3, 11–13 or 17 or the amino acid sequences derived thereof illustrated in FIGS. 4, 5,

14–16, 18, 19, 21 or 22 with each other or with already known nucleotide sequences or amino acid sequences derived thereof, ii) deriving and syntethisingsizing of suitable specific oligonucleotides from similar areas of these sequences, and iii) use of these oligonucleotides to produce nucleic acids coding for sterol glycosyl transferases or sterol glycosyl transferases in the strictest sense especially for sterol glycosyl transferases or sterol glycosyl transferases in the strictest sense or parts thereof with the help of a sequence depending protocol, especially the PCR method.

(10) a chimerical gene containing a DNA fragment defined in (9) and which is able to modify the content of sterol glycosyl transferase or sterol glycosyl transferase in the strictest sense especially sterol glycosyl transferase or sterol glycosyl transferase in the strictest sense in a transformed cell;

(11) transformed cells containing a chimerical gene as defined in (10);

(12) organisms, especially micro organisms such as bacteria and yeast whose gene or genes coding sterol glycosyl transferases or sterol glycosyl transferases in the strictest sense, especially sterol glycosyl transferases or sterol glycosyl transferases in the strictest sense, are deleted or interrupted by transformation with suitable chimerical genes.

(13) sterol glycosyl transferases or sterol glycosyl transferases in the strictest sense, especially sterol glycosyl transferases or sterol glycosyl transferases in the strictest sense or parts thereof or fusion proteins with the already mentioned transferases which can be obtained from organisms as defined in (6) or (11) and

(14) antisera or products made of antisera, antibodies and parts thereof which are directed to a protein as defined in (13).

The nucleic acid fragments coding for sterol glycosyl transferases (FIGS. 2, 17) could be isolated from *avena sativa* and *arabidopsis thalliana*. The amino acid sequences derived from these nucleic acid sequences have a surprisingly low similarity to the already known sequences of steroid hormone glucoronosyl transferases. Therefore, it is quite surprising that we were able to isolate completely new nucleic acid fragments with our methods. So far it has not been possible to identify another nucleic acid fragment, which codes for sterol glycosyl transferases. The isolated eucaryotic nucleic acid fragments are characterized by the fact that they are surprisingly suited, fitted with respective control sequences, for effecting the synthesis of enzymatically active sterol glycosyl transferases in eucaryotic as well as in procaryotic organisms and within the same without the typically eucaryotic processing and modification.

The invention also relates to isolated nucleic acid fragments whose derived amino acid sequences have defined similarities to the derived amino acid sequences in FIG. 12 or 13. The invention also relates to all plasmides, viruses and other vectors which contain these isolated nucleic acid fragments or parts thereof.

The amino acid sequence illustrated in FIGS. 4 and 18 have remarkable similarities with the derived amino acid sequence of a genomic DNA piece from *s. cerevisiae* (see FIG. 9). Thereby dealing with the chromosome XII cosmid 9470 (gene bank no. gb U17246). The similarity is related to the 3'-range of the open reading structure of bp 32961–36557 (gene L9470.23). For this putative gene no function has been known so far. Several parts of this gene are provided with suitable control sequences and were able to prove sterol glycosyl transferases activities in cell homogenates of the transgenic cells after transformation of *E. coli* with this chimerical gene.

Furthermore, the invention also relates to the use of nucleic acid sequences of FIGS. 1–3, 11–13 and 17 or the amino acid sequence derived thereof for the isolation of genes or cDNAs coding for other sterol glycosyl transferases. This relates to the use of sequences or parts thereof as hybridization samples, use of antibodies against a polypeptide for example, which is coded by the nucleic acid fragments or derives thereof respectively. Furthermore the derivation of oligonucleotides and the use thereof in the PCR method from the nucleotide- or amino acid sequences is also effected by the comparison with other sequences.

The invention relates to all plasmides, viruses and other vectors containing the nucleic acid sequences from the FIGS. 1–3, 11–13, 17 or parts thereof or the yeast gene L9470.23 or parts thereof or nucleic acid fragments or parts thereof which were isolated according to the methods described in the foregoing paragraph and which are suited for expression of sterol glycosyl transferases in transformed cells. Patent is also claimed for all organisms (micro organisms, animals, plants, parts thereof, cell cultures) which contain these chimerical genes or the products and extracts thereof, if the substantial composition of these organisms has been modified by these chimerical genes.

The illustration of nucleic acids in the illustrations is always from 5'-end to the 3' end the one of proteins from amino terminus to carboxy terminus. The amino acids are nominated in the one-letter code. The illustrations serve the explanation of the present invention. They illustrate:

FIG. 1: DNA partial sequences of an about 800 bp long DNA fragment which was obtained via the PCR method from oat cDNA (see example 3.) A. 5'-terminal sequence wa18e (SEQ ID NO: 1). B. 3' terminal sequence w119er (SEQ ID NO: 2).

FIG. 2: FIGS. 2*a* and 2*b* encompass the DNA-sequence of the nucleic acid sequences HaSTG (SEQ ID NO: 3), which was isolated from a cDNA expression bank from oat seedlings. It has a length of 2317 basepairs (bp) and contains an open reading structure from position 1 to 1971. Starting— and termination codon are at positions 148–150 respectively 1972–1974.

FIG. 3: Comparisons of the DNA partial sequences wa18e (SEQ ID NO: 1) and wa 19er (SEQ ID NO: 2) of the 800 bp long DNA fragment (FIG. 1) with the sequence of the oat clone HaSTG (FIG. 2). The comparison was performed with the help of the program CLUSTAL (Higgins and Sharp, 1988, Gene 73, 237–244). A. Comparison between wa18e (SEQ ID NO: 1) and HaSTG (SEQ ID NO: 5). B. Comparison between wa19er (SEQ ID NO: 2) and HaSTG (SEQ ID NO: 6). The positions marked with * refer to identical bases.

FIG. 4: Amino acid sequence HaSGTP (SEQ ID NO: 7) in the one-letter code deriving from the DNA sequence of the nucleic acid fragment HaSGT coding for a sterol glycosyl transferase with a molecular mass of 71 kD.

FIG. 5: Comparison of the N-terminal amino acid sequence of the purified enzyme (N-TERMINUS) (SEQ ID NO: 8) with the amino acid sequence HaSGT (SEQ ID NO: 9) deriving from the oat clone HaSGT. The comparison was performed with the help of the program CLUSTAL (Higgins and Sharp, 1988, Gene 73, 237–244). The identical amino acids—marked with * refer to non-existing or unknown amino acids.

Figure 6B:
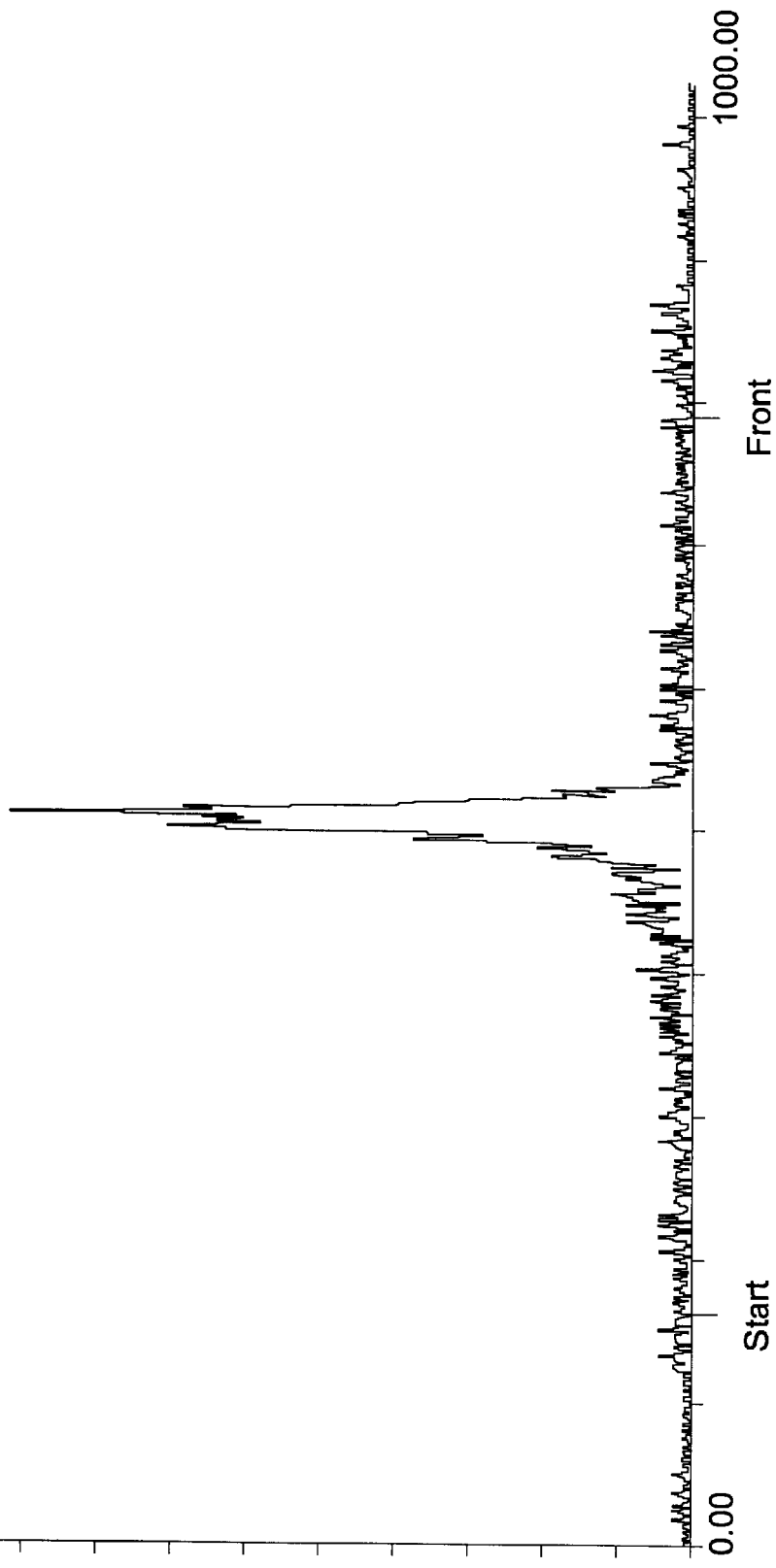

FIG. 6: Thin layer chromatographic analysis of radioactive products of in vitro enzyme assays which were performed with cell free homogenates of transformed *E. coli* cells (example 5.) The organic phases were transferred to silica gel 60 plates (Merck, Darmstadt), which were developed with the solvent chloroform:methanol 85:15 (A) respectively chloroform:methanol:ammonia (25%) 65:35:5 (B). The Rf-values of the radioactive, lipophile reaction procusts were determined with a Berthold-TLC-analyser and were compared with authentic standards, which were detected with α-naphtol sulfuric acid. Only one product was to be found only which could be identified as sterylglucoside. The Rf-value of the sterylglucoside derives from the usual value with this solvent in this case with regard to A because the solvent was not freshly produced and a modification of the composition occurred due to evaporation. A. *e.coli* cells were transformed with the plasmid pBS-ATG (example 5). B. The *e. coli* cells were transformed with the plasmid pBS-HRP (example 5).

Figure 7:
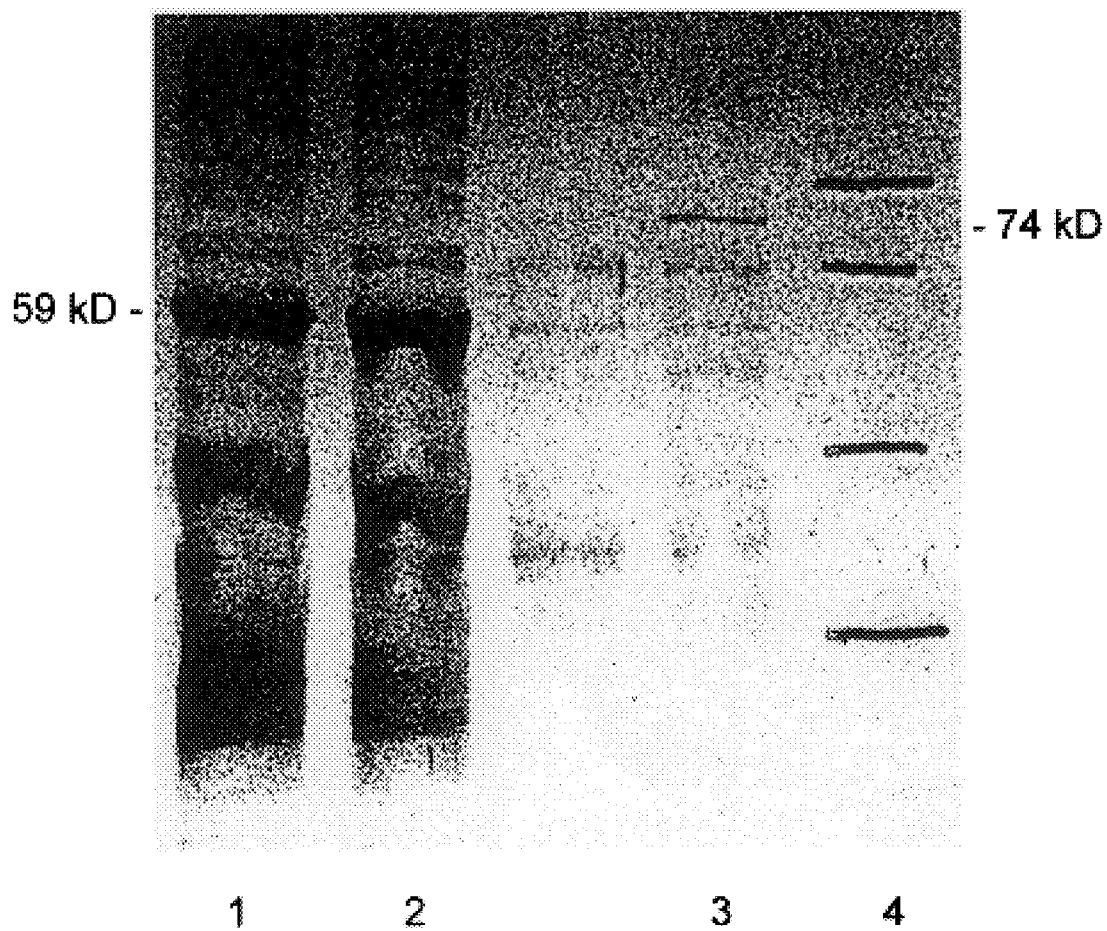

FIG. 7: Western-blot of recombinant sterol glycosyl transferases. 40 μg protein of *e. coli* cells, which exprime several parts of the oat clone HaSGT was subjected to a SDS-polyacrylamide gel electrophoresis and after that transferred to a hydrophobe membrane. The immuno tint was performed with an antiserum against the sterol glycosyel transferase purified from oat. Track 1 and 2: protein of *e. coli* cells which were transformed with the plasmid pBS-HRP. Track 3: protein of *e. coli* cells which were transformed with the plasmid pBS-HATG. Track 4: standard proteins with the molecular masses of 31, 45, 66 and 97 kD. The proteins were colored with ponceau red, the standard proteins marked with a pen and colored again.

Figure 8:
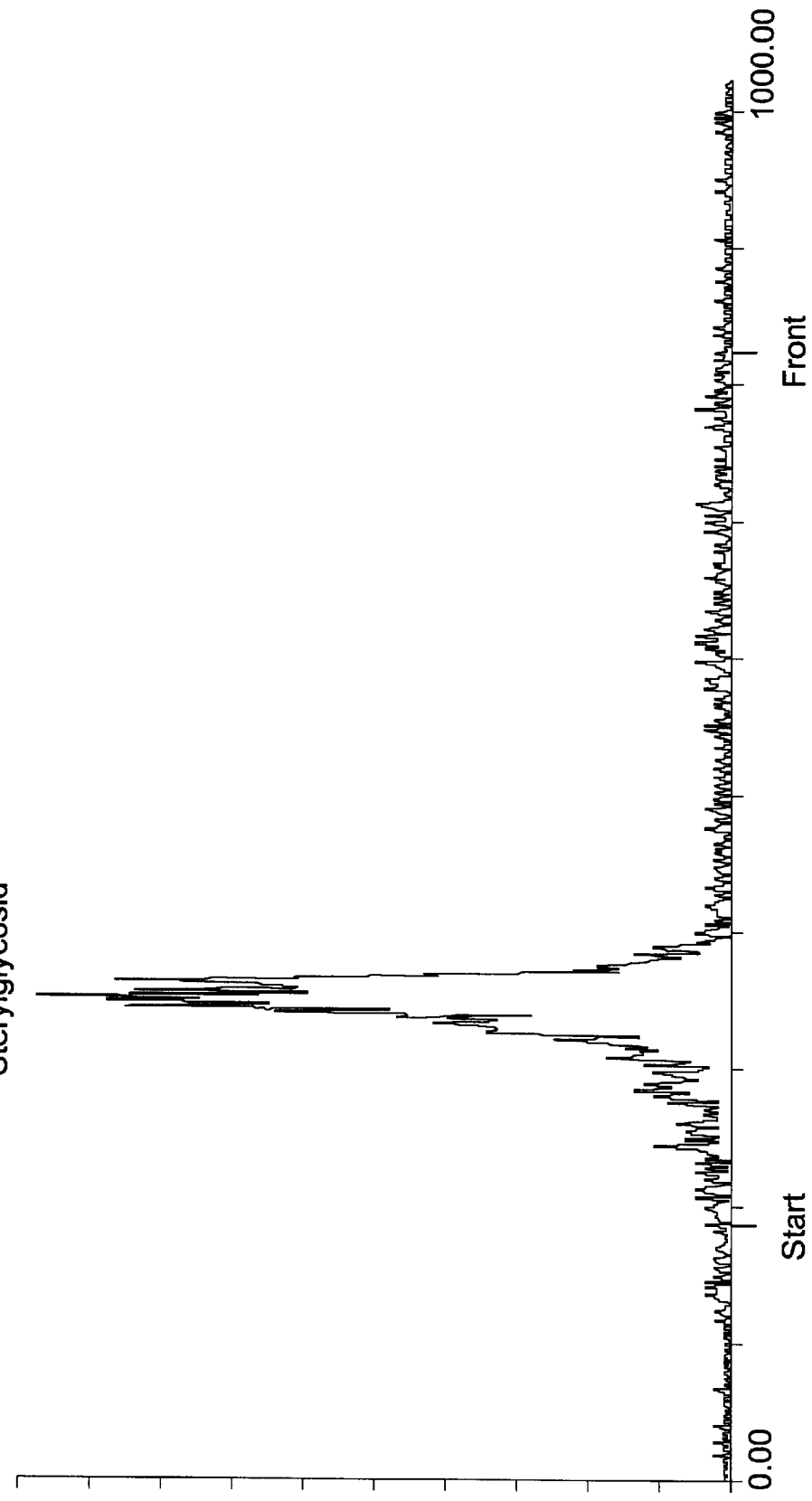

FIG. 8: Thin layer chromatographic analysis of radioactive products of in vitro enzyme assays which were performed with cell free homogenates of *s. cerevisiae* cells (example 6) transformed with the plasmid pGALHAM1. The organic phase was transferred to silica gel 60 plates (Merck, Darmstadt), which were developed with the solvent chloroform:methanol 85:15. The Rf-values of the radioactive, lipophile reaction product were determined with a Berthold-TLC analyser and were compared with authentic standards, which were detected with α-naphtol sulfuric acid. Only one product was to be found which could be identified as sterylglucoside.

FIG. 9: Amino acid sequence in the one-letter code deriving from the DNA sequence of the *s. cerevisiae* gene L9470.23 (SEQ ID NO: 10). The amino acids with which the second paragraph of the fusion protein begins, for which the plasmids of the clonings 1–4 code (example 7), are marked.

Figure 10A:
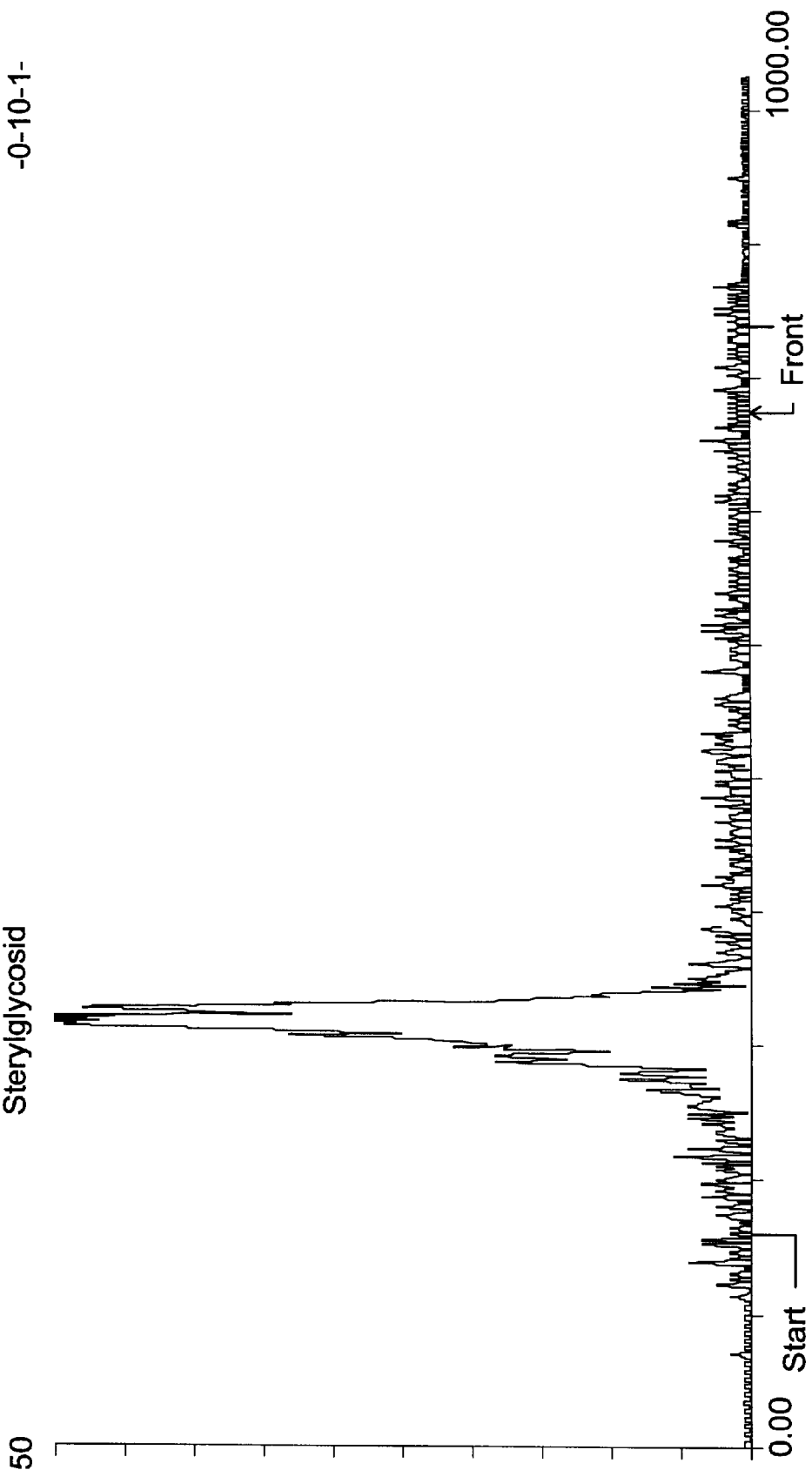
Figure 10B:
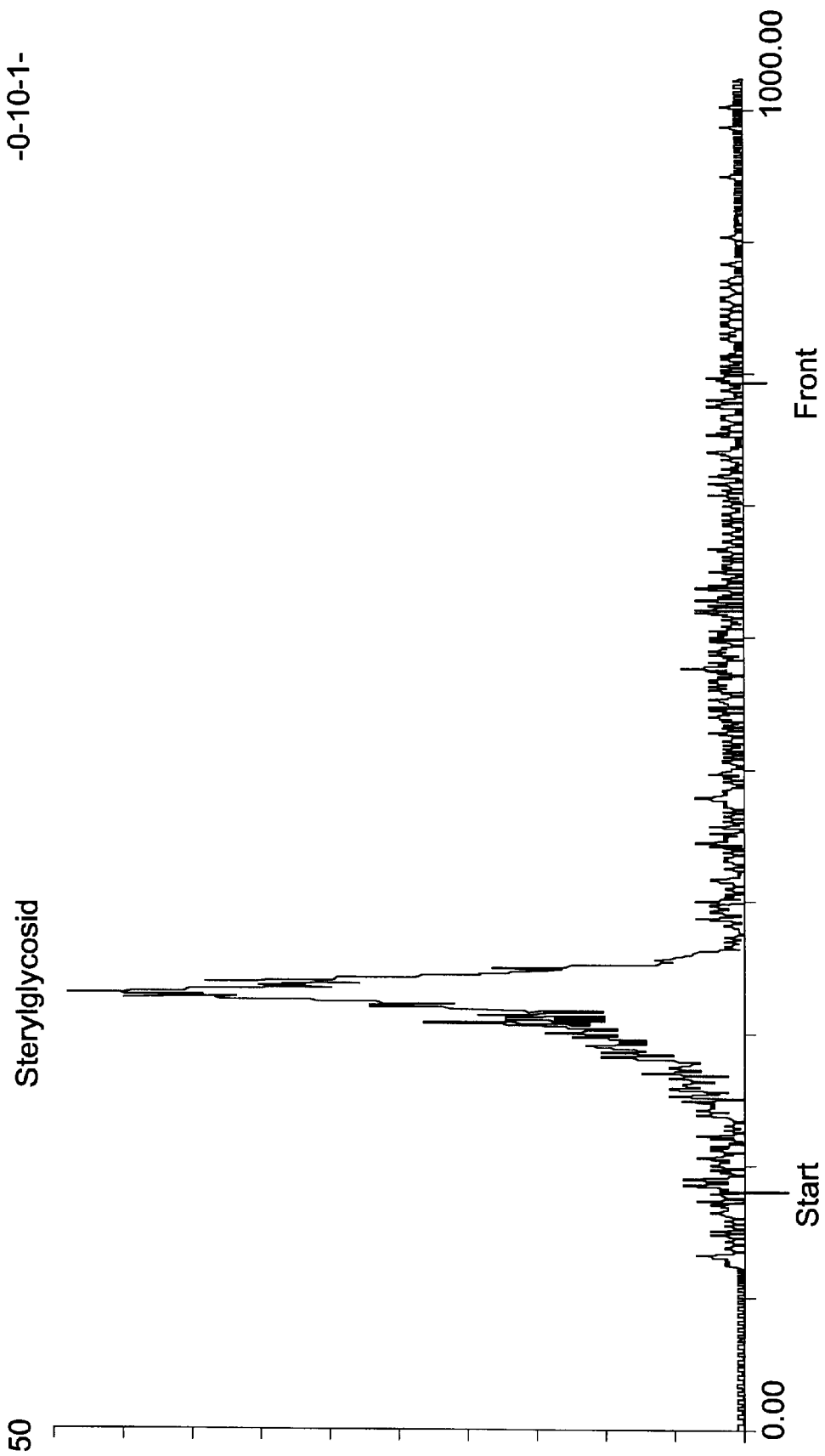

FIG. 10: Thin layer chromatographic analysis of radioactive products of in vitro enzyme assays which were performed with cell free homogenates of transformed *s. cerevisiae* cells (see example 7).

The organic phases were transferred to silica gel 60 plates (Merck, Darmstadt), which were developed with the solvent chloroform:methanol 85:15. The Rf-values of the radioactive, lipophile reaction product were determined with a Berthold-TLC analyser and were compared with authentic standards, which were detected with α-naphtol sulfuric acid. Only one product was to be found which could be identified as sterylglucoside. A. The *s. cerevisiae* cells were transformed with the plasmid of the cloning 2. B. The *s. cerevisiae* cells were transformed with the plasmid of the cloning 4 (example 5).

FIG. 11: DNA sequence of the DNA fragment Apcr (SEQ ID NO: 11) which was isolated with the PCR method from arabidopsis thalliana (example 8.).

FIG. 12: DNA sequence of the DNA fragment Kpcr (SEQ ID NO: 12) which was isolated with the PCR method from solanum tuberosum (example 8.).

FIG. 13: DNA partial sequence of the DNA fragment Cpcr (SEQ ID NO: 13) which was isolated with the PCR method from *candida albicans* (example 8.).

FIG. 14: A. Amino acid sequence ApcrP (SEQ ID NO: 14) in the one-letter code deriving from the DNA sequence of the DNA fragment Apcr. B. Comparison of the amino acid sequence ApcrP (SEQ ID NO: 14) with the oat sequence HaSGTP (SEQ ID NO: 15). The comparison was performed with the help of the program CLUSTAL (Higgins and Sharp, 1988, genes 73, 237–244). The * mark identical amino acids.

FIG. 15: A. Amino acid sequence KpcrP (SEQ ID NO: 16) in the one-letter code deriving from the DNA sequence of the DNA fragment Kpcr. B. Comparison of the amino acid sequence KpcrP (SEQ ID NO: 16) with the oat sequence HaSGTP. The comparison was performed with the help of the program CLUSTAL (Higgins and Sharp, 1988, genes 73, 237–244). The * mark identical amino acids.

FIG. 16: A. Amino acid sequence CpcrP (SEQ ID NO: 17) in the one-letter code deriving from the DNA partial sequence of the DNA fragment Cpcr. B. Comparison of the amino acid sequence CpcrP (SEQ ID NO: 17) with the oat sequence HaSGTP (SEQ ID NO: 18). The comparison was performed with the help of the program CLUSTAL (Higgins and Sharp, 1988, genes 73, 237–244). The * mark identical amino acids.

FIG. 17: DNA sequence of the nucleic acid fragment AtSGT (SEQ ID NO: 19) which was isolated from a cDNA expression bank of oat seedlings (example 9). It has a length of 2353 base pairs (bp) and contains an open reading structure starting at position 1 to 2023. Start- and stop codon are at positions 113–115 respectively 2023–2025.

FIG. 18: Amino acid sequence AtSGTP (SEQ ID NO: 21) in the one-letter code deriving from the DNA sequence of the nucleic acid fragment AtSGT.

FIG. 19: Comparison of the amino acid sequences HaSGTP (SEQ ID NO: 7) and AtSGTP (SEQ ID NO: 21). The comparison was performed with the help of the program CLUSTAL (Higgins and Sharp, 1988, genes 73, 237–244). The * mark identical amino acids.

Figure 20:
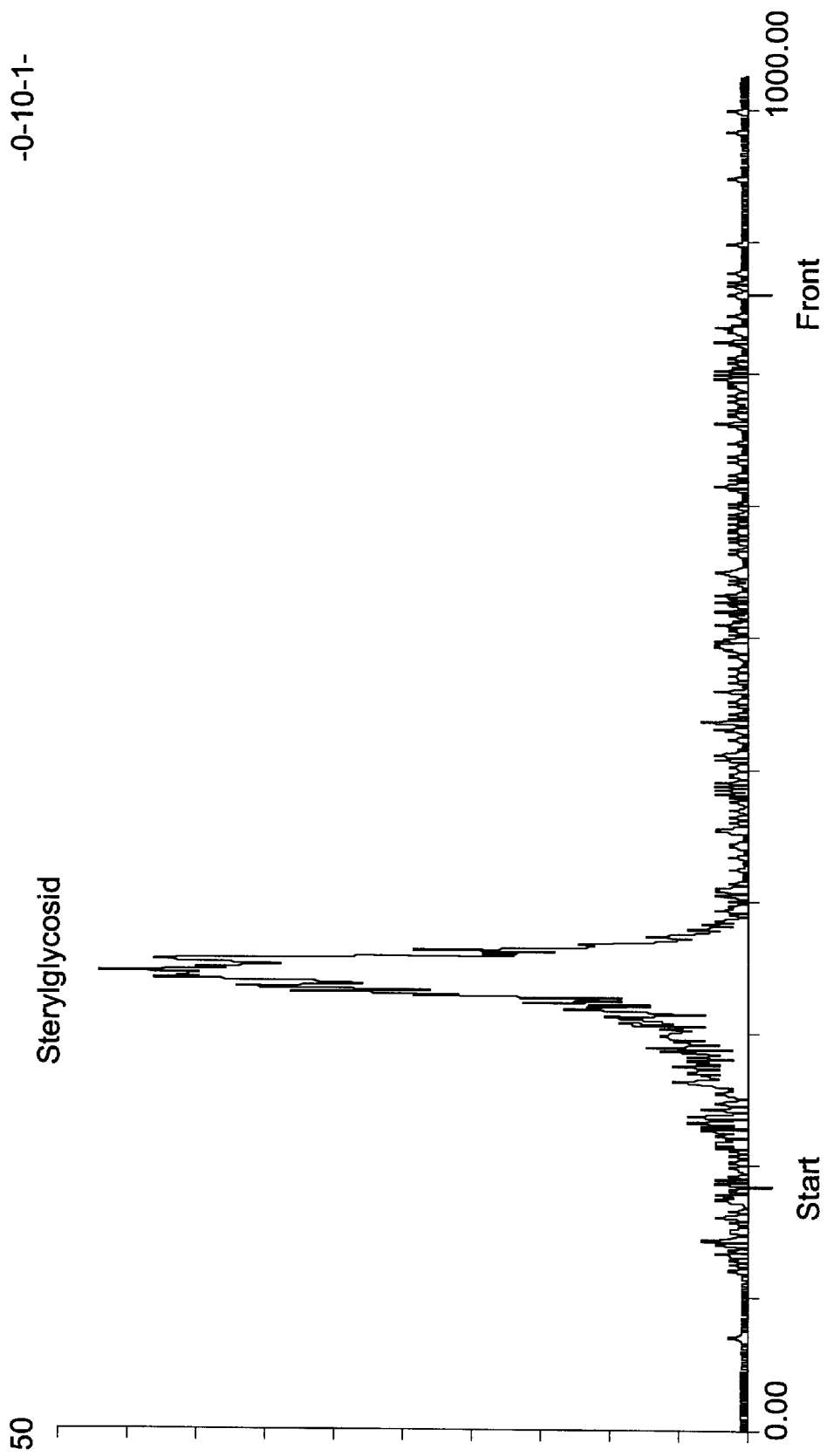

FIG. 20: Thin layer chromatographic analysis of radioactive products of in vitro enzyme assays which were performed with cell free homogenates of *e. coli* cells transformed with the plasmid pBS-AtSGT (see example 10). The organic phases were transferred to silica gel 60 plates (Merck, Darmstadt), which were developed with the solvent chloroform:methanol 85:15. The Rf-values of the radioactive, lipophile reaction product were determined with a Berthold-TLC analyser and were compared with authentic standards, which were detected with α-naphtol sulfuric acid. Only one product was to be found which could be identified as sterylglucoside.

FIG. 21: Partial amino acid sequence of the sequence HaSGTP (SEQ ID NO: 22) in the one-letter code.

FIG. 22: Partial amino acid sequence of the sequence AtSGTP (SEQ ID NO: 23) in the one-letter code.

FIG. 23: Partial amino acid sequence of the sequence in the one-letter code deriving from the *s. cerevisiae* gene L9470.23 (SEQ ID NO: 24).

The invention is explained by the following examples:
1. Purification of the UDP Glucose: Sterol Glycosyl Transferase, Antiserum, N-terminal Sequencing The purification of the enzyme, the production of the antiserum against the protein and the Western-blot analysis were performed according to the well-known methods Warnecke, D. C. and Heinz, E. (1994) Plant Physiol. 105: 1067–1073. Afterwards an analysis of partial sequences of the amino acid sequence of the protein was performed. The protein, which was purified to the point of homogeneity was subjected to a SDS-PAGE and electrophoretically transferred onto a poly vinylidene fluoride membrane (Immobilon P, Millipore, Eschborn). The protein was colored with coomassie brilliant blue R 250 (Biorad, Munich) and the ribbons corresponding to a molecular mass of 56 kD were cut out of the membrane. Directly afterwards, the protein was sequenced according to N-terminal or proteolytically cut to keep internal fragments. The protein was digested with typsine according to Bauw, G; van den Bulcke, M.; van Damme, J.; Puype, M.; van Montagu, M. and Vandekerckhove, J. (1988) J. Prot. Chem. 7: 194–196 and the proteolytical fragments were separated with a high-performance-liquid chromatography system (130A, Applied Biosystems, Weiterstadt) on a reverse phase column (Vydac C4, 300 Angstrom pore diameter, 5 $\mu$m particle size). The peptides were eluted with a linear gradient (0–80%B, solution A:water with 0.1% trifluoro acetic acid, solution B: 70 acetonitril with 0.09% trifluoro acetic acid) with a flux rate of 0.2 ml/min. The elution pattern of the peptides corresponded to a pattern which usually corresponds to a trypsine self-digestive. Even after several repetitions of the experiment no protein could be allocated to the purified protein based on the retention time. Thereafter most of the peptides were sequenced. The sequences, however, all corresponded to the amino acid sequence of the trypsine. These experiments showed that the purified very hydrophobe membrane protein is well resistant to the trypsine digestion and that the hydrophobe peptide fragments can hardly be disconnected from the membrane. The experiments continued however with an alternative strategy. After newly digestion experiments the eluted peptides were subjected to a rechromatography (with a nucleosile C8-column 120×1.6 mm gradient as above). This resulted in the surprising fact that a suspected homogenic peptide of the tryosine self-digestive contained a secondary component whose amino acid sequence did not correspond to the one of the trypsine. This sequence was in the one-letter code: MTETTIIQALEMTGQ (SEQ ID NO: 25). The protein sequencing were performed on an automatic sequencing apparatus according to the Standard-Edman degradation (473A, Applied Biosystems, Weiterstadt). 15 amino acid sequences were determined to a length of the N-terminal amino acid sequence. In the one letter code this came to: DVGGEDGYGDVTVEE (SEQ ID NO: 8). —Additionally the sequence of a peptide fragment was determined to a length of 14 amino acids. This came to the following in the one letter code: MTETIIQALEMTGQ (SEQ ID NO: 26).

2. Setting Up an Oat cDNA Bank

A cDNA expression bank was planned from oat to isolate complete clones of the sterol glycosyl transferase. First of all RNA was isolated from 4 day old oat seedlings (Avena sativa, type Alfred), which were cultivated in the dark. For this, the seedlings were pulverized in liquid nitrogen. The pulver was absorbed into a buffer with guanidine isothiocyanate and filtered. The RNA was sedimented in the ultracentrifuge by a cesium chloride solution. The sediment was absorbed in aqua dest. and the RNA precipitated and sedimented with 2 parts ethanol and 0.05 parts acetic acid. the sediment was absorbed in aqua dest. mRNA was isolated from the oat RNA. This was performed with dynabeads oligo (dT) of the company Dynal Ltd. (Hamburg) according to the instruction. With the help of the ZAP-cDNA synthesis kit (Company Stratagene, Heidelberg) cDNA was isolated from the isolated mRNA according to the manufacture's instruction and a cDNA bank was planned.

3. Isolation of Partial DNA Sequences of the Sterol Glycosyel Transferase from Oat with the PCR Method From the sequences of the N-terminal amino acid sequencing (see 1.) oligonucleotide primers were derived:
DW1=5'-GGITAYGGIGAYGTNACIGTIGARGA-3' (forward primer) (SEQ ID NO: 27)
DW2=5'-GAYGTIGGIGGIGARGAYGGNTA-3' (forward primer) (SEQ ID NO: 28)
as a reverse primer served the following:
XXS4T=5'-GATCTAGACTCGAGGTCGACTTTTTTTTTTTTT-3' (SEQ ID NO: 29)

Abbreviations: Y=C and T–D=G and A and T–I=inosine–N=A and G and C and T–R=G and A–K=G and T–S=G and C–H=A and T and C–B=G and T and C–V=G and A and C–X=C and I–W=A and T–M=A and C The polymers chain reaction—PCR method was performed as follows: reaction mix: 46 $\mu$l aqua dest.; 5 $\mu$l Boehringer (Mannheim) 10×PCR buffer; 1 $\mu$l each 10 mM dATP, dGTP, dCTP, dTDP; 1 $\mu$l each 100 $\mu$M DW1 (DW2 respectively), XXS4T; 0.25 $\mu$l Boehringer taq-polymerase; 0.5 $\mu$l cDNA from oat seedlings (see 2., concentration not defined.)

Conditions of reaction: 94° C., min; 30×(94° C., 40 s; 53° C., 1 min 72° C., 3 min); 72° C., 10 min.

This PCR reaction with a specific primer (DW1 respectively DW2) and an non-specific primer (XXS4T), which connects to all clones of the cDNA bank, which contain a so-called polyA end remained unsuccessful. In other words no DNA fragment could be amplified, cloned and sequenced, which contained sequence parts which corresponded to the primers used.

The PCR reaction was performed in various modifications (different temperature program, so-called nested PCR with the primers DW1 and DW2), but remained unsuccessful nevertheless. In addition experiments for the sequencing of peptide fragments of the purified protein were performed (see 1) to be able to perform PCR reactions with two specific primers.

The following oligonucleotide primer was derived from the sequences of the peptide amino acid sequencing (see 1.):
Wa1=5'-GCYTGDATDATIGTYTCIGTC-3' (reverse primer) (SEQ ID NO: 30)

The polymers chain reaction—PCR method was performed as follows: reaction mix: 46 $\mu$l aqua dest.; 5 $\mu$l Boehringer (Mannheim) 10×PCR buffer; 1 $\mu$l each 10 mM dATP, dGTP, dCTP, dTDP; 1 $\mu$l each 100 $\mu$M DW1 Wa1; 0.25 pl Boehringer taq-polymerase; 0.5 $\mu$l cDNA from oat seedlings (see 2., concentration not defined.) Conditions of reaction: 94° C., 3 min; 30×(94° C., 40 s; 53° C., 1 min; 72° C., 3 min); 72° C., 10 min.

Only by using the specific reverse primer Wa1 a successful PCR reaction could be performed: An agarose gel electrophoresis with 15 $\mu$l of the reaction resulted in a DNA ribbon of about 800 BP length.

This piece of DNA was cloned with the Sure Clone Ligation kit (Pharmacia, Freiburg) in a plasmid vector and partly sequenced from 5'- and 3' end. These sequences (wa18e and wa19er) are illustrated in FIG. 1.

4. Isolation of Complete Clones

The cloned piece of DNA (see 3) was marked and used for screening a cDNA bank (see 2) to isolate complete clones of the sterol glycosyel transferase.

The piece of DNA was marked in a non-radio active manner with the PCR DIG Probe Synthesis Kit (Boehringer, Mannheim) according to the manufacturer's instructions, DIG=a system containing digitoxigenin for marking nucleic acids from Boehringer (Mannheim). After that the marked sample was used for screening the oat cDNA bank. The method is described in the Boehringer DIG System User4s Guide for Filter Hybridization (Plaque Hybridization, Colorimetric Detection with NBT and BCIP). 250, sterol glycosyel transferase phage particles which are capable of infections were screened (hybridization temperature 69° C.). 50 positive clones were detected, of which 13 were subjected to a second and third screening. These 13 positive clones were transferred from the phage form into the plasmid form (in vivo excision according to Strategene Protocol ZAP-cDNA-Synthesis Kit, Heidelberg).

A clone of a length of about 2300 bp (named HaSGT in the following) was sequenced completely and in a twin threaded manner. This sequence in illustrated in FIG. 2: The partial sequences (wa18th and wa 19th) of the cloned PCR fragment are identical of more than 95% with the clone HaSGT (FIG. 3). This clone has a length of 2317 bp and has an open reading structure of bp 1 to bp 1971. A starting codon (ATG) for the translation begins at bp 148. If the open reading structure is translated into an amino acid sequence (HaSGTP, FIG. 4), then the amino acid sequence has a complete identity with the amino acid sequence of the peptide fragment of the purified protein and nearly complete identities with the N-terminal amino acid sequence of the purified protein (14 of 15 amino acids are identical, FIG. 15) This correspondence clearly demonstrates that the cloned cDNA corresponds to the purified protein. The difference with an amino acid lies in the fact that there are allomorphic differences. As the first amino acid of the N-terminal amino acid sequence of the purified protein (D) corresponds to the amino acid 133 of the open reading structure of the clone HaSGT, it is to be expected that the clone codes for a preprotein which in vivo can be cut to a mature protein (putative mature protein). The plasmid containing the 2317 bp long oat clone in the vector pBluescript I SK (inserted between the EcoRi- and the XhoI-cutting point ) is called pBS-HaSGT in the following.

5. Functional Expression of Parts of the Clone HaSGT in E.coli

To prove the fact that the cloed DNA sequence (see 4) codes for sterol glycosyel transferase, parts of the clone HaSGT were expressed in a functional manner in e. coli.

Two acts of cloning were performed in the vectors suitable for expression:
  a) This act of cloning produces a plasmid (pBS-HATG), which codes for a fusion protein whose first amino acid originates from the Bluescript lacZ-operon and the polylinker (in normal print, see below) and whose following amino acids correspond to those according to the starting methionine of the nucleotide sequence of the HaSGT which is translated into an amino acid sequence(underlined, see below).
  The plasmid pBS-HaSGT was cut with the restriction enzyme EaeI and EagI and the linealized part containing the vector sequences, is mixed with itself. The creating plasmid codes for a fusion protein whose beginning looks as follow:
  M T M I T P S S E L T L T K G N K-SWSSTAVAADADEPTGG . . . (SEQ ID NO: 31)
  b) This cloning produces a plasmid (pBS-HRP) which codes for a fusion protein whose first amino acids originate from the Bluescript lacT operon and the polylinker (in normal print, see below) and whose second part corresponds to the putative mature protein of oat (underlined, see below).

For this cloning a PCR test is performed, with which the DNA of the plasmid pBS-HaSGT is used as a matrix DNA. The following primers were used:
DW 15=GATGAGGAAATTCACTAGTTG (SEQ ID NO: 32)
DW 20=GATGGATCCACTTGATGTTGGAGG (SEQ ID NO: 33)

A PCR fragment of about 500 bp length was purified over an agarose gel, was cut with the restriction enzyme BamHI and NdeI and again purified over a gel from which a fragment of about a length of 450 bp was isolated.

The plasmid pBS-HaSGT was cut with the restriction enzyme BamHI and NdeI and a fragment of about a length of 4300 bp was eluted. This fragment was mixed with the cut PCR fragment and used for transformation of e. coli. Plsmid DNA was isolated and partly sequenced from the transformed cells. The plasmid DNA codes for the following fusion protein:
M T M I T P S S E L T L T K G N K-SWSSTAVAALELVDLDVGGEDGY . . . (SEQ ID NO: 34)

It was checked with the plasmids pBS-HATG and the pBS-HRP transformed e. coli cells whether the respective fusion protein was expressed by performing an in vitro enzyme assay for proving the existence of sterol glycosyel transferase activity with cell homogenates.

The cells of 2 ml overnight culture (2 ml LB-Ampicillin, 37° C., 14 h) were sedimented and absorbed in 1 ml lysis buffer (50 mM Tris/HCl pH 8.0; 15% glycerole; 5 mM DTT; 1 mg/ml lysozyme (from egg, Boehringer, Mannheim); 200 $\mu$M pefabloc, (Merck, Darmstadt); 0.1% tritone X100. After a 5 minute period of incubation at 20° C. the suspensions were put on ice and the cells were broken up by 3×3 seconds treatment with the super sonic wand. The reaction solution of the in vitro enzyme assay had a volume of 60 $\mu$l and was composed of the following (17.1.1996):

100 mM Tris/HCl pH 8.0 (at 30° C.); 1 mM DTT; 0.2% tritone X100; 1 mM cholesterol, 5 $\mu$l e. coli-homogenate (1–2 mg protein/ml), 100.000 dpm UDP-[U-$^{14}$C]-glucose (144 $\mu$M). The reaction was stopped after 20 minutes (at 30° C.) by mixing with 0.5 ml water and 1.6 ml ethyl acetate. After the phase separation by short centrifugation the top organic phase was taken and the radio activity contained therein was determined with a scintillation counter:

E. coli homogenate with pBS-HaATG: 620 desintegrations per minute (radioactive desintegrations per minute )(dpm)

E. coli homogenate with pBS-HRP: 3100 dpm

E. coli homogenate, not transformed: 0 dpm

Of parallel samples, which were incubated for a longer period of time, the radio activity existing in the organic phase was exposed to a thin layer chromatographic analysis: The organic phases were transferred to silica gel 60 plates (Merck, Darmstadt), which were developed with the solvent chloroform:methanol 85:15. The Rf-values of the radioactive, lipophile reaction product were determined with a Berthold-TLC analyzer and were compared with authentic standards, which were detected with α-naphtol sulfuric acid. Only one product was to be found which could be identified as sterylglucoside (see FIG. 6). Thereby it could be proven that the transformed e. coli cells expressed a protein, which shows sterol glycosyel transferase activity. Non-transformed control cells showed no sterol glycosyel transferase activity.

The expression of the plant peptide sequences were also proven by Western-blot-analysis: 40 $\mu$g each of protein of the e. coli homogenate were precipitated with 8% trifluoro acetic acid and thereafter were subjected to a SDS-polyacrylamide gel ectrophoresis (10%) (with Biorad Mini Protean II Apparatus, München). The proteins were transferred to a nitro cellulose membrane by electroblotting and an immuno tint was performed (anti-sterol-glucosyl transferase antiserum 1:1000 sterol glycosyl transferase, colored with hydrogen dioxide and 4-chloro-naphtol). The westernblot membrane is illustrated in FIG. 7. With e. coli with pBS-HRP a ribbon of about 59 kD is markedly colored. With e. coli with pBS-HaATG a 74 kD ribbon is colored the most intensively. These proteins are the proteins coding on the plasmids.

6. Functional Expression of a Part of the Clone HaSGT in S. cerevisiae

For this, a vector was produced, which is suitable for the expression of the herbal cDNA in saccaromyces cerevisiae.

amplification of the CYC1 terminator Zaret, J. K. and Sherman, F. (1982) cell 28: 563–573 with the PCR methode by using the primer
5'-GATATCTAGAGGCCGCAAATTAAAGCCTTC-3' (SEQ ID NO: 35)
and
5'-CCCGGGATCCGAGGGCCGCATCATGTAATT-3' (SEQ ID NO: 36)
and cloning into the vector pRS316 Sikorski, R. S. and Hieter, P (1989) Genetics 122: 19–27. the resulting plasmid was called pRS316t.

cloning of the GAL1 promoter (0.5 kb SpeI/XbaI fragment) from the pYES vector (invitrogenic) into the vector bluescript KS (Stratagen, Heidelberg).

The cloning resulted in pGAL1.

cloning of the GAL1 promoter (0.5 kb XbaI/PvuII fragment) from the pGAL1 into the vector bluescript KS (HincII/XbaI). The resulting plasmid was called pGAL2.

cloning of the fragment via XhoI/SacI into the pYES2.0 vector (Invitrogen, Leek, Holland)

The cloning resulted in pGAL3.

cloning of the fragment from the pGAL3 via KpnI/XhoI into the pRS316t.

This resulted in the single copy yeast expression vector pGAL4 with the following characteristics:

single copy plasmid, URA-marker, GAL1 promoter, CYC1 terminator, MCS.

Part of the oat clone HaSGT as cut with SalI/KpnI from the plasmid pBS-HaSGT and cloned into the pSP72 vector (Promega, Heidelberg, SalI/KpnI). The SalI/KpnI fragment of the resulting plasmid pSPHAM1 entails the respective percentage of the HaSGT and was cloned into the vector pGAL4 (XhoI/BamHI). The resulting plasmid became pGALHAM1 and was used for the transformation of the saccaromyces cerevisiae root UTL-7A (MATa, ura3–52, trp1, leu2–3/112).

To be able to prove the sterol glycosyl transferase activity of the expressed plant sequence, an in vitro enzyme assay with cell-free homogenates of the yeast cells was performed. The yeast cells were cultivated on the following medium (72 h at 29° C. aerob shaken):

6.7 g/l difco yeast nitrogen base without amino acids; 10 mg/l;

60 mg/l leucin: 1% galactose.

The cells of a 30 ml culture were sedimented and absorbed in 1 ml lysis buffer:

50 mM Tris/HCl pH 7.5; 15% glycerol; 0.1% triton X100; 200 μM pefabloc (Merck, Darmstadt; 1 mM DTT; 0.5 mg/ml lyticase (Sigma, Deisenhofen). After an incubation of 25 min at 20° C. the cells were broken up by ultra sonic wand treatment (3×10 s). The reaction solution of the in vitro enzyme assay had a volume of 150 μl and was composed of the following (10.3.1996):

100 mM Tris/HCl pH 8.0 (at 30° C.); 1 mM DTT; 0.2% triton X100; 1 mM cholesterol, 20 μl yeast homogenate, 350.000 dpm UDP-[U-$^{14}$C]-glucose (4.2 μM).

The reaction was stopped after 45 minutes (at 30° C.) by mixing with 0.5 ml water and 1.6 ml ethyl acetate. After the phase separation by short centrifugation the top organic phase was taken and the radio activity contained therein was determined with a scintillation counter:

Yeast homogenate with pGAL4: 0 dpm

Yeast homogenate, with pGALHAM1: 13.000 dpm

Of parallel samples, which were incubated for a longer period of time, the radio activity existing in the organic phase was exposed to a thin layer chromatographic analysis: The organic phases were transferred to silica gel 60 plates (Merck, Darmstadt), which were developed with the solvent chloroform:methanol 85:15. The Rf-values of the radioactive, lipophile reaction product were determined with a Berthold-TLC analyzer and were compared with authentic standards, which were detected with α-naphtol sulfuric acid. Only one product was to be found which could be identified as sterylglucoside (see FIG. 8). Thereby it could be proven that the transformed e. coli cells expressed a protein, which shows sterol glycosyel transferase activity. Non-transformed control cells showed no sterol glycosyl transferase activity.

7. Functional Expression of Genomic DNA Sequences of Saccharomyces cerevesiae in E.coli The amino acid sequence deriving from the oat sequence, which was cloned by us, has obvious similarities with the derived amino acid sequence of a piece of genomic DNA of S. cerevisiae (see FIG. 9). This deals with the chromosome XII Cosmid 9470 (gene bank No. gb U17246). The similarity refers to the 34-range of the open reading structure in reverse direction of bp 32961–36557 (gene L9470.23). For this putative gene no function has been known so far. Parts of the open reading structure were expressed by us in e.coli in a functional manner: A fragment of a size of 6359 bp was isolated from a cosmid 9470-DNA preparation by cutting with the enzyme NdeI and SpeI (Cosmid bp 31384–37744). This sequence contained the desired reading structure and could be used for further subcloning by cloning into the vector pbluescript II KS (cut with EcoRV). This plasmid was called pBS-HSC. Four subclonings were performed, which were supposed to lead to the expression of parts of various length of the open reading structure. These clonings are listed below in a column:

| Cloning | 1 | 2 | 3 | 4 |
|---|---|---|---|---|
| Cutting of pBS-HSC with | Eco47III SmaI | PstI | EcoRI BamHI | SspI |
| Possible length of the isolated fragment in bp | 3900 | 5000 | 3800 | 2500 |
| expression vector | pUC19 | pUC8 | pBSIIKS | pUC19 |
| Cutting of the expression vector with | SmaI | PstI | EcoRI BamHI | SmaI |

All these acts of cloning lead to plasmids, which code for fusion proteins, which derive in the first part from the lacZ operon and parts of the polylinker of the vectors and in the second part consist of polypeptides, which correspond to parts of the gene L9470.23. Illustration 9 illustrates the derived protein sequence of the open reading structure (Gene L9470.23). In this illustration the amino acids are marked, with which the second paragraph of the fusion proteins of the various clones starts.

The plasmids of the clonings 1–4 were used for the transformation of e. coli. To our surprise we were able to prove cell-free homogenates of these cells with an in vitro enzyme assay sterol glycosyl transferase activity. For this the cells of 15 ml overnight culture (15 ml LB-ampicillin, 37° C., 14 h) were sedimented and absorbed in 1.5 ml lysis buffer (50 mM Tris/HCl pH 8.0; 15% glycerol; 5 mM DTT; 1 mg/ml lysozyme (from egg, Boehringer, Mannheim); 200 µM pefabloc (Merck, Darmstadt). After a period of 5 minutes incubation at 20° C. the suspension was put on ice and the cells were broken up by a 3×3 second treatment with the super sonic wand.

The reaction solution of the in vitro enzyme assay had a volume of 100 µl and was composed of the following (22.5.1996):

50 mM Tris/HCl pH 8.0 (at 30° C.); 1 mM DTT; 1 mM $MgCl_2$; 10 µl 2 mM ergosterol ethanol; 45 µl e.coli homogenate, 150.000 dpm UDP-[U-$^{14}$C]-glucose (2.2 µM). The reaction was stopped after 45 minutes (at 30° C.) by mixing with 0.5 ml water and 1.6 ml ethyl acetate. After the phase separation by short centrifugation the top organic phase was taken and the radio activity contained therein was determined with a scintillation counter:

| | |
|---|---|
| E. coli homogenate with clone 1: | 7500 dpm |
| E. coli homogenate with clone 2: | 10700 dpm |
| E. coli homogenate with clone 3: | 35000 dpm |
| E. coli homogenate with clone 4: | 32700 dpm |
| E. coli homogenate, not transformed: | 2000 dpm |

Of parallel samples of clone 2 and 4 the radio activity existing in the organic phase was exposed to a thin layer chromatographic analysis: The organic phases were transferred to silica gel 60 plates (Merck, Darmstadt), which were developed with the solvent chloroform:methanol 85:15. The Rf-values of the radioactive, lipophile reaction product were determined with a Berthold-TLC analyzer and were compared with authentic standards, which were detected with α-naphtol sulfuric acid. Only one product was to be found which could be identified as sterylglucoside (see FIG. 10). Thereby it could be proven to our surprise that the transformed e. coli cells expressed a protein, which shows sterol glycosyl transferase activity. The organic phases of assay with not transformed control cells also contained a bit of radioactivity; this however is not a marked sterylglucoside. The amino acid sequence deriving from the gene 9470.23 is called ScSGTP in the following (see FIG. 9).

8. PCR-tests with Arabidopsis, Candida and Potato

From similar ranges of amino acid sequences between HaSGTP (see 4) and ScSGTP (see 7) oligonucleotide primers could be derived, which could be used for PCR test:
DW3=GSIWCIVSIGGIGAYGTHYWICC (SEQ ID NO:37)
WA3=GTIGTICCISHICCISCRTGRTG (SEQ ID NO:38)
WA6=GTISKIGTCCAIGGCATIGTRAA Abbreviations see 4:
The polymerase chain reaction method was performed as follows:
reaction mix: 40 µl aqua dest.; 5 µl Boehringer (Mannheim) 10×PCR buffer; 1 µl each 10 mM dATP, dGTP, dCTP, dTDP; 1 µl each 100 µm oligonucleotide primer, 0.25 µl Boehringer taq-polymerase; 0.5 µl matrix DNA.

Conditions of reaction: 94° C., 3 min; 30×(94° C., 45 s; 53° C., 1 min; 72° C., 2 min); 72°, 10 min.
a.) primer DW3 and Wa6, as matrix DNA cDNA was used which was synthesized from aerabidopsis mRNA.
b.) Primer DW3 and Wa6, as matrix DNA a phage mix was used of a lamda-ZAP-cDNA bank (Stratagene, Heidelberg) of potato with about $10^{10}$ plaque forming units per ml.
c.) Primer DW3 and Wa3, as matrix DNA genomic DNA from candida albanis (about 50 ng/µl) was used.

Result: An agarose gel electrophoresis with 15 µl of the reaction solutions resulted in DNA ribbons of about a length of 340 bp (arabidopsis, potato) and a length of about 940 pb (candida albicans).

These pieces of DNA were cloned with the pGEM-T vector system (promega, Heidelberg) in a plasmid vector and partially or completely sequenced. These sequences are illustrated in FIGS. 11–13 (arabidopsis=Apcr; potato=Kpcr; candida=Cpcr). The amino acid sequences deriving from these sequences (AperP, KpcrP, CpcrP) were compared to the amino acid sequences of the oat clone -AGTP respectively the yeast gene L947 (Sc-SGTP) (see FIGS. 14–16):

To our surprise is
the potato sequence KpcrP identical to 86% with the respective part of the oat sequence HaSGTP,
the arabidopsis sequence ApcrP identical to 90% with the respective part of the oat sequence HaSGTP and
the candida sequence CpcrP identical to 64% with the respective part of the s. cerevisiae sequence ScSGTP.

9. Isolation of Complete Clones from Arabidopsis

The arabidopsis PCR clone was used with a method as described in 4. for the isolation of complete clones from a arabidospsis-lamda-Zap-cDNA bank (received from the Stock Center of the MPI for cultivation science, Cologne). A clone of about 2300 bp length (named AtSGT in the following) was sequenced completely and twin threaded (FIG. 17). This clone has a length of 2353 and has an open reading structure of 1 bp to 2023 bp. A starting codon (ATG) for the translation begins at bp 113. If the open reading structure is translated into an amino acid sequence (AtSGTP, FIG. 18) that the amino acid sequence has large similarities with the oat sequence HaSGTP (see FIG. 19).

10. Functional Expression of Parts of the Clone AtSGT in E. coli

To prove the fact that clone AtSGT codes for sterol glycosyl transferase it was expressed in e. coli.

This act of cloning produces a plasmid (pBS-AtSGT), which codes for a fusion protein whose first amino acid originates from the pBluescript lacZ-operon and the polylinker (in normal print, see below) and whose following amino acids correspond to those according to the open reading structure of the clone AtSGT(underlined, see below).

The beginning of the fusion protein looks as follow:
MTMITPSSELTLTKGNKSWSSTAVAAA LELVDP-PGCRNSEFGTPLILSFTFWD . . . (SEQ ID NO: 40)

With regard to the e. coli cells transformed with the plasmid pBS-AtSGT it was checked whether the respective fusion protein was expressed by performing an in vitro enzyme assay for proving sterol glycosyl transferase activities with cell homogenates.

The cells of 1.5 ml overnight culture (1.5 ml LB-Ampicillin, 37° C., 14 h) were sedimented and absorbed in 1 ml lysis buffer (50 mM Tris/HCl pH 8.0; 15% glycerole; 5 mM DTT; 1 mg/ml lysozyme (from egg, Boehringer, Mannheim); 200 µM pefabloc (Merck, Darmstadt); 0.1% tritone X100. After a 5 minute period of incubation at 20° C. the suspensions were put on ice and the cells were broken up by 3×3 seconds treatment with the super sonic wand. The reaction solution of the in vitro enzyme assay had a volume of 50 µl and was composed of the following (11.3.1996):

100 mM Tris/HCl pH 8.0 (at 30° C.); 1 mM DTT; 0.2% tritone X100; 1 mM cholesterol, 7.5 µl e. coli-homogenate, 100.000 dpm UDP-[U-$^{14}$C]-glucose (2.8 µM).

The reaction was stopped after 20 minutes (at 30° C.) by mixing with 0.5 ml water and 1.6 ml ethyl acetate. After the phase separation by short centrifugation the top organic phase was taken and the radio activity contained therein was determined with a scintillation counter:

| | |
|---|---|
| E. coli homogenate with pBS-AtSGT: | 1300 dpm |
| E. coli homogenate, not transformed: | 100 dpm (blank reading) |

Of parallel samples, which were incubated for a longer period of time, the radio activity existing in the organic phase was exposed to a thin layer chromatographic analysis: The organic phases were transferred to silica gel 60 plates (Merck, Darmstadt), which were developed with the solvent chloroform:methanol 85:15. The Rf-values of the radioactive, lipophile reaction product were determined with a Berthold-TLC analyzer and were compared with authentic standards, which were detected with α-naphtol sulfuric acid. Only one product was to be found which could be identified as sterylglucoside (see FIG. 20). Thereby it could be proven that the transformed e. coli cells expressed a protein, which shows sterol glycosyl transferase activity. Non-transformed control cells showed no sterol glycosyl transferase activity.

All molecular biological working steps, which are not described in the examples in detail, were performed according to the working instructions from Sambrook, J.; Fritsch, E. F. and Maniatis, T. (1989): Molecular cloning. A Laboratory Manual. Second edition. Cold Spring Harbor Laboratory Press. Cold Spring Harbor, if not mentioned otherwise.

Definitions

STEROLES are called the following substances, which have the following structural characteristics: they consist of a 5α-cholestan-3-β-ol or 5α-cholestan-3-α-ol skeletal structure. This skeletal structure can be modified by side chains or double bonds in the ring system.

STEROLE IN THE STRICTEST SENSE are cholesterol, ergosterol, β-sistosterol, stigmasterol.

STERYGLYCOSIDES are sterols or sterols in the strictest sense, which are at the C3-atom via the oxygen atom with a sugar molecule or connected to it. These sugars may be for example glucose, galactose, mannose, xylose, arabinose or other sugars or sugar derivations in a furanosidic or pyranosidic form and in α- or β-connection. Connections containing glucuron acid are excluded from this definition.

SECONDARY PRODUCTS OF STERYGLYCOSIDES are secondary products on one hand, which can be synthesized in organisms or in in vitro systems in an enzymatic manner from sterylclycosides (as for example sterylglycosides, -tryglycosides, -oligoglycosides or acyletic sterylglycosides). On the other hand these are substances, which can be presented with methods of the organic chemistry from sterylglycosides.

STEROL GLYCOSYL TRANSFERASES are enzymes, which transfer a sugar molecule, especially from activated sugars or activated sugar derivations, especially from sugar nucleotides or sugar derivation nucleotides onto the OH-group at the C3-atom of sterols or sterols in the strictest sense. The transfer of glucuron acid is excluded from this method.

STEROL GLYCOSYL TRANSFERASES are enzymes, which transfer a glucose molecule, especially from activated glucose, especially from uridin diphospate onto the OH-group at the C3-atom of sterols or sterols in the strictest sense.

STEROL GLYCOSYL TRANSFERASE IN THE STRICTEST SENSE are enzymes, which transfer a sugar molecule, especially from activated sugars or activated sugar derivations, especially from sugar nucleotides or sugar derivation nucleotides onto the OH-group at the C3-atom of sterols or sterols in the strictest sense. The transfer of glucuron acid is excluded from this method.

STEROL GLYCOSYL TRANSFERASE IN THE STRICTEST SENSE are enzymes, which transfer a glucose molecule, especially from activated glucose, especially from uridin diphospate onto the OH-group at the C3-atom of sterols or sterols in the strictest sense.

SUGAR in this sense are hexoses or pentoses in furanosidic or pyranosidic form.

SUGAR DERIVATIONS are sugar, which by oxidation or reduction or addition or removal of functional groups are modified in their structure. N-acetyl glucosamine and desoxyribose can be quoted as an example, here.

SUGAR NUCLEOTIDES in the sense used here are substances with which one of the organic bases thymine, adenine, guanine, uracile or cytosine is connected to a ribose respectively a desoxyribose with a further sugar molecule.

PARTS OF PLANTS are parts of a plant as for example leaves, roots, seeds or fruit.

VECTORS are nucleic acid fragments, which under certain conditions are capable of multiplication and are used for the insertion of extraneous nucleic acid fragments for the purpose of multiplication of this fragment or the expression of this fragment (for example for the production of a protein). Typical examples are plasmids and phages.

CHIMERICAL GENE is a nucleic acid fragment, which is composed of various parts and does not occur in this form in a natural way. It entails a sequence coding for a polypeptide and suitable control sequences, which enable the expression. The coding sequence can exist with regard to control sequences in "sense- or "anti-sense" orientation.

ISOLATING is the process of obtaining certain things from a mixture of various things. These things may be substances (as for example protein, nucleic acid fragments mRNA, DNA, cDNA-clones, genes), parts of cells (as for example membranes), cells (as for example bacteria cells, plant cells, protoplasts), cell lines or organisms and their offsprings.

Literature List

1. Bauw, G.; van den Bulcke, M.; van Damme, J.; Puype, M.; van Monatgu, M. and Vanderkerckhove, J. (1988) J. Prot. Chem. 7: 194–196
2. King, M. L.; Ling, H. C., Wang, C. T. and Su, M. (1979) J. Nat. Prod. 701 ff.

3. Miles, D. H.; Stagg, D. D. and Parish, E. J. (1979 J. Nat. Prod. 42: 700 ff
4. Normnura, T.; Watanabe, M.; Inoue, K. and Ohata, K. (1978) Japan J. Pharmacol. 28, suppl.
5. Okuyama, E. and Yamazaki, M. (1983) Yakugaku Zasshi 103: 43 ff.
6. Seki, J.; Okita, A.; Watanabe, M.; Nakagawa, T.; Honda, K.; Tatewaki, N. and Sugiyama, M. (1985) J. Pharm. Sci. 74: 1259–1264
7. Sikorski, R. S. and Hieter, P. (1989) Genetics 122: 19–27
8. Warnecke, D. C. and Heinz, E. (1994) Plant Physiol. 105: 1067–1073
9. Zaret, J. K. and Sherman, F. (1982) Cell 28: 563–573
10. Sambroock, J.; Fritsch, E. F. and Maniatis, T. (1989): Molecular cloning. A Laboratory Manual. Second Edition. Cold Spring Harbor Laboratory Press, Cold Spring Harbor.

What is claimed is:

1. An isolated cDNA sequence that codes for a protein with enzymatic activity of sterol glucosyl transferase, wherein said sequence is derived from a plant.

2. The isolated cDNA sequence of claim 1, wherein said sequence is derived from an organism selected from the group consisting of *Avena sativa, Arabidopsis thalliana, Solanum tuberosum.*

3. The isolated cDNA sequence of claim 1, wherein the sterol is selected from the group consisting of cholesterol, algosterol, β-sitosterol and stigmasterol.

4. The isolated cDNA sequence of claim 1, wherein the encoded protein comprises at least fourteen successive amino acids which are identical with the sequences shown in SEQ ID NO:7 or SEQ ID NO:21 and comprising the amino acid sequence HHGG (SEQ ID NO:41).

5. The isolated cDNA sequence of claim 1, wherein the DNA encodes an amino acid sequence having at least 64% homology with a sequence selected from the group consisting of SEQ ID NO:15, SEQ ID NO:16, SEQ ID NO:17, SEQ ID NO:18, SEQ ID NO:22, and SEQ ID NO:23.

6. The isolated cDNA sequence of claim 1, wherein the encoded protein comprises the amino acid sequence HHG-GxxxxxxxxxxxxPxxxxxxxxxQ (SEQ ID NO:42), wherein x represents any amino acid.

7. The isolated cDNA sequence of claim 1, consisting of SEQ ID NO:3.

8. The isolated cDNA sequence of claim 1, consisting of SEQ ID NO:19.

9. A recombinant protein with enzymatic activity of sterol glucosyl transferase having an amino acid sequence deduced from a DNA sequence selected from the group consisting of SEQ ID NO:1, SEQ ID NO:2, SEQ ID NO:3, SEQ ID NO:5, SEQ ID NO:6, SEQ ID NO:11, SEQ ID NO:12, SEQ ID NO:13 and SEQ ID NO:19.

10. A transgenic organism comprising a cDNA sequence according to claim 1, wherein the organism is selected from a plant, a plant cell, a plant part, a yeast and a bacterium.

11. A transgenic organism comprising a chimeric gene construct comprising an isolated DNA sequence that codes for a protein with enzymatic activity of sterol glucosyl transferase, wherein the transgenic organism is a plant.

12. The transgenic organism of claim 10, having an altered sterol glycoside content or composition in comparison to wild-type plants, plant cells or plant parts.

13. The transgenic organism of claim 10, having enhanced resistance against drought, high salt concentration, cold, frost or fungal attack in comparison to wild-type plants, plant cells or plant parts.

14. The transgenic organism of claim 11, having an altered sterol glycoside content or composition in comparison to wild-type plants, plant cells or plant parts.

15. The transgenic organism of claim 11, having enhanced resistance against drought, high salt concentration, cold, frost or fungal attack in comparison to wild-type plants, plant cells or plant parts.

16. A transgenic cell comprising a cDNA sequence that codes for a protein with the enzymatic activity of sterol gulucosyl tranferase.

17. The transgenic cell of claim 16, having enhanced resistance against high salt concentration, ethanol concentration, cold, frost or high temperatures in comparison to wild-type cells.

18. An isolated nucleic acid comprising the sequence shown in SEQ ID NO:1.

19. An isolated nucleic acid comprising the sequence shown in SEQ ID NO:2.

20. An isolated nucleic acid comprising the sequence shown in SEQ ID NO:3.

21. An isolated nucleic acid comprising the sequence shown in SEQ ID NO:5.

22. An isolated nucleic acid comprising the sequence shown in SEQ ID NO:6.

23. An isolated nucleic acid comprising the sequence shown in SEQ ID NO:11.

24. An isolated nucleic acid comprising the sequence shown in SEQ ID NO:12.

25. An isolated nucleic acid comprising the sequence shown in SEQ ID NO:13.

26. An isolated nucleic acid comprising the sequence shown in SEQ ID NO:19.

* * * * *

SEQUENCE LISTING (1) GENERAL INFORMATION:

(iii) NUMBER OF SEQUENCES: 42

(2) INFORMATION FOR SEQ ID NO: 1:

(i) SEQUENCE CHARACTERISTICS:
      (A) LENGTH: 339 base pairs
      (B) TYPE: nucleic acid
      (C) STRANDEDNESS: unknown
      (D) TOPOLOGY: unknown (ii) MOLECULE TYPE: cDNA (xi) SEQUENCE DESCRIPTION: SEQ ID NO: 1:

```
GGGTATGGGG ACGTGACGGT TGAAGAATCA TTGGATGGAG CGGATATACC ATATAGACCT      60

CCTATGCAGA TTGTTATACT TATTGTGGGT ACAAGGGGAG ATGTTCAGCC ATTTGTTGCT     120

ATAGGAAAAC GCTTACAGGA TCATGGACAC CGTGTGAGAT TAGCCACTCA TGCCAACTTT     180

AAGGAGTTCG TACTGACAGC TGGGCTGGAG TTTTTTCCAC TTGGTGGAGA TCCAAAAATA     240

CTTGCTGAAT ACATGGTGAA GAATAAAGGG TTCCTGCCAT CAGGCCCATC AGAAATTCCT     300

ATTCAAAGAA AGCAGATGAG AGAAATTATA TTTTCCTTG                            339
```

(2) INFORMATION FOR SEQ ID NO: 2:

(i) SEQUENCE CHARACTERISTICS:
      (A) LENGTH: 221 base pairs
      (B) TYPE: nucleic acid
      (C) STRANDEDNESS: unknown
      (D) TOPOLOGY: unknown (ii) MOLECULE TYPE: cDNA (xi) SEQUENCE DESCRIPTION: SEQ ID NO: 2:

```
CCTCATGGAT ACATCTGGAG TCCTCATCTT GTTCCAAAAC CAAAAGACTG GGGCCCCAGG      60

ATTGATGTTG TTGGATTCTG CTTCCTCGAT CTTGCTTCTG ATTACGAACC ACCTGAAGAA     120

CTTGTGAAAT GGCTTGAAGC TGGTGACAAG CCCATTTATG TTGGTTTCGG TAGCCTTCCA     180

GTTCAGGATC AACAAAGAT GACCGAAACC ATCATCCAAG C                         221
```

(2) INFORMATION FOR SEQ ID NO: 3:

(i) SEQUENCE CHARACTERISTICS:
      (A) LENGTH: 2317 base pairs
      (B) TYPE: nucleic acid
      (C) STRANDEDNESS: unknown
      (D) TOPOLOGY: unknown (ii) MOLECULE TYPE: cDNA (ix) FEATURE:
      (A) NAME/KEY: CDS (B) LOCATION:148..1971

(xi) SEQUENCE DESCRIPTION: SEQ ID NO: 3:

| | |
|---|---:|
| CGAATCCTCC GGCTTCTCAT CCCGCATCTC GTCGGCCGCT CCTTTCCCCC TCCCCGCCGC | 60 |
| AACAGCAGGA GGTCCAGGCG GAGGAGTAAC CGCCGCGCCA AGTCTGGAAT CTCCGGGCCC | 120 |

| | | |
|---|---|---:|
| ACCGGGCCAG CAGCGGGGGC GGTACAA ATG GCC GAT GCC GAG CCG ACC GGC | | 171 |
| Met Ala Asp Ala Glu Pro Thr Gly | | |
| 1 5 | | |
| GGG GGA GGC AAG GGC GCG GAA GAT ATA GGA GGA GCG GCG GAG GCG CAC | | 219 |
| Gly Gly Gly Lys Gly Ala Glu Asp Ile Gly Gly Ala Ala Glu Ala His | | |
| 10 15 20 | | |
| AGT CGC GAC AGC CCT GCC TCG GCG GCA CTA CCC ACG GCG CCG TCG ACG | | 267 |
| Ser Arg Asp Ser Pro Ala Ser Ala Ala Leu Pro Thr Ala Pro Ser Thr | | |
| 25 30 35 40 | | |
| TCT TCC TCT TCC GCA GAC AAC GGG AAC CTC CAT AGA TCA AGC ACT ATG | | 315 |
| Ser Ser Ser Ser Ala Asp Asn Gly Asn Leu His Arg Ser Ser Thr Met | | |
| 45 50 55 | | |
| CCA GGA GTG ATC AAG GAT GCT GAA ATA ATT ACT GAA ACT ACA GGA CCG | | 363 |
| Pro Gly Val Ile Lys Asp Ala Glu Ile Ile Thr Glu Thr Thr Gly Pro | | |
| 60 65 70 | | |
| TCG AAT TTT GAA AGG TCG AAA ACC GAG AGA CGC CGG CAG AAT AAT GAT | | 411 |
| Ser Asn Phe Glu Arg Ser Lys Thr Glu Arg Arg Arg Gln Asn Asn Asp | | |
| 75 80 85 | | |
| CCT GCT AAA CAG TTA TTG GAT GAT AAG ATT TCC GTA AGG AAA AAG CTC | | 459 |
| Pro Ala Lys Gln Leu Leu Asp Asp Lys Ile Ser Val Arg Lys Lys Leu | | |
| 90 95 100 | | |
| AAA ATG CTA AAC CGC ATT GCT ACA GTG AGA GAT GAT GGA ACT GTG GTT | | 507 |
| Lys Met Leu Asn Arg Ile Ala Thr Val Arg Asp Asp Gly Thr Val Val | | |
| 105 110 115 120 | | |
| GTT GAT GTA CCA AGC TCT CTG GAT TTG GCT CCA CTT GAT GTT GGA GGA | | 555 |
| Val Asp Val Pro Ser Ser Leu Asp Leu Ala Pro Leu Asp Val Gly Gly | | |
| 125 130 135 | | |
| GAG GAT GGC TAT GGT GAT GTC ACT GTT GAA GAA TCA TTG GAT GGA GCA | | 603 |
| Glu Asp Gly Tyr Gly Asp Val Thr Val Glu Glu Ser Leu Asp Gly Ala | | |
| 140 145 150 | | |
| GAT ATA CCA TCC ATA CCT CCT ATG CAG ATT GTT ATA CTT ATT GTG GGT | | 651 |
| Asp Ile Pro Ser Ile Pro Pro Met Gln Ile Val Ile Leu Ile Val Gly | | |
| 155 160 165 | | |
| ACA AGG GGA GAT GTT CAG CCA TTT GTT GCT ATA GCA AAA CGC TTA CAG | | 699 |
| Thr Arg Gly Asp Val Gln Pro Phe Val Ala Ile Ala Lys Arg Leu Gln | | |
| 170 175 180 | | |
| GAT TAT GGA CAC CGT GTG AGA TTA GCC ACT CAT GCC AAC TAT AAG GAG | | 747 |
| Asp Tyr Gly His Arg Val Arg Leu Ala Thr His Ala Asn Tyr Lys Glu | | |
| 185 190 195 200 | | |
| TTC GTA CTG ACA GCT GGG CTG GAG TTT TTC CCA CTT GGT GGA GAT CCA | | 795 |
| Phe Val Leu Thr Ala Gly Leu Glu Phe Phe Pro Leu Gly Gly Asp Pro | | |
| 205 210 215 | | |
| AAA CTA CTT GCT GAA TAC ATG GTG AAG AAT AAA GGG TTC CTG CCT TCA | | 843 |
| Lys Leu Leu Ala Glu Tyr Met Val Lys Asn Lys Gly Phe Leu Pro Ser | | |
| 220 225 230 | | |
| GGC CCA TCA GAA ATT CCT ATT CAA AGA AAG CAG ATG AAA GAA ATT ATA | | 891 |
| Gly Pro Ser Glu Ile Pro Ile Gln Arg Lys Gln Met Lys Glu Ile Ile | | |
| 235 240 245 | | |
| TTT TCC TTG CTG CCT GCA TGC AAA GAT CCT GAT CCT GAC ACT GGC ATT | | 939 |
| Phe Ser Leu Leu Pro Ala Cys Lys Asp Pro Asp Pro Asp Thr Gly Ile | | |
| 250 255 260 | | |
| CCT TTC AAA GTG GAT GCA ATT ATT GCT AAT CCA CCG GCA TAT GGA CAT | | 987 |
| Pro Phe Lys Val Asp Ala Ile Ile Ala Asn Pro Pro Ala Tyr Gly His | | |
| 265 270 275 280 | | |

```
ACA CAC GTG GCA GAG GCG CTA AAA GTA CCC ATT CAT ATA TTC TTT ACC      1035
Thr His Val Ala Glu Ala Leu Lys Val Pro Ile His Ile Phe Phe Thr
            285                 290                 295

ATG CCA TGG ACG CCA ACT AGT GAA TTT CCT CAT CCT CTT TCT CGC GTG      1083
Met Pro Trp Thr Pro Thr Ser Glu Phe Pro His Pro Leu Ser Arg Val
            300                 305                 310

AAA ACA TCA GCT GGA TAT CGA CTT TCT TAC CAA ATT GTT GAC TCC ATG      1131
Lys Thr Ser Ala Gly Tyr Arg Leu Ser Tyr Gln Ile Val Asp Ser Met
            315                 320                 325

ATT TGG CTT GGG ATA CGG GAT ATG ATA AAT GAA TTC AGG AAA AAG AAG      1179
Ile Trp Leu Gly Ile Arg Asp Met Ile Asn Glu Phe Arg Lys Lys Lys
            330                 335                 340

TTG AAG CTA CGC CCA GTA ACA TAC CTA AGT GGT TCA CAG GGT TCT GGA      1227
Leu Lys Leu Arg Pro Val Thr Tyr Leu Ser Gly Ser Gln Gly Ser Gly
345                 350                 355                 360

AGT GAC ATT CCT CAT GGA TAC ATC TGG AGT CCT CAT CTT GTC CCA AAA      1275
Ser Asp Ile Pro His Gly Tyr Ile Trp Ser Pro His Leu Val Pro Lys
            365                 370                 375

CCA AAA GAC TGG GGC CCC AAG ATT GAT GTT GTT GGA TTC TGC TTC CTC      1323
Pro Lys Asp Trp Gly Pro Lys Ile Asp Val Val Gly Phe Cys Phe Leu
            380                 385                 390

GAT CTT GCT TCT GAT TAC GAA CCA CCT GAA GAA CTC GTG AAA TGG CTT      1371
Asp Leu Ala Ser Asp Tyr Glu Pro Pro Glu Glu Leu Val Lys Trp Leu
            395                 400                 405

GAA GCT GGT GAC AAG CCC ATT TAT GTT GGT TTC GGT AGC CTT CCA GTT      1419
Glu Ala Gly Asp Lys Pro Ile Tyr Val Gly Phe Gly Ser Leu Pro Val
            410                 415                 420

CAA GAT CCA ACA AAG ATG ACT GAA ACC ATT ATC CAA GCA CTT GAA ATG      1467
Gln Asp Pro Thr Lys Met Thr Glu Thr Ile Ile Gln Ala Leu Glu Met
425                 430                 435                 440

ACC GGA CAG AGA GGT ATT ATT AAC AAA GGT TGG GGT GGC CTC GGA ACC      1515
Thr Gly Gln Arg Gly Ile Ile Asn Lys Gly Trp Gly Gly Leu Gly Thr
            445                 450                 455

TTG GCA GAA CCG AAA GAT TCC ATA TAT GTA CTT GAC AAC TGC CCT CAT      1563
Leu Ala Glu Pro Lys Asp Ser Ile Tyr Val Leu Asp Asn Cys Pro His
            460                 465                 470

GAC TGG CTT TTC CTG CAG TGT AAG GCA GTG GTG CAT CAT GGT GGA GCT      1611
Asp Trp Leu Phe Leu Gln Cys Lys Ala Val Val His His Gly Gly Ala
            475                 480                 485

GGA ACG ACA GCT GCC GGC CTG AAA GCA GCG TGC CCT ACA ACT ATT GTA      1659
Gly Thr Thr Ala Ala Gly Leu Lys Ala Ala Cys Pro Thr Thr Ile Val
            490                 495                 500

CCT TTC TTT GGC GAC CAA CAA TTC TGG GGA GAC CGG GTG CAT GCT CGA      1707
Pro Phe Phe Gly Asp Gln Gln Phe Trp Gly Asp Arg Val His Ala Arg
505                 510                 515                 520

GGG GTA GGG CCT GTG CCT ATA CCA GTT GAA CAA TTC AAT TTG CAG AAA      1755
Gly Val Gly Pro Val Pro Ile Pro Val Glu Gln Phe Asn Leu Gln Lys
            525                 530                 535

CTG GTT GAT GCT ATG AAG TTC ATG TTG GAG CCA GAG GTA AAA GAA AAG      1803
Leu Val Asp Ala Met Lys Phe Met Leu Glu Pro Glu Val Lys Glu Lys
            540                 545                 550

GCT GTG GAG CTT GCC AAG GCC ATG GAA TCT GAG GAT GGT GTA ACC GGT      1851
Ala Val Glu Leu Ala Lys Ala Met Glu Ser Glu Asp Gly Val Thr Gly
            555                 560                 565

GCA GTT AGG GCA TTC CTC AAA CAT CTG CCT TCT TCA AAA GAA GAT GAA      1899
Ala Val Arg Ala Phe Leu Lys His Leu Pro Ser Ser Lys Glu Asp Glu
            570                 575                 580

AAT TCA CCC CCA CCT ACG CCG CAT GGT TTC CTA GAG TTC CTA GGC CCG      1947
Asn Ser Pro Pro Pro Thr Pro His Gly Phe Leu Glu Phe Leu Gly Pro
```

```
585                590                595                600
GTA AGT AAA TGT TTG GGG TGC TCT TAGGTGCTGA TTAGATGAAG GTATCACCAT         2001
Val Ser Lys Cys Leu Gly Cys Ser
                605

TCCTCCCTGC AAAAGGAAGT GATTAAGGAA AAAAGGCTGT TGGGTGACTG AGCTATGCG         2061

TTTTGTGCGA CAAGAATGTG GAAGCCCATG TAAGAAGTTG AAGAACATCC AGCCAGGAT         2121

GCGCGCTTTA TCGTTTCGCA TCGTTCGTTT GTTGGTTTTT GTTGTTGTGT AAAGAATAT         2181

TGTCTCTGTA ATTTGATACA TCATTTTGGT GTGGTTGCAA CCTTGGTGTG CAGCAACCA         2241

TGATCTCACA TGTATGACCA GGCATCTGTG TATATGGAAA ACTTTAAGAG GCAGATTAA         2301

AAAAAAAAAA AAAAA                                                         2317
```

(2) INFORMATION FOR SEQ ID NO: 4:

(i) SEQUENCE CHARACTERISTICS:
        (A) LENGTH: 608 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Ala Asp Ala Glu Pro Thr Gly Gly Gly Lys Gly Ala Glu Asp
 1               5                  10                  15

Ile Gly Gly Ala Ala Glu Ala His Ser Arg Asp Ser Pro Ala Ser
                20                  25                  30

Ala Leu Pro Thr Ala Pro Ser Thr Ser Ser Ser Ala Asp Asn Gly
                35                  40                  45

Asn Leu His Arg Ser Ser Thr Met Pro Gly Val Ile Lys Asp Ala Glu
     50                  55                  60

Ile Ile Thr Glu Thr Thr Gly Pro Ser Asn Phe Glu Arg Ser Lys Thr
 65                  70                  75                  80

Glu Arg Arg Arg Gln Asn Asn Asp Pro Ala Lys Gln Leu Leu Asp Asp
                 85                  90                  95

Lys Ile Ser Val Arg Lys Lys Leu Lys Met Leu Asn Arg Ile Ala Thr
                100                 105                 110

Val Arg Asp Asp Gly Thr Val Val Asp Val Pro Ser Ser Leu Asp
                115                 120                 125

Leu Ala Pro Leu Asp Val Gly Gly Glu Asp Gly Tyr Gly Asp Val Thr
     130                 135                 140

Val Glu Glu Ser Leu Asp Gly Ala Asp Ile Pro Ser Ile Pro Pro Met
145                 150                 155                 160

Gln Ile Val Ile Leu Ile Val Gly Thr Arg Gly Asp Val Gln Pro Phe
                165                 170                 175

Val Ala Ile Ala Lys Arg Leu Gln Asp Tyr Gly His Arg Val Arg Leu
                180                 185                 190

Ala Thr His Ala Asn Tyr Lys Glu Phe Val Leu Thr Ala Gly Leu Glu
                195                 200                 205

Phe Phe Pro Leu Gly Gly Asp Pro Lys Leu Leu Ala Glu Tyr Met Val
     210                 215                 220

Lys Asn Lys Gly Phe Leu Pro Ser Gly Pro Ser Glu Ile Pro Ile Gln
225                 230                 235                 240

Arg Lys Gln Met Lys Glu Ile Ile Phe Ser Leu Leu Pro Ala Cys Lys
                245                 250                 255

Asp Pro Asp Pro Asp Thr Gly Ile Pro Phe Lys Val Asp Ala Ile Ile
```

|   |   |   | 260 |   |   |   | 265 |   |   |   | 270 |   |
|---|---|---|---|---|---|---|---|---|---|---|---|---|

Ala Asn Pro Pro Ala Tyr Gly His Thr His Val Ala Glu Ala Leu Lys
              275                 280                 285

Val Pro Ile His Ile Phe Phe Thr Met Pro Trp Thr Pro Thr Ser Glu
    290                 295                 300

Phe Pro His Pro Leu Ser Arg Val Lys Thr Ser Ala Gly Tyr Arg Leu
305                 310                 315                 320

Ser Tyr Gln Ile Val Asp Ser Met Ile Trp Leu Gly Ile Arg Asp Met
                325                 330                 335

Ile Asn Glu Phe Arg Lys Lys Leu Lys Leu Arg Pro Val Thr Tyr
              340                 345                 350

Leu Ser Gly Ser Gln Gly Ser Gly Ser Asp Ile Pro His Gly Tyr Ile
    355                 360                 365

Trp Ser Pro His Leu Val Pro Lys Pro Lys Asp Trp Gly Pro Lys Ile
    370                 375                 380

Asp Val Val Gly Phe Cys Phe Leu Asp Leu Ala Ser Asp Tyr Glu Pro
385                 390                 395                 400

Pro Glu Glu Leu Val Lys Trp Leu Glu Ala Gly Asp Lys Pro Ile Tyr
              405                 410                 415

Val Gly Phe Gly Ser Leu Pro Val Gln Asp Pro Thr Lys Met Thr Glu
              420                 425                 430

Thr Ile Ile Gln Ala Leu Glu Met Thr Gly Gln Arg Gly Ile Ile Asn
              435                 440                 445

Lys Gly Trp Gly Gly Leu Gly Thr Leu Ala Glu Pro Lys Asp Ser Ile
    450                 455                 460

Tyr Val Leu Asp Asn Cys Pro His Asp Trp Leu Phe Leu Gln Cys Lys
465                 470                 475                 480

Ala Val Val His His Gly Gly Ala Gly Thr Thr Ala Ala Gly Leu Lys
              485                 490                 495

Ala Ala Cys Pro Thr Thr Ile Val Pro Phe Phe Gly Asp Gln Gln Phe
              500                 505                 510

Trp Gly Asp Arg Val His Ala Arg Gly Val Gly Pro Val Pro Ile Pro
    515                 520                 525

Val Glu Gln Phe Asn Leu Gln Lys Leu Val Asp Ala Met Lys Phe Met
    530                 535                 540

Leu Glu Pro Glu Val Lys Glu Lys Ala Val Glu Leu Ala Lys Ala Met
545                 550                 555                 560

Glu Ser Glu Asp Gly Val Thr Gly Ala Val Arg Ala Phe Leu Lys His
              565                 570                 575

Leu Pro Ser Ser Lys Glu Asp Glu Asn Ser Pro Pro Thr Pro His
              580                 585                 590

Gly Phe Leu Glu Phe Leu Gly Pro Val Ser Lys Cys Leu Gly Cys Ser
    595                 600                 605

(2) INFORMATION FOR SEQ ID NO: 5:

(i) SEQUENCE CHARACTERISTICS:
        (A) LENGTH: 360 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO: 5:

CTTGATGTTG GAGGAGAGGA TGGCTATGGT GATGTCACTG TTGAAGAATC ATTGGATGGA    60

```
GCAGATATAC CATCCATACC TCCTATGCAG ATTGTTATAC TTATTGTGGG TACAAGGGGA      120

GATGTTCAGC CATTTGTTGC TATAGCAAAA CGCTTACAGG ATTATGGACA CCGTGTGAGA      180

TTAGCCACTC ATGCCAACTA TAAGGAGTTC GTACTGACAG CTGGGCTGGA GTTTTTCCCA      240

CTTGGTGGAG ATCCAAAACT ACTTGCTGAA TACATGGTGA AGAATAAAGG GTTCCTGCCT      300

TCAGGCCCAT CAGAAATTCC TATTCAAAGA AAGCAGATGA AGAAATTAT ATTTTCCTTG       360

(2) INFORMATION FOR SEQ ID NO: 6:

(i) SEQUENCE CHARACTERISTICS:
        (A) LENGTH: 300 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO: 6:

TACCTAAGTG GTTCACAGGG TTCTGGAAGT GACATTCCTC ATGGATACAT CTGGAGTCCT       60

CATCTTGTCC CAAAACCAAA AGACTGGGGC CCCAAGATTG ATGTTGTTGG ATTCTGCTTC      120

CTCGATCTTG CTTCTGATTA CGAACCACCT GAAGAACTCG TGAAATGGCT TGAAGCTGGT      180

GACAAGCCCA TTTATGTTGG TTTCGGTAGC CTTCCAGTTC AAGATCCAAC AAAGATGACT      240

GAAACCATTA TCCAAGCACT TGAAATGACC GGACAGAGAG GTATTATTAA CAAAGGTTGG      300

(2) INFORMATION FOR SEQ ID NO: 7:

(i) SEQUENCE CHARACTERISTICS:
        (A) LENGTH: 657 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 7:

Arg Ile Leu Arg Leu Leu Ile Pro His Leu Val Gly Arg Ser Phe Pro
1               5                  10                  15

Pro Pro Arg Arg Asn Ser Arg Arg Ser Arg Arg Ser Asn Arg Arg
            20                  25                  30

Ala Lys Ser Gly Ile Ser Gly Pro Thr Gly Gln Thr Ala Gly Ala Val
        35                  40                  45

Gln Met Ala Asp Ala Glu Pro Thr Gly Val Gly Lys Gly Ala Glu
    50                  55                  60

Asp Ile Gly Gly Ala Ala Glu Ala His Ser Arg Asp Ser Pro Ala Ser
65                  70                  75                  80

Ala Ala Leu Pro Thr Ala Pro Ser Thr Ser Ser Ser Ala Asp Asn
            85                  90                  95

Gly Asn Leu His Arg Ser Ser Thr Met Pro Gly Val Ile Lys Asp Ala
                100                 105                 110

Glu Ile Ile Thr Glu Thr Thr Gly Pro Ser Asn Phe Glu Arg Ser Lys
            115                 120                 125

Thr Glu Arg Arg Arg Gln Asn Asn Asp Pro Ala Lys Gln Leu Leu Asp
        130                 135                 140

Asp Lys Ile Ser Val Arg Lys Lys Leu Lys Met Leu Asn Arg Ile Ala
145                 150                 155                 160

Thr Val Arg Asp Asp Gly Thr Val Val Asp Val Pro Ser Ser Leu
                165                 170                 175
```

-continued

```
Asp Leu Ala Pro Leu Asp Val Gly Gly Glu Asp Ala Tyr Gly Asp Val
            180                 185                 190
Thr Val Glu Glu Ser Leu Asp Gly Ala Asp Ile Pro Ser Ile Pro Pro
        195                 200                 205
Met Gln Ile Val Ile Leu Ile Val Gly Thr Arg Gly Asp Val Gln Pro
    210                 215                 220
Phe Val Ala Ile Ala Lys Arg Leu Gln Asp Tyr Gly His Arg Val Arg
225                 230                 235                 240
Leu Ala Thr His Ala Asn Tyr Lys Glu Phe Val Leu Thr Ala Gly Leu
            245                 250                 255
Glu Phe Phe Pro Leu Gly Gly Asp Pro Lys Leu Leu Ala Lys Tyr Met
            260                 265                 270
Val Lys Asn Lys Gly Phe Leu Pro Ser Gly Pro Ser Glu Ile Pro Ile
        275                 280                 285
Gln Arg Lys Gln Met Lys Glu Ile Ile Phe Ser Leu Leu Pro Ala Cys
    290                 295                 300
Lys Asp Pro Asp Pro Asp Thr Gly Ile Pro Phe Lys Val Asp Ala Ile
305                 310                 315                 320
Ile Ala Asn Pro Pro Ala Tyr Gly His Thr His Val Ala Glu Ala Leu
            325                 330                 335
Lys Val Pro Ile His Ile Phe Phe Thr Met Pro Trp Thr Pro Thr Ser
            340                 345                 350
Glu Phe Pro His Pro Leu Ser Arg Val Lys Thr Ser Ala Gly Tyr Arg
            355                 360                 365
Leu Ser Tyr Gln Ile Val Asp Ser Met Ile Trp Leu Gly Ile Arg Asp
    370                 375                 380
Met Ile Asn Glu Phe Arg Lys Lys Leu Lys Leu Arg Pro Val Thr
385                 390                 395                 400
Tyr Leu Ser Gly Ser Gln Gly Ser Gly Ser Asp Ile Pro His Gly Tyr
            405                 410                 415
Ile Trp Ser Pro His Leu Val Pro Lys Pro Lys Asp Trp Gly Pro Lys
            420                 425                 430
Ile Asp Val Val Gly Phe Cys Phe Leu Asp Leu Ala Ser Asp Tyr Glu
    435                 440                 445
Pro Pro Glu Glu Leu Val Lys Trp Leu Glu Ala Gly Asp Lys Pro Ile
450                 455                 460
Tyr Val Gly Phe Gly Ser Leu Pro Val Gln Asp Pro Thr Lys Met Thr
465                 470                 475                 480
Glu Thr Ile Ile Gln Ala Leu Glu Met Thr Gly Gln Arg Gly Ile Ile
            485                 490                 495
Asn Lys Gly Trp Gly Gly Leu Gly Thr Leu Ala Glu Pro Lys Asp Ser
            500                 505                 510
Ile Tyr Val Leu Asp Asn Cys Pro His Asp Trp Leu Phe Leu Gln Cys
    515                 520                 525
Lys Ala Val Val His His Gly Ala Gly Thr Thr Ala Ala Gly Leu
            530                 535                 540
Lys Ala Ala Cys Pro Thr Thr Ile Val Pro Phe Phe Gly Asp Gln Gln
545                 550                 555                 560
Phe Trp Gly Asp Arg Val His Ala Arg Gly Val Gly Pro Val Pro Ile
            565                 570                 575
Pro Val Glu Gln Phe Asn Leu Gln Lys Leu Val Asp Ala Met Lys Phe
            580                 585                 590
```

```
Met Leu Glu Pro Glu Val Lys Glu Lys Pro Val Glu Leu Ala Lys Pro
        595                 600                 605

Met Glu Ser Glu Asp Gly Val Thr Gly Ala Val Arg Ala Phe Leu Lys
        610                 615                 620

His Leu Pro Ser Ser Lys Glu Asp Glu Asn Ser Pro Pro Thr Pro
625                 630                 635                 640

His Gly Phe Leu Glu Phe Leu Gly Pro Val Ser Lys Cys Leu Gly Cys
                    645                 650                 655

Ser
```

(2) INFORMATION FOR SEQ ID NO: 8:

(i) SEQUENCE CHARACTERISTICS:
        (A) LENGTH: 15 amino acids
        (B) TYPE: amino acid
        (C) STRANDEDNESS: unknown
        (D) TOPOLOGY: unknown (ii) MOLECULE TYPE: peptide (v) FRAGMENT TYPE: N-terminal (xi) SEQUENCE DESCRIPTION: SEQ ID NO: 8:

```
Asp Val Gly Gly Glu Asp Gly Tyr Gly Asp Val Thr Val Glu Glu
1               5                   10                  15
```

(2) INFORMATION FOR SEQ ID NO: 9:

(i) SEQUENCE CHARACTERISTICS:
        (A) LENGTH: 20 amino acids
        (B) TYPE: amino acid
        (C) STRANDEDNESS: unknown
        (D) TOPOLOGY: unknown (ii) MOLECULE TYPE: peptide (v) FRAGMENT TYPE: N-terminal (xi) SEQUENCE DESCRIPTION: SEQ ID NO: 9:

```
Leu Asp Val Gly Gly Glu Asp Ala Tyr Gly Asp Val Thr Val Glu Glu
1               5                   10                  15

Ser Leu Asp Gly
            20
```

(2) INFORMATION FOR SEQ ID NO: 10:

(i) SEQUENCE CHARACTERISTICS:
        (A) LENGTH: 1198 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 10:

```
Met Pro Ile Thr Gln Ile Ile Ser Ala Ser Asp Ser Glu Ala Gly Pro
1               5                   10                  15

Lys Pro Ser Ile Ser Leu Val Pro Asp Lys Pro Ser Glu Pro Glu Thr
                20                  25                  30

Ser Pro Arg His His Arg Leu Ser Arg Ser Leu Ser Lys Phe Lys Arg
            35                  40                  45

Trp Arg Gly Arg Ser Asn Ser Ser Leu Ser Met Gly Ser Ser Glu Gln
        50                  55                  60

Gln Glu Leu Gln Asp Ser Pro Asn Glu Ala Arg Ser Asp Asp Asp Glu
```

-continued

```
 65                   70                  75                  80
Asn Gly Tyr Asn Asn Asp Asn Ala Asp Asp Leu Ala Lys Ser Lys Tyr
                 85                  90                  95
Met Met Lys Ser Ile Ala Gly Leu Leu Thr Thr Ala Ser Val Tyr Ala
            100                 105                 110
Gly Met Asn Asn Ala Gln Glu Met Asn Val Leu Ser Gln Val Asp Ser
            115                 120                 125
Glu Glu Ser Asp Ser Ser Asp Ser Phe Gln Glu Asn Ile Gly Arg Asn
        130                 135                 140
Glu Val Lys Ser Lys Lys Glu Asn Leu Lys Thr Lys Ser His Pro Glu
145                 150                 155                 160
Val Pro Arg Leu Asp Lys Arg Lys Pro Thr Leu Phe Asp Phe Ser Ile
                165                 170                 175
Thr Arg Glu Lys Leu Ser Lys Asp Asn Val Ala Lys Leu Arg Gln Arg
            180                 185                 190
Phe Cys Leu Asp Glu Gln Glu Pro Phe Leu Asn Asp Phe Pro Ala Trp
            195                 200                 205
Leu Leu Lys Asp Val Leu Val Gln Gly His Ile Phe Ile Thr Thr Lys
    210                 215                 220
His Phe Leu Phe Phe Ala Tyr Leu Pro Lys Asn Pro Arg Ser Val Lys
225                 230                 235                 240
Met Ser Gly Asn Leu Asn Ile Arg Thr Lys Leu Ile Arg Ser Thr Arg
                245                 250                 255
Tyr Trp Cys Val Leu Lys Asn His Leu Phe Ser Met Tyr Thr Ser Ser
                260                 265                 270
Thr Glu Leu Tyr Phe Pro Val Leu Thr Ile Asp Leu Arg Glu Val Gln
            275                 280                 285
Lys Ile Glu Thr Gln Lys His Thr Leu Asn Gly Ser Ala Thr Lys Thr
        290                 295                 300
Phe Lys Leu Tyr Thr Asp Glu Ser Thr Phe Lys Phe Asn Ala Asp Ser
305                 310                 315                 320
Glu Phe Ser Ala Lys Ser Trp Val Asn Ala Leu Lys Lys Glu Gln Phe
                325                 330                 335
Ala Ala Gln Asn Ser Glu Asn Asn Ser Ile Ser Leu Lys Ile Pro Leu
            340                 345                 350
Pro Asn Ile Ile Glu Ile Asp Asp Gln Pro Ile Val Asn Lys Ala Leu
            355                 360                 365
Thr Leu Arg Leu Arg Ala Leu Glu Ser Ser Gln Thr Tyr Ala Ile Asp
    370                 375                 380
Asp Phe Met Phe Val Phe Met Asp Gly Ser Gly Ser Gln Val Lys Glu
385                 390                 395                 400
Ser Leu Gly Glu Gln Leu Ala Ile Leu Gln Lys Ser Gly Val Asn Thr
                405                 410                 415
Leu Tyr Tyr Asp Ile Pro Ala Lys Lys Ser Lys Ser Ser Phe Gly Lys
            420                 425                 430
Glu Thr Pro Ala Thr Val Glu Gln Lys Asn Asn Gly Glu Asp Ser Lys
        435                 440                 445
Tyr Leu Asn Val Pro Thr Ser Ala Val Pro Ser Ser Glu Asn Gly Lys
    450                 455                 460
Lys Ser Arg Phe Arg Phe Arg Glu Arg Ser Asn Ser Trp Phe Arg Arg
465                 470                 475                 480
Ala Lys Pro Leu Glu Asp Ser Gln Val Glu Asp Val Glu Ile Tyr
                485                 490                 495
```

-continued

```
Lys Asp Ala Ala Asn Asp Ile Asp Ser Ser Val His Ser Thr Ile His
                500                 505                 510
Ile His Glu Gln Glu Asp Ser Gln Glu Gln Thr Val Ala Trp Lys Pro
            515                 520                 525
Ser His Leu Lys Asn Phe Ala Glu Met Trp Ala Ala Lys Pro Ile His
            530                 535                 540
Tyr Arg Asn Lys Phe Ile Pro Phe Gln Lys Asp Asp Thr Tyr Leu Ile
545                 550                 555                 560
Lys Glu Thr Glu Glu Val Ser Ala Asn Glu Arg Phe Arg Tyr His Phe
                565                 570                 575
Lys Phe Asn Lys Glu Lys Ser Leu Ile Ser Thr Tyr Tyr Thr Tyr Leu
            580                 585                 590
Asn Arg Asn Val Pro Val Tyr Gly Lys Ile Tyr Val Ser Asn Asp Thr
            595                 600                 605
Val Cys Phe Arg Ser Leu Leu Pro Gly Ser Asn Thr Tyr Met Val Leu
            610                 615                 620
Pro Leu Val Asp Val Glu Thr Cys Tyr Lys Glu Lys Gly Phe Arg Phe
625                 630                 635                 640
Gly Tyr Phe Val Leu Val Ile Val Ile His Gly His Glu Glu Leu Phe
                645                 650                 655
Phe Glu Phe Ser Thr Glu Val Ala Arg Asp Asp Ile Glu Arg Ile Leu
                660                 665                 670
Leu Lys Leu Leu Asp Asn Ile Tyr Ala Ser Ser Ala Glu Gly Ser Asn
            675                 680                 685
Ile Ser Ser Ala Ser Leu Gly Asp Val Gln His Asn Pro Asp Ser Ala
            690                 695                 700
Lys Leu Lys Leu Phe Glu Asp Lys Ile Asn Ala Glu Gly Phe Glu Val
705                 710                 715                 720
Pro Leu Met Ile Asp Glu Asn Pro His Tyr Lys Thr Ser Ile Lys Pro
                725                 730                 735
Asn Lys Ser Tyr Lys Phe Gly Leu Leu Thr Ile Gly Ser Arg Gly Asp
            740                 745                 750
Val Gln Pro Tyr Ile Ala Leu Gly Lys Gly Leu Ile Lys Glu Gly His
            755                 760                 765
Gln Val Val Ile Ile Thr His Ser Glu Phe Arg Asp Phe Val Glu Ser
            770                 775                 780
His Gly Ile Gln Phe Glu Glu Ile Ala Gly Asn Pro Val Glu Leu Met
785                 790                 795                 800
Ser Leu Met Val Glu Asn Glu Ser Met Asn Val Lys Met Leu Arg Glu
                805                 810                 815
Ala Ser Ser Lys Phe Arg Gly Trp Ile Asp Ala Leu Leu Gln Thr Ser
            820                 825                 830
Trp Glu Val Cys Asn Arg Arg Lys Phe Asp Ile Leu Ile Glu Ser Pro
            835                 840                 845
Ser Ala Met Val Gly Ile His Ile Thr Glu Ala Leu Gln Ile Pro Tyr
            850                 855                 860
Phe Arg Ala Phe Thr Met Pro Trp Thr Arg Thr Arg Ala Tyr Pro His
865                 870                 875                 880
Ala Phe Ile Val Pro Asp Gln Lys Arg Gly Gly Asn Tyr Asn Tyr Leu
                885                 890                 895
Thr His Val Leu Phe Glu Asn Val Phe Trp Lys Gly Ile Ser Gly Gln
            900                 905                 910
```

-continued

```
Val Asn Lys Trp Arg Val Glu Thr Leu Gly Leu Gly Lys Thr Asn Leu
          915                 920                 925

Phe Leu Leu Gln Gln Asn Asn Val Pro Phe Leu Tyr Asn Val Ser Pro
      930                 935                 940

Thr Ile Phe Pro Pro Ser Ile Asp Phe Ser Glu Trp Val Arg Val Thr
945                 950                 955                 960

Gly Tyr Trp Phe Leu Asp Asp Lys Ser Thr Phe Lys Pro Pro Ala Glu
              965                 970                 975

Leu Gln Glu Phe Ile Ser Glu Ala Arg Ser Lys Gly Lys Lys Leu Val
          980                 985                 990

Tyr Ile Gly Phe Gly Ser Ile Val Val Ser Asn Ala Lys Glu Met Thr
      995                 1000                1005

Glu Ala Leu Val Glu Ala Val Met Glu Ala Asp Val Tyr Cys Ile Leu
     1010                1015                1020

Asn Lys Gly Trp Ser Glu Arg Leu Gly Asp Lys Ala Ala Lys Lys Thr
1025                1030                1035                1040

Glu Val Asp Leu Pro Arg Asn Ile Leu Asn Ile Gly Asn Val Pro His
              1045                1050                1055

Asp Trp Leu Phe Pro Gln Val Asp Ala Ala Val His His Gly Gly Ser
          1060                1065                1070

Gly Thr Thr Gly Ala Ser Leu Arg Ala Gly Leu Pro Thr Val Ile Lys
     1075                1080                1085

Pro Phe Phe Gly Asp Gln Phe Phe Tyr Ala Gly Arg Val Glu Asp Ile
1090                1095                1100

Gly Val Gly Ile Ala Leu Lys Lys Leu Asn Ala Gln Thr Leu Ala Asp
1105                1110                1115                1120

Ala Leu Lys Val Ala Thr Thr Asn Lys Ile Met Lys Asp Arg Ala Gly
              1125                1130                1135

Leu Ile Lys Lys Lys Ile Ser Lys Glu Asp Gly Ile Lys Thr Ala Ile
          1140                1145                1150

Ser Ala Ile Tyr Asn Glu Leu Glu Tyr Ala Arg Ser Val Thr Leu Ser
              1155                1160                1165

Arg Val Lys Thr Pro Arg Lys Lys Glu Glu Asn Val Asp Ala Thr Lys
     1170                1175                1180

Leu Thr Pro Ala Glu Thr Thr Asp Glu Gly Trp Thr Met Ile
1185                1190                1195
```

(2) INFORMATION FOR SEQ ID NO: 11:

(i) SEQUENCE CHARACTERISTICS:
        (A) LENGTH: 397 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO: 11:

```
GGGGGGATGT TCAGCCTTTT GTTGCAATAG CCAAACGGCT TCAGGACTAT GGCCATCGAG     60

TTAGACTTGC AACTCATGCA AATTTTAAAG AGTTTGTTTT GACTGCTGGA TTAGAGTTTT    120

ATCCTCTAGG TGGAGATCCA AAAGTGCTCG CCGGTTATAT GGTTAAGAAC AAGGGCTTTT    180

TGCCATCAGG CCCTTCAGAG ATTCCAATTC AACGAAACCA AATGAAGGAC ATCATATATG    240

CTCTACTTCC AGCATGTAAA GAACCTGATC CAGATTCTGG GATTTCCTTT AAAGCTGATG    300

CAATTATTGC CAACCCTCCA GCGTATGGAC ATACCCATGT GGCAGAAGCA CTGAAGATAC    360
```

```
CGATTCACGT ATTTTTCACC ATGCCCTGGA CCCCCAC                              397
```

(2) INFORMATION FOR SEQ ID NO: 12:

(i) SEQUENCE CHARACTERISTICS:
        (A) LENGTH: 401 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO: 12:

```
CGCGGGGGA TGTCCAGCCC TTTACTGCAA TTGGCAAGCG TCTGCAGGAT TTTGGCCATC       60
GAGTGAGGTT GGCGACCCAT GCAAATTTCA AGAGTTTGT CTTGAGTGCT GGATTGGAAT      120
TCTATCCCCT TGGGGGTGAT CCAAAAATTT TGGCTGGATA CATGGTAAAA ACAAAGGAT      180
TCTTACCTTC CGGACCTTCA GAAATCCCTG TTCAGAGAAA TCAGATGAAG GAGATTATAT     240
ACTCTCTACT TCCAGCCTGC AAAGAGCCTG ATATGGATAC AGGAGTTCCC TTCAAAGCAG     300
ATGCAATTAT TGCTAATCCC CCAGCATATG GGCATGTACA TGTTGCAGAA GCATTGCAAA     360
TCCCAATTCA TATATTTTTC ACCATGCCCT GGACCCCCAC A                         401
```

(2) INFORMATION FOR SEQ ID NO: 13:

(i) SEQUENCE CHARACTERISTICS:
        (A) LENGTH: 506 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO: 13:

```
GGTATTTCCG GACAAGTAAA TAAATGGAGA GTTGAGGAAT TAGATTTGCC AAAGACCAAT      60
TTATACAGGT TGCAACAGAC AAGGGTCCCC TTCTTGTATA ATGTTTCACC CGCTATATTA     120
CCGCCATCTG TTGATTTTCC TGATTGGATT AAAGTAACTG GATACTGGTT TTTAGATGAA     180
GGTTCTGGAG ATTACAAGCC ACCTGAAGAA CTTGTACAAT TTATGAAAAA AGCATCCCGT     240
GACAAAAAGA AGATTGTTTA CATTGGATTT GGTTCTATTG TAGTGAAAGA TGCAAAATCC     300
TTAACGAAAG CTGTGGTGTC TGCTGTGAGA AGAGCCGACG TTCGTTGTAT TTTAAACAAG     360
GGTTGGTCTG ATCGATTGGA TAATAAAGAT AAAAATGAAA TTGAAATTGA GTTGCCACCG     420
GAAATTTACA ATTCTGGAAC TATACCTCAT GATTGGTTGT TTCCGCGTAT TGATGCTGCC     480
GTGCACCATG CCGGCACCGG CACCAC                                         506
```

(2) INFORMATION FOR SEQ ID NO: 14:

(i) SEQUENCE CHARACTERISTICS:
        (A) LENGTH: 131 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 14:

```
Gly Asp Val Gln Pro Phe Val Ala Ile Ala Lys Arg Leu Gln Asp Tyr
1               5                  10                  15
Gly His Arg Val Arg Leu Ala Thr His Ala Asn Phe Lys Glu Phe Val
            20                  25                  30
```

```
Leu Thr Ala Gly Leu Glu Phe Tyr Pro Leu Gly Gly Asp Pro Lys Val
            35                  40                  45

Leu Ala Gly Tyr Met Val Lys Asn Lys Gly Phe Leu Pro Ser Gly Pro
        50                  55                  60

Ser Glu Ile Pro Ile Gln Arg Asn Gln Met Lys Asp Ile Ile Tyr Ser
65                  70                  75                  80

Leu Leu Pro Ala Cys Lys Glu Pro Asp Pro Asp Ser Gly Ile Ser Phe
                85                  90                  95

Lys Ala Asp Ala Ile Ile Ala Asn Pro Pro Ala Tyr Gly His Thr His
                100                 105                 110

Val Ala Glu Ala Leu Lys Ile Pro Ile His Val Phe Phe Thr Met Pro
            115                 120                 125

Trp Thr Pro
    130

(2) INFORMATION FOR SEQ ID NO: 15:

(i) SEQUENCE CHARACTERISTICS:
        (A) LENGTH: 180 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 15:

Leu Asp Val Gly Gly Glu Asp Ala Tyr Gly Asp Val Thr Val Glu Glu
1               5                   10                  15

Ser Leu Asp Gly Ala Asp Ile Pro Ser Ile Pro Pro Met Gln Ile Val
            20                  25                  30

Ile Leu Ile Val Gly Thr Arg Gly Asp Val Gln Pro Phe Val Ala Ile
            35                  40                  45

Ala Lys Arg Leu Gln Asp Tyr Gly His Arg Val Arg Leu Ala Thr His
        50                  55                  60

Ala Asn Tyr Lys Glu Phe Val Leu Thr Ala Gly Leu Glu Phe Phe Pro
65                  70                  75                  80

Leu Gly Gly Asp Pro Lys Leu Leu Ala Lys Tyr Met Val Lys Asn Lys
                85                  90                  95

Gly Phe Leu Pro Ser Gly Pro Ser Glu Ile Pro Ile Gln Arg Lys Gln
                100                 105                 110

Met Lys Glu Ile Ile Phe Ser Leu Leu Pro Ala Cys Lys Asp Pro Asp
            115                 120                 125

Pro Asp Thr Gly Ile Pro Phe Lys Val Asp Ala Ile Ile Ala Asn Pro
        130                 135                 140

Pro Ala Tyr Gly His Thr His Val Ala Glu Ala Leu Lys Val Pro Ile
145                 150                 155                 160

His Ile Phe Phe Thr Met Pro Trp Thr Pro Thr Ser Glu Phe Pro His
                165                 170                 175

Pro Leu Ser Arg
    180

(2) INFORMATION FOR SEQ ID NO: 16:

(i) SEQUENCE CHARACTERISTICS:
        (A) LENGTH: 133 amino acids
        (B) TYPE: amino acid
        (C) STRANDEDNESS: unknown
        (D) TOPOLOGY: unknown
```

```
       (ii) MOLECULE TYPE: protein (xi) SEQUENCE DESCRIPTION: SEQ ID NO: 16:

Arg Gly Asp Val Gln Pro Phe Thr Ala Ile Gly Lys Arg Leu Gln Asp
1               5                   10                  15

Phe Gly His Arg Val Arg Leu Ala Thr His Ala Asn Phe Lys Glu Phe
            20                  25                  30

Val Leu Ser Ala Gly Leu Glu Phe Tyr Pro Leu Gly Gly Asp Pro Lys
        35                  40                  45

Ile Leu Ala Gly Tyr Met Val Lys Asn Lys Gly Phe Leu Pro Ser Gly
    50                  55                  60

Pro Ser Glu Ile Pro Val Gln Arg Asn Gln Met Lys Glu Ile Ile Tyr
65                  70                  75                  80

Ser Leu Leu Pro Ala Cys Lys Glu Pro Asp Met Asp Thr Gly Val Pro
                85                  90                  95

Phe Lys Ala Asp Ala Ile Ile Ala Asn Pro Pro Ala Tyr Gly His Val
            100                 105                 110

His Val Ala Glu Ala Leu Gln Ile Pro Ile His Ile Phe Phe Thr Met
            115                 120                 125

Pro Trp Thr Pro Thr
            130

(2) INFORMATION FOR SEQ ID NO: 17:

(i) SEQUENCE CHARACTERISTICS:
           (A) LENGTH: 168 amino acids
           (B) TYPE: amino acid
           (C) STRANDEDNESS: unknown
           (D) TOPOLOGY: unknown (ii) MOLECULE TYPE: protein (xi) SEQUENCE DESCRIPTION: SEQ ID NO: 17:

Gly Ile Ser Gly Gln Val Asn Lys Trp Arg Val Glu Glu Leu Asp Leu
1               5                   10                  15

Pro Lys Thr Asn Leu Tyr Arg Leu Gln Gln Thr Arg Val Pro Phe Len
            20                  25                  30

Tyr Asn Val Ser Pro Ala Ile Leu Pro Pro Ser Val Asp Phe Pro Asp
        35                  40                  45

Trp Ile Lys Val Thr Gly Tyr Trp Phe Leu Asp Glu Gly Ser Gly Asp
    50                  55                  60

Tyr Lys Pro Pro Glu Glu Leu Val Gln Phe Met Lys Lys Ala Ser Arg
65                  70                  75                  80

Asp Lys Lys Lys Ile Val Tyr Ile Gly Phe Gly Ser Ile Val Val Lys
            85                  90                  95

Asp Ala Lys Ser Leu Thr Lys Ala Val Val Ser Ala Val Arg Arg Ala
            100                 105                 110

Asp Val Arg Cys Ile Leu Asn Lys Gly Trp Ser Asp Arg Leu Asp Asp
            115                 120                 125

Lys Asp Lys Asn Glu Ile Glu Ile Glu Leu Pro Pro Glu Ile Tyr Asn
            130                 135                 140

Ser Gly Thr Ile Pro His Asp Trp Leu Phe Pro Arg Ile Asp Ala Ala
145                 150                 155                 160

Val His His Ala Gly Thr Gly Thr
            165

(2) INFORMATION FOR SEQ ID NO: 18:
```

(i) SEQUENCE CHARACTERISTICS:
        (A) LENGTH: 179 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 18:

```
Phe Glu Asn Val Phe Trp Lys Gly Ile Ser Gly Gln Val Asn Lys Trp
1               5                   10                  15

Arg Val Glu Thr Leu Gly Leu Gly Lys Thr Asn Leu Phe Leu Leu Gln
                20                  25                  30

Gln Asn Asn Val Pro Phe Leu Tyr Asn Val Ser Pro Thr Ile Phe Pro
            35                  40                  45

Pro Ser Ile Asp Phe Ser Glu Trp Val Arg Val Thr Gly Tyr Trp Phe
    50                  55                  60

Leu Asp Asp Lys Ser Thr Phe Lys Pro Pro Ala Glu Leu Gln Glu Phe
65                  70                  75                  80

Ile Ser Glu Ala Arg Ser Lys Gly Lys Lys Leu Val Tyr Ile Gly Phe
                85                  90                  95

Gly Ser Ile Val Val Ser Asn Ala Lys Glu Met Thr Glu Ala Leu Val
            100                 105                 110

Glu Ala Val Met Glu Ala Asp Val Tyr Cys Ile Leu Asn Lys Gly Trp
        115                 120                 125

Ser Glu Arg Leu Gly Asp Lys Ala Lys Lys Thr Glu Val Asp Leu
    130                 135                 140

Pro Arg Asn Ile Leu Asn Ile Gly Asn Val Pro His Asp Trp Leu Phe
145                 150                 155                 160

Pro Gln Val Asp Ala Ala Val His His Gly Gly Ser Gly Thr Thr Gly
                165                 170                 175

Ala Ser Leu
```

(2) INFORMATION FOR SEQ ID NO: 19:

(i) SEQUENCE CHARACTERISTICS:
        (A) LENGTH: 2353 base pairs
        (B) TYPE: nucleic acid
        (C) STRANDEDNESS: unknown
        (D) TOPOLOGY: unknown (ii) MOLECULE TYPE: cDNA (ix) FEATURE:
        (A) NAME/KEY: CDS
        (B) LOCATION:113..2023

(xi) SEQUENCE DESCRIPTION: SEQ ID NO: 19:

```
ATTAATTCTC TCCTTCACTT TCTGGGATTC GAAACACGCA TACGCAAATT CGAGATACAC        60

GAAGAAAGGA TCCAGATCGT TTTCTGCTGG TGGAGATAGA GAGAGAATCA CG ATG CCG       118
                                                          Met Pro
                                                            1

GAA ATA TCG CCG GCT GAG CTC GCC AAG GTT TCT TCC TCG TCT TCT TCT        166
Glu Ile Ser Pro Ala Glu Leu Ala Lys Val Ser Ser Ser Ser Ser Ser
        5                   10                  15

TCT TCT TCC TCA AGT TCC GGC AGA GCG TCG GTG AAA ATC GAA GAG ATT        214
Ser Ser Ser Ser Ser Ser Gly Arg Ala Ser Val Lys Ile Glu Glu Ile
            20                  25                  30

GAA GGC GGT GCT GCT GCT AGT GGC GTC GTC ATT GTT TCT GAA GAA CTT        262
Glu Gly Gly Ala Ala Ala Ser Gly Val Val Ile Val Ser Glu Glu Leu
```

-continued

```
              35                     40                      45                     50
GAG ACC AAT CCC AAA ACT GTT GTT GCC TCC ATT GCT GAT GAA ACT GTC                310
Glu Thr Asn Pro Lys Thr Val Val Ala Ser Ile Ala Asp Glu Thr Val
                        55                      60                      65

GCT GAA TCT TCA GGT ACT GGC AAT AAA AGC TTT TCT CGA GTA TGG ACA                358
Ala Glu Ser Ser Gly Thr Gly Asn Lys Ser Phe Ser Arg Val Trp Thr
                70                      75                      80

ATG CCA TTG GAG GGT TCA TCG AGC AGT GAT AGG GCT GAA TCA TCA TCA                406
Met Pro Leu Glu Gly Ser Ser Ser Ser Asp Arg Ala Glu Ser Ser Ser
            85                      90                      95

ACA AAC CAA CCT AGG TTA GAT AAA TCA AAG ACT GAG AGG CAG CAA AAA                454
Thr Asn Gln Pro Arg Leu Asp Lys Ser Lys Thr Glu Arg Gln Gln Lys
        100                     105                     110

GTT ACT CAC ATT CTT GCT GAG GAT GCT GCT AAG ATT TTC GAT GAC AAA                502
Val Thr His Ile Leu Ala Glu Asp Ala Ala Lys Ile Phe Asp Asp Lys
115                     120                     125                     130

ATC TCT GCA GGG AAG AAG CTT AAA TTG CTG AAC CGT ATA GCT ACT GTG                550
Ile Ser Ala Gly Lys Lys Leu Lys Leu Leu Asn Arg Ile Ala Thr Val
                135                     140                     145

AAA CAT GAT GGG ACT GTT GAG TTT GAA GTT CCA GCA GAT GCT ATC CCT                598
Lys His Asp Gly Thr Val Glu Phe Glu Val Pro Ala Asp Ala Ile Pro
            150                     155                     160

CAA CCT ATT GTT GTT GAT CGT GGA GAA TCG AAA AAC GGT GTT TGC GCT                646
Gln Pro Ile Val Val Asp Arg Gly Glu Ser Lys Asn Gly Val Cys Ala
        165                     170                     175

GAT GAG TCT ATT GAC GGG GTT GAC CTT CAG TAT ATC CCT CCT ATG CAA                694
Asp Glu Ser Ile Asp Gly Val Asp Leu Gln Tyr Ile Pro Pro Met Gln
    180                     185                     190

ATT GTG ATG TTA ATT GTT GGA ACA CGT GGA GAT GTT CAA CCT TTT GTT                742
Ile Val Met Leu Ile Val Gly Thr Arg Gly Asp Val Gln Pro Phe Val
195                     200                     205                     210

GCA ATA GCC AAA CGG CTT CAG GAC TAT GGC CAT CGA GTT AGA CTT GCA                790
Ala Ile Ala Lys Arg Leu Gln Asp Tyr Gly His Arg Val Arg Leu Ala
                215                     220                     225

ACT CAT GCA AAT TTT AAA GAG TTT GTT TTG ACT GCT GGA TTA GAG TTT                838
Thr His Ala Asn Phe Lys Glu Phe Val Leu Thr Ala Gly Leu Glu Phe
            230                     235                     240

TAT CCT CTA GGT GGA GAT CCA AAA GTG CTC GCC GGT TAT ATG GTT AAG                886
Tyr Pro Leu Gly Gly Asp Pro Lys Val Leu Ala Gly Tyr Met Val Lys
        245                     250                     255

AAC AAG GGA TTT TTG CCA TCA GGC CCT TCA GAG ATT CCA ATT CAA CGA                934
Asn Lys Gly Phe Leu Pro Ser Gly Pro Ser Glu Ile Pro Ile Gln Arg
    260                     265                     270

AAC CAA ATG AAG GAC ATA ATA TAT TCT CTA CTT CCA GCA TGT AAA GAA                982
Asn Gln Met Lys Asp Ile Ile Tyr Ser Leu Leu Pro Ala Cys Lys Glu
275                     280                     285                     290

CCT GAT CCA GAT TCT GGG ATT TCC TTT AAA GCT GAT GCA ATT ATT GCC                1030
Pro Asp Pro Asp Ser Gly Ile Ser Phe Lys Ala Asp Ala Ile Ile Ala
                295                     300                     305

AAC CCT CCA GCG TAT GGA CAT ACC CAT GTG GCA GAA GCA CTG AAG ATA                1078
Asn Pro Pro Ala Tyr Gly His Thr His Val Ala Glu Ala Leu Lys Ile
            310                     315                     320

CCG ATT CAC GTA TTT TTC ACC ATG CCA TGG ACA CCA ACA AGT GAA TTT                1126
Pro Ile His Val Phe Phe Thr Met Pro Trp Thr Pro Thr Ser Glu Phe
        325                     330                     335

CCA CAC CCA TTG TCA CGT GTC AAA CAA CCA GCA GGA TAC AGA CTT TCA                1174
Pro His Pro Leu Ser Arg Val Lys Gln Pro Ala Gly Tyr Arg Leu Ser
    340                     345                     350

TAT CAA ATC GTC GAT TCA TTG ATC TGG CTT GGA ATA AGA GAT ATG GTA                1222
```

```
                                                                    -continued Tyr Gln Ile Val Asp Ser Leu Ile Trp Leu Gly Ile Arg Asp Met Val
355                 360                 365                 370

AAT GAC CTT AGG AAA AAG AAA TTG AAA CTA CGG CCT GTT ACA TAT CTA     1270
Asn Asp Leu Arg Lys Lys Lys Leu Lys Leu Arg Pro Val Thr Tyr Leu
                    375                 380                 385

AGT GGA ACA CAA GGA TCT GGA TCT AAT ATC CCA CAT GGA TAT ATG TGG     1318
Ser Gly Thr Gln Gly Ser Gly Ser Asn Ile Pro His Gly Tyr Met Trp
                390                 395                 400

AGT CCT CAC CTT GTA CCA AAG CCA AAA GAC TGG GGG CCT CAA ATT GAT     1366
Ser Pro His Leu Val Pro Lys Pro Lys Asp Trp Gly Pro Gln Ile Asp
            405                 410                 415

GTA GTG GGA TTT TGC TAT CTT GAT CTT GCA TCC AAC TAT GAA CCT CCT     1414
Val Val Gly Phe Cys Tyr Leu Asp Leu Ala Ser Asn Tyr Glu Pro Pro
        420                 425                 430

GCA GAG CTT GTG GAA TGG CTA GAA GCT GGT GAC AAG CCC ATA TAT ATC     1462
Ala Glu Leu Val Glu Trp Leu Glu Ala Gly Asp Lys Pro Ile Tyr Ile
435                 440                 445                 450

GGC TTT GGT AGT CTC CCT GTG CAA GAA CCA GAG AAA ATG ACA GAA ATC     1510
Gly Phe Gly Ser Leu Pro Val Gln Glu Pro Glu Lys Met Thr Glu Ile
                    455                 460                 465

ATT GTG GAA GCA CTT CAA AGA ACT AAA CAG AGA GGA ATC ATC AAC AAA     1558
Ile Val Glu Ala Leu Gln Arg Thr Lys Gln Arg Gly Ile Ile Asn Lys
                470                 475                 480

GGT TGG GGT GGC CTT GGA AAC TTG AAA GAA CCG AAG GAC TTT GTT TAC     1606
Gly Trp Gly Gly Leu Gly Asn Leu Lys Glu Pro Lys Asp Phe Val Tyr
            485                 490                 495

TTG TTG GAT AAT GTC CCA CAT GAC TGG CTA TTC CCG AGA TGC AAA GCT     1654
Leu Leu Asp Asn Val Pro His Asp Trp Leu Phe Pro Arg Cys Lys Ala
        500                 505                 510

GTG GTT CAT CAT GGT GGT GCT GGA ACA ACG GCT GCG GGT CTT AAA GCC     1702
Val Val His His Gly Gly Ala Gly Thr Thr Ala Ala Gly Leu Lys Ala
515                 520                 525                 530

TCG TGC CCA ACT ACA ATC GTG CCT TTC TTT GGA GAC CAA CCT TTT TGG     1750
Ser Cys Pro Thr Thr Ile Val Pro Phe Phe Gly Asp Gln Pro Phe Trp
                    535                 540                 545

GGA GAA CGA GTG CAT GCT AGA GGT GTT GGT CCT TCA CCA ATC CCA GTG     1798
Gly Glu Arg Val His Ala Arg Gly Val Gly Pro Ser Pro Ile Pro Val
                550                 555                 560

GAT GAA TTC TCA CTT CAT AAG CTT GAA GAT GCC ATA AAT TTC ATG CTC     1846
Asp Glu Phe Ser Leu His Lys Leu Glu Asp Ala Ile Asn Phe Met Leu
            565                 570                 575

GAC GAT AAG GTA AAG AGC AGT GCA GAG ACA CTA GCA AAG GCG ATG AAG     1894
Asp Asp Lys Val Lys Ser Ser Ala Glu Thr Leu Ala Lys Ala Met Lys
        580                 585                 590

GAC GAG GAT GGT GTG GCT GGA GCC GTG AAG GCC TTC TTT AAA CAT CTT     1942
Asp Glu Asp Gly Val Ala Gly Ala Val Lys Ala Phe Phe Lys His Leu
595                 600                 605                 610

CCA AGT GCA AAA CAG AAT ATC TCG GAT CCG ATC CCA GAA CCT TCT GGA     1990
Pro Ser Ala Lys Gln Asn Ile Ser Asp Pro Ile Pro Glu Pro Ser Gly
                    615                 620                 625

TTT CTC TCT TTC AGG AAA TGC TTT GGC TGT TCG TAACTTTCTT CTCTCCCTCC   2043
Phe Leu Ser Phe Arg Lys Cys Phe Gly Cys Ser
                630                 635

AGAATCTCCT CTTTTCTCTT TTGTATTGTT GTCTCTTGTA ATGTTTTTCT TCTTCGGTTT   2103

TGGCTATACA ACAACTTGCT TAGGAAAAGT TTTAACATTT GTGAAGTGCT TGGGAAATTT   2163

GCTGTTCTAG GGGATGCATA TATTATAAAA TTGTTATAAG CAGCAAAAAA AAAAAAAAAA   2223

AAAAATTCTG AAGATGTGCA GATTAGTGAA CATTGTTGTA TCGAGTTTTA ATATTATGAC   2283
```

```
ATATTTGTT TCAGTTTCTT GAGCTGCAAC TTCAAAAAAA AAAAAAAAAA AAAAAAAAAA    2343

AAAAAAAAAA                                                          2353
```

(2) INFORMATION FOR SEQ ID NO: 20:

(i) SEQUENCE CHARACTERISTICS:
        (A) LENGTH: 637 amino acids
        (B) TYPE: amino acid
        (D) TOPOLOGY: linear (ii) MOLECULE TYPE: protein (xi) SEQUENCE DESCRIPTION: SEQ ID NO: 20:

```
Met Pro Glu Ile Ser Pro Ala Glu Leu Ala Lys Val Ser Ser Ser
  1               5                  10                  15

Ser Ser Ser Ser Ser Ser Ser Gly Arg Ala Ser Val Lys Ile Glu
             20                  25                  30

Glu Ile Glu Gly Gly Ala Ala Ser Gly Val Val Ile Val Ser Glu
         35                  40                  45

Glu Leu Glu Thr Asn Pro Lys Thr Val Val Ala Ser Ile Ala Asp Glu
     50                  55                  60

Thr Val Ala Glu Ser Ser Gly Thr Gly Asn Lys Ser Phe Ser Arg Val
 65                  70                  75                  80

Trp Thr Met Pro Leu Glu Gly Ser Ser Ser Asp Arg Ala Glu Ser
                 85                  90                  95

Ser Ser Thr Asn Gln Pro Arg Leu Asp Lys Ser Lys Thr Glu Arg Gln
             100                 105                 110

Gln Lys Val Thr His Ile Leu Ala Glu Asp Ala Ala Lys Ile Phe Asp
         115                 120                 125

Asp Lys Ile Ser Ala Gly Lys Lys Leu Lys Leu Leu Asn Arg Ile Ala
 130                 135                 140

Thr Val Lys His Asp Gly Thr Val Glu Phe Glu Val Pro Ala Asp Ala
 145                 150                 155                 160

Ile Pro Gln Pro Ile Val Val Asp Arg Gly Glu Ser Lys Asn Gly Val
                 165                 170                 175

Cys Ala Asp Glu Ser Ile Asp Gly Val Asp Leu Gln Tyr Ile Pro Pro
             180                 185                 190

Met Gln Ile Val Met Leu Ile Val Gly Thr Arg Gly Asp Val Gln Pro
         195                 200                 205

Phe Val Ala Ile Ala Lys Arg Leu Gln Asp Tyr Gly His Arg Val Arg
 210                 215                 220

Leu Ala Thr His Ala Asn Phe Lys Glu Phe Val Leu Thr Ala Gly Leu
 225                 230                 235                 240

Glu Phe Tyr Pro Leu Gly Gly Asp Pro Lys Val Leu Ala Gly Tyr Met
                 245                 250                 255

Val Lys Asn Lys Gly Phe Leu Pro Ser Gly Pro Ser Glu Ile Pro Ile
             260                 265                 270

Gln Arg Asn Gln Met Lys Asp Ile Ile Tyr Ser Leu Leu Pro Ala Cys
         275                 280                 285

Lys Glu Pro Asp Pro Asp Ser Gly Ile Ser Phe Lys Ala Asp Ala Ile
 290                 295                 300

Ile Ala Asn Pro Pro Ala Tyr Gly His Thr His Val Ala Glu Ala Leu
 305                 310                 315                 320

Lys Ile Pro Ile His Val Phe Phe Thr Met Pro Trp Thr Pro Thr Ser
                 325                 330                 335
```

-continued

```
Glu Phe Pro His Pro Leu Ser Arg Val Lys Gln Pro Ala Gly Tyr Arg
            340                 345                 350

Leu Ser Tyr Gln Ile Val Asp Ser Leu Ile Trp Leu Gly Ile Arg Asp
        355                 360                 365

Met Val Asn Asp Leu Arg Lys Lys Leu Lys Leu Arg Pro Val Thr
370                 375                 380

Tyr Leu Ser Gly Thr Gln Gly Ser Gly Ser Asn Ile Pro His Gly Tyr
385                 390                 395                 400

Met Trp Ser Pro His Leu Val Pro Lys Pro Lys Asp Trp Gly Pro Gln
                405                 410                 415

Ile Asp Val Val Gly Phe Cys Tyr Leu Asp Leu Ala Ser Asn Tyr Glu
                420                 425                 430

Pro Pro Ala Glu Leu Val Glu Trp Leu Glu Ala Gly Asp Lys Pro Ile
            435                 440                 445

Tyr Ile Gly Phe Gly Ser Leu Pro Val Gln Glu Pro Glu Lys Met Thr
        450                 455                 460

Glu Ile Ile Val Glu Ala Leu Gln Arg Thr Lys Gln Arg Gly Ile Ile
465                 470                 475                 480

Asn Lys Gly Trp Gly Leu Gly Asn Leu Lys Glu Pro Lys Asp Phe
                485                 490                 495

Val Tyr Leu Leu Asp Asn Val Pro His Asp Trp Leu Phe Pro Arg Cys
            500                 505                 510

Lys Ala Val Val His His Gly Gly Ala Gly Thr Thr Ala Ala Gly Leu
            515                 520                 525

Lys Ala Ser Cys Pro Thr Thr Ile Val Pro Phe Phe Gly Asp Gln Pro
        530                 535                 540

Phe Trp Gly Glu Arg Val His Ala Arg Gly Val Gly Pro Ser Pro Ile
545                 550                 555                 560

Pro Val Asp Glu Phe Ser Leu His Lys Leu Glu Asp Ala Ile Asn Phe
                565                 570                 575

Met Leu Asp Asp Lys Val Lys Ser Ser Ala Glu Thr Leu Ala Lys Ala
            580                 585                 590

Met Lys Asp Glu Asp Gly Val Ala Gly Ala Val Lys Ala Phe Phe Lys
        595                 600                 605

His Leu Pro Ser Ala Lys Gln Asn Ile Ser Asp Pro Ile Pro Glu Pro
    610                 615                 620

Ser Gly Phe Leu Ser Phe Arg Lys Cys Phe Gly Cys Ser
625                 630                 635
```

(2) INFORMATION FOR SEQ ID NO: 21:

(i) SEQUENCE CHARACTERISTICS:
        (A) LENGTH: 674 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 21:

```
Leu Ile Leu Ser Phe Thr Phe Trp Asp Ser Lys His Ala Tyr Ala Asn
1               5                   10                  15

Ser Arg Tyr Thr Lys Lys Gly Ser Arg Ser Phe Ser Ala Gly Gly Asp
            20                  25                  30

Arg Glu Arg Ile Thr Met Pro Glu Ile Ser Pro Ala Glu Leu Ala Lys
        35                  40                  45
```

-continued

```
Val Ser Ser Ser Ser Ser Ser Ser Ser Ser Ser Gly Arg Ala
    50                  55                  60

Ser Val Lys Ile Glu Glu Ile Glu Gly Gly Ala Ala Ala Ser Gly Val
65                  70                  75                  80

Val Ile Val Ser Glu Glu Leu Glu Thr Asn Pro Lys Thr Val Val Ala
                85                  90                  95

Ser Ile Ala Asp Glu Thr Val Ala Glu Ser Ser Gly Thr Gly Asn Lys
            100                 105                 110

Ser Phe Ser Arg Val Trp Thr Met Pro Leu Glu Gly Ser Ser Ser Ser
        115                 120                 125

Asp Arg Ala Glu Ser Ser Thr Asn Gln Pro Arg Leu Asp Lys Ser
    130                 135                 140

Lys Thr Glu Arg Gln Gln Lys Val Thr His Ile Leu Ala Glu Asp Ala
145                 150                 155                 160

Ala Lys Ile Phe Asp Asp Lys Ile Ser Ala Gly Lys Lys Leu Lys Leu
                165                 170                 175

Leu Asn Arg Ile Ala Thr Val Lys His Asp Gly Thr Val Glu Phe Glu
            180                 185                 190

Val Pro Ala Asp Ala Ile Pro Gln Pro Ile Val Val Asp Arg Gly Glu
        195                 200                 205

Ser Lys Asn Gly Val Cys Ala Asp Glu Ser Ile Asp Gly Val Asp Leu
210                 215                 220

Gln Tyr Ile Pro Pro Met Gln Ile Val Met Leu Ile Val Gly Thr Arg
225                 230                 235                 240

Gly Asp Val Gln Pro Phe Val Ala Ile Ala Lys Arg Leu Gln Asp Tyr
                245                 250                 255

Gly His Arg Val Arg Leu Ala Thr His Ala Asn Phe Lys Glu Phe Val
            260                 265                 270

Leu Thr Ala Gly Leu Glu Phe Tyr Pro Leu Gly Gly Asp Pro Lys Val
        275                 280                 285

Leu Ala Gly Tyr Met Val Lys Asn Lys Gly Phe Leu Pro Ser Gly Pro
290                 295                 300

Ser Glu Ile Pro Ile Gln Arg Asn Gln Met Lys Asp Ile Ile Tyr Ser
305                 310                 315                 320

Leu Leu Pro Ala Cys Lys Glu Pro Asp Pro Asp Ser Gly Ile Ser Phe
                325                 330                 335

Lys Ala Asp Ala Ile Ile Ala Asn Pro Pro Ala Tyr Gly His Thr His
            340                 345                 350

Val Ala Glu Ala Leu Lys Ile Pro Ile His Val Phe Phe Thr Met Pro
        355                 360                 365

Trp Thr Pro Thr Ser Glu Phe Pro His Pro Leu Ser Arg Val Lys Gln
    370                 375                 380

Pro Ala Gly Tyr Arg Leu Ser Tyr Gln Ile Val Asp Ser Leu Ile Trp
385                 390                 395                 400

Leu Gly Ile Arg Asp Met Val Asn Asp Leu Arg Lys Lys Leu Lys
                405                 410                 415

Leu Arg Pro Val Thr Tyr Leu Ser Gly Thr Gln Gly Ser Gly Ser Asn
            420                 425                 430

Ile Pro His Gly Tyr Met Trp Ser Pro His Leu Val Pro Lys Pro Lys
        435                 440                 445

Asp Trp Gly Pro Gln Ile Asp Val Val Gly Phe Cys Tyr Leu Asp Leu
    450                 455                 460

Ala Ser Asn Tyr Glu Pro Pro Ala Glu Leu Val Glu Trp Leu Glu Ala
```

-continued

```
                465                 470                 475                 480

Gly Asp Lys Pro Ile Tyr Ile Gly Phe Gly Ser Leu Pro Val Gln Glu
                    485                 490                 495

Pro Glu Lys Met Thr Glu Ile Ile Val Glu Ala Leu Gln Arg Thr Lys
                500                 505                 510

Gln Arg Gly Ile Ile Asn Lys Gly Trp Gly Gly Leu Gly Asn Leu Lys
                515                 520                 525

Glu Pro Lys Asp Phe Val Tyr Leu Leu Asp Asn Val Pro His Asp Trp
            530                 535                 540

Leu Phe Pro Arg Cys Lys Ala Val Val His His Gly Gly Ala Gly Thr
545                 550                 555                 560

Thr Ala Ala Gly Leu Lys Ala Ser Cys Pro Thr Thr Ile Val Pro Phe
                565                 570                 575

Phe Gly Asp Gln Pro Phe Trp Gly Glu Arg Val His Ala Arg Gly Val
                580                 585                 590

Gly Pro Ser Pro Ile Pro Val Asp Glu Phe Ser Leu His Lys Leu Glu
                595                 600                 605

Asp Ala Ile Asn Phe Met Leu Asp Asp Lys Val Lys Ser Ser Ala Glu
            610                 615                 620

Thr Leu Ala Lys Ala Met Lys Asp Glu Asp Gly Val Ala Gly Ala Val
625                 630                 635                 640

Lys Ala Phe Phe Lys His Leu Pro Ser Ala Lys Gln Asn Ile Ser Asp
                    645                 650                 655

Pro Ile Pro Glu Pro Ser Gly Phe Leu Ser Phe Arg Lys Cys Phe Gly
                660                 665                 670

Cys Ser (2) INFORMATION FOR SEQ ID NO: 22:

(i) SEQUENCE CHARACTERISTICS:
        (A) LENGTH: 452 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 22:

Ile Pro Pro Met Gln Ile Val Ile Leu Ile Val Gly Thr Arg Gly Asp
1               5                   10                  15

Val Gln Pro Phe Val Ala Ile Ala Lys Arg Leu Gln Asp Tyr Gly His
                20                  25                  30

Arg Val Arg Leu Ala Thr His Ala Asn Tyr Lys Glu Phe Val Leu Thr
            35                  40                  45

Ala Gly Leu Glu Phe Phe Pro Leu Gly Gly Asp Pro Lys Leu Leu Ala
        50                  55                  60

Lys Tyr Met Val Lys Asn Lys Gly Phe Leu Pro Ser Gly Pro Ser Gly
65                  70                  75                  80

Ile Pro Ile Gln Arg Lys Gln Met Lys Glu Ile Ile Phe Ser Leu Leu
                85                  90                  95

Pro Ala Cys Lys Asp Pro Asp Pro Asp Thr Gly Ile Pro Phe Lys Val
                100                 105                 110

Asp Ala Ile Ile Ala Asn Pro Pro Ala Tyr Gly His Thr His Val Ala
            115                 120                 125

Glu Ala Leu Lys Val Pro Ile His Ile Phe Phe Thr Met Pro Trp Thr
        130                 135                 140
```

```
Pro Thr Ser Glu Phe Pro His Pro Leu Ser Arg Val Lys Thr Ser Ala
145                 150                 155                 160

Gly Tyr Arg Leu Ser Tyr Gln Ile Val Asp Ser Met Ile Trp Leu Gly
            165                 170                 175

Ile Arg Asp Met Ile Asn Glu Phe Arg Lys Lys Leu Lys Leu Arg
                180                 185                 190

Pro Val Thr Tyr Leu Ser Gly Ser Gln Gly Ser Gly Ser Asp Ile Pro
            195                 200                 205

His Gly Tyr Ile Trp Ser Pro His Leu Val Pro Lys Pro Lys Asp Trp
210                 215                 220

Gly Pro Lys Ile Asp Val Val Gly Phe Cys Phe Leu Asp Leu Ala Ser
225                 230                 235                 240

Asp Tyr Glu Pro Pro Glu Leu Val Lys Trp Leu Glu Ala Gly Asp
                245                 250                 255

Lys Pro Ile Tyr Val Gly Phe Gly Ser Leu Pro Val Gln Asp Pro Thr
                260                 265                 270

Lys Met Thr Glu Thr Ile Ile Gln Ala Leu Glu Met Thr Gly Gln Arg
            275                 280                 285

Gly Ile Ile Asn Lys Gly Trp Gly Gly Leu Gly Thr Leu Ala Glu Pro
290                 295                 300

Lys Asp Ser Ile Tyr Val Leu Asp Asn Cys Pro His Asp Trp Leu Phe
305                 310                 315                 320

Leu Gln Cys Lys Ala Val Val His His Gly Gly Ala Gly Thr Thr Ala
                325                 330                 335

Ala Gly Leu Lys Ala Ala Cys Pro Thr Thr Ile Val Pro Phe Phe Gly
            340                 345                 350

Asp Gln Gln Phe Trp Gly Asp Arg Val His Ala Arg Gly Val Gly Pro
            355                 360                 365

Val Pro Ile Pro Val Glu Gln Phe Asn Leu Gln Lys Leu Val Asp Ala
            370                 375                 380

Met Lys Phe Met Leu Glu Pro Glu Val Lys Glu Lys Pro Val Glu Leu
385                 390                 395                 400

Ala Lys Pro Met Glu Ser Glu Asp Gly Val Thr Gly Ala Val Arg Ala
            405                 410                 415

Phe Leu Lys His Leu Pro Ser Ser Lys Glu Asp Glu Asn Ser Pro Pro
            420                 425                 430

Pro Thr Pro His Gly Phe Leu Glu Phe Leu Gly Pro Val Ser Lys Cys
            435                 440                 445

Leu Gly Cys Ser
450

(2) INFORMATION FOR SEQ ID NO: 23:

(i) SEQUENCE CHARACTERISTICS:
        (A) LENGTH: 448 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 23:

Ile Pro Pro Met Gln Ile Val Met Leu Ile Val Gly Thr Arg Gly Asp
1               5                   10                  15

Val Gln Pro Phe Val Ala Ile Ala Lys Arg Leu Gln Asp Tyr Gly His
                20                  25                  30
```

-continued

```
Arg Val Arg Leu Ala Thr His Ala Asn Phe Lys Glu Phe Val Leu Thr
        35                  40                  45
Ala Gly Leu Glu Phe Tyr Pro Leu Gly Gly Asp Pro Lys Val Leu Ala
 50                      55                  60
Gly Tyr Met Val Lys Asn Lys Gly Phe Leu Pro Ser Gly Pro Ser Glu
 65                  70                  75                  80
Ile Pro Ile Gln Arg Asn Gln Met Lys Asp Ile Ile Tyr Ser Leu Leu
                 85                  90                  95
Pro Ala Cys Lys Glu Pro Asp Pro Asp Ser Gly Ile Ser Phe Lys Ala
             100                 105                 110
Asp Ala Ile Ile Ala Asn Pro Pro Ala Tyr Gly His Thr His Val Ala
         115                 120                 125
Glu Ala Leu Lys Ile Pro Ile His Val Phe Phe Thr Met Pro Trp Thr
 130                 135                 140
Pro Thr Ser Glu Phe Pro His Pro Leu Ser Arg Val Lys Gln Pro Ala
145                 150                 155                 160
Gly Tyr Arg Leu Ser Tyr Gln Ile Val Asp Ser Leu Ile Trp Leu Gly
                 165                 170                 175
Ile Arg Asp Met Val Asn Asp Leu Arg Lys Lys Leu Lys Leu Arg
             180                 185                 190
Pro Val Thr Tyr Leu Ser Gly Thr Gln Gly Ser Gly Ser Asn Ile Pro
         195                 200                 205
His Gly Tyr Met Trp Ser Pro His Leu Val Pro Lys Pro Lys Asp Trp
 210                 215                 220
Gly Pro Gln Ile Asp Val Val Gly Phe Cys Tyr Leu Asp Leu Ala Ser
225                 230                 235                 240
Asn Tyr Glu Pro Pro Ala Glu Leu Val Glu Trp Leu Glu Ala Gly Asp
                 245                 250                 255
Lys Pro Ile Tyr Ile Gly Phe Gly Ser Leu Pro Val Gln Glu Pro Glu
             260                 265                 270
Lys Met Thr Glu Ile Ile Val Glu Ala Leu Gln Arg Thr Lys Gln Arg
         275                 280                 285
Gly Ile Ile Asn Lys Gly Trp Gly Gly Leu Gly Asn Leu Lys Glu Pro
 290                 295                 300
Lys Asp Phe Val Tyr Leu Leu Asp Asn Val Pro His Asp Trp Leu Phe
305                 310                 315                 320
Pro Arg Cys Lys Ala Val Val His His Gly Ala Gly Thr Thr Ala
                 325                 330                 335
Ala Gly Leu Lys Ala Ser Cys Pro Thr Thr Ile Val Pro Phe Phe Gly
             340                 345                 350
Asp Gln Pro Phe Trp Gly Glu Arg Val His Ala Arg Gly Val Gly Pro
         355                 360                 365
Ser Pro Ile Pro Val Asp Glu Phe Ser Leu His Lys Leu Glu Asp Ala
 370                 375                 380
Ile Asn Phe Met Leu Asp Asp Lys Val Lys Ser Ser Ala Glu Thr Leu
385                 390                 395                 400
Ala Lys Ala Met Lys Asp Glu Asp Gly Val Ala Gly Ala Val Lys Ala
                 405                 410                 415
Phe Phe Lys His Leu Pro Ser Ala Lys Gln Asn Ile Ser Asp Pro Ile
             420                 425                 430
Pro Glu Pro Ser Gly Phe Leu Ser Phe Arg Lys Cys Phe Gly Cys Ser
         435                 440                 445
```

(2) INFORMATION FOR SEQ ID NO: 24:

(i) SEQUENCE CHARACTERISTICS:
        (A) LENGTH: 473 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 24:

```
Glu Asn Pro His Tyr Lys Thr Ser Ile Lys Pro Asn Lys Ser Tyr Lys
1               5                   10                  15

Phe Gly Leu Leu Thr Ile Gly Ser Arg Gly Asp Val Gln Pro Tyr Ile
            20                  25                  30

Ala Leu Gly Lys Gly Leu Ile Lys Glu Gly His Gln Val Val Ile Ile
            35                  40                  45

Thr His Ser Glu Phe Arg Asp Phe Val Glu Ser His Gly Ile Gln Phe
        50                  55                  60

Glu Glu Ile Ala Gly Asn Pro Val Glu Leu Met Ser Leu Met Val Glu
65                  70                  75                  80

Asn Glu Ser Met Asn Val Lys Met Leu Arg Glu Ala Ser Ser Lys Phe
                85                  90                  95

Arg Gly Trp Ile Asp Ala Leu Leu Gln Thr Ser Trp Glu Val Cys Asn
            100                 105                 110

Arg Arg Lys Phe Asp Ile Leu Ile Glu Ser Pro Ser Ala Met Val Gly
            115                 120                 125

Ile His Ile Thr Glu Ala Leu Gln Ile Pro Tyr Phe Arg Ala Phe Thr
        130                 135                 140

Met Pro Trp Thr Arg Thr Arg Ala Tyr Pro His Ala Phe Ile Val Pro
145                 150                 155                 160

Asp Gln Lys Arg Gly Gly Asn Tyr Asn Tyr Leu Thr His Val Leu Phe
                165                 170                 175

Glu Asn Val Phe Trp Lys Gly Ile Ser Gly Gln Val Asn Lys Trp Arg
            180                 185                 190

Val Glu Thr Leu Gly Leu Gly Lys Thr Asn Leu Phe Leu Leu Gln Gln
            195                 200                 205

Asn Asn Val Pro Phe Leu Tyr Asn Val Ser Pro Thr Ile Phe Pro Pro
        210                 215                 220

Ser Ile Asp Phe Ser Glu Trp Val Arg Val Thr Gly Tyr Trp Phe Leu
225                 230                 235                 240

Asp Asp Lys Ser Thr Phe Lys Pro Pro Ala Glu Leu Gln Glu Phe Ile
                245                 250                 255

Ser Glu Ala Arg Ser Lys Gly Lys Lys Leu Val Tyr Ile Gly Phe Gly
            260                 265                 270

Ser Ile Val Val Ser Asn Ala Lys Glu Met Thr Glu Ala Leu Val Glu
            275                 280                 285

Ala Val Met Glu Ala Asp Val Tyr Cys Ile Leu Asn Lys Gly Trp Ser
        290                 295                 300

Glu Arg Leu Gly Asp Lys Ala Ala Lys Lys Thr Glu Val Asp Leu Pro
305                 310                 315                 320

Arg Asn Ile Leu Asn Ile Gly Asn Val Pro His Asp Trp Leu Phe Pro
                325                 330                 335

Gln Val Asp Ala Ala Val His His Gly Gly Ser Gly Thr Thr Gly Ala
            340                 345                 350
```

```
Ser Leu Arg Ala Gly Leu Pro Thr Val Ile Lys Pro Phe Phe Gly Asp
        355                 360                 365

Gln Phe Phe Tyr Ala Gly Arg Val Glu Asp Ile Gly Val Gly Ile Ala
        370                 375                 380

Leu Lys Lys Leu Asn Ala Gln Thr Leu Ala Asp Ala Leu Lys Val Ala
385                 390                 395                 400

Thr Thr Asn Lys Ile Met Lys Asp Arg Ala Gly Leu Ile Lys Lys Lys
                405                 410                 415

Ile Ser Lys Glu Asp Gly Ile Lys Thr Ala Ile Ser Ala Ile Tyr Asn
                420                 425                 430

Glu Leu Glu Tyr Ala Arg Ser Val Thr Leu Ser Arg Val Lys Thr Pro
        435                 440                 445

Arg Lys Lys Glu Glu Asn Val Asp Ala Thr Lys Leu Thr Pro Ala Glu
        450                 455                 460

Thr Thr Asp Glu Gly Trp Thr Met Ile
465                 470

(2) INFORMATION FOR SEQ ID NO: 25:

(i) SEQUENCE CHARACTERISTICS:
        (A) LENGTH: 15 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO: 25:

Met Thr Glu Thr Thr Ile Ile Gln Ala Leu Glu Met Thr Gly Gln
1               5                   10                  15

(2) INFORMATION FOR SEQ ID NO: 26:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO: 26:

Met Thr Glu Thr Ile Ile Gln Ala Leu Glu Met Thr Gly Gln
1               5                   10

(2) INFORMATION FOR SEQ ID NO: 27:

(i) SEQUENCE CHARACTERISTICS:
        (A) LENGTH: 26 base pairs
        (B) TYPE: nucleic acid
        (C) STRANDEDNESS: unknown
        (D) TOPOLOGY: linear (ii) MOLECULE TYPE: other nucleic acid
        (A) DESCRIPTION: /desc = "synthetic DNA"

(ix) FEATURE:
        (A) NAME/KEY: misc_feature
        (B) LOCATION:3
        (D) OTHER INFORMATION:/note= "N=I"

(ix) FEATURE:
        (A) NAME/KEY: misc_feature
        (B) LOCATION:9
        (D) OTHER INFORMATION:/note= "N=I"

(ix) FEATURE:
```

(A) NAME/KEY: misc_feature
        (B) LOCATION:15
        (D) OTHER INFORMATION:/note= "N=A,G,C,T"

(ix) FEATURE:
        (A) NAME/KEY: misc_feature
        (B) LOCATION:18
        (D) OTHER INFORMATION:/note= "N=I"

(ix) FEATURE:
        (A) NAME/KEY: misc_feature
        (B) LOCATION:21
        (D) OTHER INFORMATION:/note= "N=I"

(xi) SEQUENCE DESCRIPTION: SEQ ID NO: 27:

GGNTAYGGNG AYGTNACNGT NGARGA                                26

(2) INFORMATION FOR SEQ ID NO: 28:

(i) SEQUENCE CHARACTERISTICS:
        (A) LENGTH: 23 base pairs
        (B) TYPE: nucleic acid
        (C) STRANDEDNESS: unknown
        (D) TOPOLOGY: linear (ii) MOLECULE TYPE: other nucleic acid
        (A) DESCRIPTION: /desc = "synthetic DNA"

(ix) FEATURE:
        (A) NAME/KEY: misc_feature
        (B) LOCATION:6
        (D) OTHER INFORMATION:/note= "N=I"

(ix) FEATURE:
        (A) NAME/KEY: misc_feature
        (B) LOCATION:9
        (D) OTHER INFORMATION:/note= "N=I"

(ix) FEATURE:
        (A) NAME/KEY: misc_feature
        (B) LOCATION:12
        (D) OTHER INFORMATION:/note= "N=I"

(ix) FEATURE:
        (A) NAME/KEY: misc_feature
        (B) LOCATION:21
        (D) OTHER INFORMATION:/note= "N=A,G,C,T"

(xi) SEQUENCE DESCRIPTION: SEQ ID NO: 28:

GAYGTNGGNG GNGARGAYGG NTA                                   23

(2) INFORMATION FOR SEQ ID NO: 29:

(i) SEQUENCE CHARACTERISTICS:
        (A) LENGTH: 34 base pairs
        (B) TYPE: nucleic acid
        (C) STRANDEDNESS: unknown
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 29:

GATCTAGACT CGAGGTCGAC TTTTTTTTTT TTTT                       34

(2) INFORMATION FOR SEQ ID NO: 30:

(i) SEQUENCE CHARACTERISTICS:
        (A) LENGTH: 21 base pairs
        (B) TYPE: nucleic acid
        (C) STRANDEDNESS: unknown
        (D) TOPOLOGY: linear (ii) MOLECULE TYPE: other nucleic acid
             (A) DESCRIPTION: /desc = "synthetic DNA"

(ix) FEATURE:
             (A) NAME/KEY: misc_feature
             (B) LOCATION:12
             (D) OTHER INFORMATION:/note= "N=I"

(ix) FEATURE:
             (A) NAME/KEY: misc_feature
             (B) LOCATION:18
             (D) OTHER INFORMATION:/note= "N=I"

(xi) SEQUENCE DESCRIPTION: SEQ ID NO: 30:

GCYTGDATDA TNGTYTCNGT C                                              21

(2) INFORMATION FOR SEQ ID NO: 31:

(i) SEQUENCE CHARACTERISTICS:
             (A) LENGTH: 34 amino acids
             (B) TYPE: amino acid
             (C) STRANDEDNESS: unknown
             (D) TOPOLOGY: unknown (ii) MOLECULE TYPE: peptide (v) FRAGMENT TYPE: N-terminal (xi) SEQUENCE DESCRIPTION: SEQ ID NO: 31:

Met Thr Met Ile Thr Pro Ser Ser Glu Leu Thr Leu Thr Lys Gly Asn
1               5                   10                  15

Lys Ser Trp Ser Ser Thr Ala Val Ala Ala Asp Ala Asp Glu Pro Thr
            20                  25                  30

Gly Gly (2) INFORMATION FOR SEQ ID NO: 32:

(i) SEQUENCE CHARACTERISTICS:
             (A) LENGTH: 21 base pairs
             (B) TYPE: nucleic acid
             (C) STRANDEDNESS: unknown
             (D) TOPOLOGY: linear (ii) MOLECULE TYPE: other nucleic acid
             (A) DESCRIPTION: /desc = "synthetic DNA"

(xi) SEQUENCE DESCRIPTION: SEQ ID NO: 32:

GATGAGGAAA TTCACTAGTT G                                              21

(2) INFORMATION FOR SEQ ID NO: 33:

(i) SEQUENCE CHARACTERISTICS:
             (A) LENGTH: 24 base pairs
             (B) TYPE: nucleic acid
             (C) STRANDEDNESS: unknown
             (D) TOPOLOGY: linear (ii) MOLECULE TYPE: other nucleic acid
             (A) DESCRIPTION: /desc = "synthetic DNA"

(xi) SEQUENCE DESCRIPTION: SEQ ID NO: 33:

GATGGATCCA CTTGATGTTG GAGG                                           24

(2) INFORMATION FOR SEQ ID NO: 34:

(i) SEQUENCE CHARACTERISTICS:
             (A) LENGTH: 40 amino acids
             (B) TYPE: amino acid
             (C) STRANDEDNESS: unknown (D) TOPOLOGY: unknown (ii) MOLECULE TYPE: peptide (v) FRAGMENT TYPE: N-terminal (xi) SEQUENCE DESCRIPTION: SEQ ID NO: 34:

Met Thr Met Ile Thr Pro Ser Ser Glu Leu Thr Leu Thr Lys Gly Asn
1               5                   10                  15

Lys Ser Trp Ser Ser Thr Ala Val Ala Ala Leu Glu Leu Val Asp Leu
            20                  25                  30

Asp Val Gly Gly Glu Asp Gly Tyr
        35                  40

(2) INFORMATION FOR SEQ ID NO: 35:

(i) SEQUENCE CHARACTERISTICS:
        (A) LENGTH: 30 base pairs
        (B) TYPE: nucleic acid
        (C) STRANDEDNESS: unknown
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 35:

GATATCTAGA GGCCGCAAAT TAAAGCCTTC                                           30

(2) INFORMATION FOR SEQ ID NO: 36:

(i) SEQUENCE CHARACTERISTICS:
        (A) LENGTH: 30 base pairs
        (B) TYPE: nucleic acid
        (C) STRANDEDNESS: unknown
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 36:

CCCGGGATCC GAGGGCCGCA TCATGTAATT                                           30

(2) INFORMATION FOR SEQ ID NO: 37:

(i) SEQUENCE CHARACTERISTICS:
        (A) LENGTH: 23 base pairs
        (B) TYPE: nucleic acid
        (C) STRANDEDNESS: unknown
        (D) TOPOLOGY: linear (ii) MOLECULE TYPE: other nucleic acid
        (A) DESCRIPTION: /desc = "synthetic DNA"

(ix) FEATURE:
        (A) NAME/KEY: misc_feature
        (B) LOCATION:3
        (D) OTHER INFORMATION:/note= "N=I"

(ix) FEATURE:
        (A) NAME/KEY: misc_feature
        (B) LOCATION:6
        (D) OTHER INFORMATION:/note= "N=I"

(ix) FEATURE:
        (A) NAME/KEY: misc_feature
        (B) LOCATION:9
        (D) OTHER INFORMATION:/note= "N=I"

(ix) FEATURE:
        (A) NAME/KEY: misc_feature
        (B) LOCATION:12

(D) OTHER INFORMATION:/note= "N=I"

(ix) FEATURE:
        (A) NAME/KEY: misc_feature
        (B) LOCATION:21
        (D) OTHER INFORMATION:/note= "N=I"

(xi) SEQUENCE DESCRIPTION: SEQ ID NO: 37:

GSNWCNVSNG GNGAYGTHYW NCC                                                        23

(2) INFORMATION FOR SEQ ID NO: 38:

(i) SEQUENCE CHARACTERISTICS:
        (A) LENGTH: 23 base pairs
        (B) TYPE: nucleic acid
        (C) STRANDEDNESS: unknown
        (D) TOPOLOGY: linear (ii) MOLECULE TYPE: other nucleic acid
        (A) DESCRIPTION: /desc = "synthetic DNA"

(ix) FEATURE:
        (A) NAME/KEY: misc_feature
        (B) LOCATION:3
        (D) OTHER INFORMATION:/note= "N=I"

(ix) FEATURE:
        (A) NAME/KEY: misc_feature
        (B) LOCATION:6
        (D) OTHER INFORMATION:/note= "N=I"

(ix) FEATURE:
        (A) NAME/KEY: misc_feature
        (B) LOCATION:9
        (D) OTHER INFORMATION:/note= "N=I"

(ix) FEATURE:
        (A) NAME/KEY: misc_feature
        (B) LOCATION:12
        (D) OTHER INFORMATION:/note= "N=I"

(ix) FEATURE:
        (A) NAME/KEY: misc_feature
        (B) LOCATION:15
        (D) OTHER INFORMATION:/note= "N=I"

(xi) SEQUENCE DESCRIPTION: SEQ ID NO: 38:

GTNGTNCCNS HNCCNSCRTG RTG                                                        23

(2) INFORMATION FOR SEQ ID NO: 39:

(i) SEQUENCE CHARACTERISTICS:
        (A) LENGTH: 23 base pairs
        (B) TYPE: nucleic acid
        (C) STRANDEDNESS: unknown
        (D) TOPOLOGY: linear (ii) MOLECULE TYPE: other nucleic acid
        (A) DESCRIPTION: /desc = "synthetic DNA"

(ix) FEATURE:
        (A) NAME/KEY: misc_feature
        (B) LOCATION:3
        (D) OTHER INFORMATION:/note= "N=I"

(ix) FEATURE:
        (A) NAME/KEY: misc_feature
        (B) LOCATION:6
        (D) OTHER INFORMATION:/note= "N=I"

(ix) FEATURE:
        (A) NAME/KEY: misc_feature
        (B) LOCATION:12
        (D) OTHER INFORMATION:/note= "N=I"

```
    (ix) FEATURE:
         (A) NAME/KEY: misc_feature
         (B) LOCATION:18
         (D) OTHER INFORMATION:/note= "N=I"

(xi) SEQUENCE DESCRIPTION: SEQ ID NO: 39:

GTNSKNGTCC ANGGCATNGT RAA                                            23

(2) INFORMATION FOR SEQ ID NO: 40:

(i) SEQUENCE CHARACTERISTICS:
        (A) LENGTH: 53 amino acids
        (B) TYPE: amino acid
        (C) STRANDEDNESS: unknown
        (D) TOPOLOGY: unknown (ii) MOLECULE TYPE: peptide (v) FRAGMENT TYPE: N-terminal (xi) SEQUENCE DESCRIPTION: SEQ ID NO: 40:

Met Thr Met Ile Thr Pro Ser Ser Glu Leu Thr Leu Thr Lys Gly Asn
1               5                   10                  15

Lys Ser Trp Ser Ser Thr Ala Val Ala Ala Leu Glu Leu Val Asp
            20                  25                  30

Pro Pro Gly Cys Arg Asn Ser Glu Phe Gly Thr Pro Leu Ile Leu Ser
        35                  40                  45

Phe Thr Phe Trp Asp
    50

(2) INFORMATION FOR SEQ ID NO: 41:

(i) SEQUENCE CHARACTERISTICS:
        (A) LENGTH: 4 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO: 41:

His His Gly Gly
1

(2) INFORMATION FOR SEQ ID NO: 42:

(i) SEQUENCE CHARACTERISTICS:
        (A) LENGTH: 27 amino acids
        (B) TYPE: amino acid
        (C) STRANDEDNESS: unknown
        (D) TOPOLOGY: unknown (ii) MOLECULE TYPE: peptide (ix) FEATURE:
         (A) NAME/KEY: Modified-site
         (B) LOCATION:group(5..16, 18..26)
         (D) OTHER INFORMATION:/label= Xaa
                /note= "arbitrary amino acids"

(xi) SEQUENCE DESCRIPTION: SEQ ID NO: 42:

His His Gly Gly Xaa Xaa Xaa Xaa Xaa Xaa Xaa Xaa Xaa Xaa Xaa
1               5                   10                  15

Pro Xaa Xaa Xaa Xaa Xaa Xaa Xaa Xaa Xaa Gln
            20                  25
```